(12) United States Patent
Landa et al.

(10) Patent No.: US 11,560,670 B2
(45) Date of Patent: Jan. 24, 2023

(54) METHODS FOR TEXTILE TREATMENT

(71) Applicant: LANDA LABS (2012) LTD., Rehovot (IL)

(72) Inventors: Benzion Landa, Nes Ziona (IL); Sagi Abramovich, Ra'anana (IL)

(73) Assignee: LANDA LABS (2012) LTD., Rehovot (IL)

(*) Notice: Subject to any disclaimer, the term of this patent is extended or adjusted under 35 U.S.C. 154(b) by 275 days.

(21) Appl. No.: 16/935,244

(22) Filed: Jul. 22, 2020

(65) Prior Publication Data

US 2020/0347546 A1 Nov. 5, 2020

Related U.S. Application Data

(63) Continuation-in-part of application No. PCT/IB2019/050509, filed on Jan. 22, 2019.

(60) Provisional application No. 62/620,083, filed on Jan. 22, 2018.

(51) Int. Cl.
| | |
|---|---|
| *D06P 1/54* | (2006.01) |
| *D06P 1/00* | (2006.01) |
| *D06P 1/44* | (2006.01) |
| *D06P 1/52* | (2006.01) |
| *D06P 5/22* | (2006.01) |

(52) U.S. Cl.
CPC ............ *D06P 1/54* (2013.01); *D06P 1/008* (2013.01); *D06P 1/445* (2013.01); *D06P 1/5292* (2013.01); *D06P 5/22* (2013.01)

(58) Field of Classification Search
CPC .. D06P 1/54; D06P 1/008; D06P 1/445; D06P 1/5292; D06P 5/22
See application file for complete search history.

(56) References Cited

U.S. PATENT DOCUMENTS

| | | | |
|---|---|---|---|
| 6,248,855 B1 | 6/2001 | Dalle | |
| 2009/0183320 A1 | 7/2009 | Benabdillah | |
| 2010/0083446 A1* | 4/2010 | Brun | A61K 8/891 |
| | | | 8/405 |
| 2011/0064683 A1 | 3/2011 | Jordan et al. | |
| 2011/0236334 A1 | 9/2011 | Jordan | |
| 2011/0305653 A1 | 12/2011 | Jordan | |
| 2012/0045177 A1 | 6/2012 | Thompson | |
| 2013/0149358 A1 | 6/2013 | Calaco | |
| 2014/0308229 A1 | 10/2014 | Bouzeloc | |
| 2014/0356309 A1 | 12/2014 | Ozaki | |
| 2015/0174051 A1 | 6/2015 | Teboul | |
| 2015/0297495 A1 | 10/2015 | Patel | |
| 2015/0299949 A1 | 10/2015 | Sutherland | |
| 2016/0235655 A1 | 8/2016 | Herrlein | |
| 2016/0235658 A1 | 8/2016 | Herrlein | |
| 2016/0310378 A1 | 10/2016 | Herrlein | |

FOREIGN PATENT DOCUMENTS

| | | |
|---|---|---|
| CN | 102791251 | 11/2012 |
| EP | 0528602 | 2/1993 |
| EP | 2415797 | 2/2012 |
| EP | 3058934 | 8/2016 |
| WO | 97/18795 | 5/1995 |
| WO | 2004/037944 | 5/2004 |
| WO | 2009/061360 | 5/2009 |
| WO | 2011/128255 | 10/2011 |
| WO | 2018/187246 | 10/2018 |

\* cited by examiner

*Primary Examiner* — Amina S Khan
(74) *Attorney, Agent, or Firm* — JMB Davis Ben-David

(57) ABSTRACT

There is disclosed a method of coating textile fibers, the method comprising applying, on the external surface of textile fibers, a pre-treated oil-in-water emulsion comprising: (i) an aqueous phase containing water; and (ii) a pre-treated oil phase containing at least one reactive condensation-curable film-forming amino-silicone pre-polymer that, subsequent to condensation curing optionally in presence of additional reactants, forms an amino-silicone coat. The pre-treated reactive oil phase includes at least one pre-treated reactant or pre-treated pre-polymer. An aqueous dispersion containing particles of a hydrophilic polymeric material is then applied to the amino-silicone coat, so as to form a polymeric layer thereon. At least one of the oil-in-water emulsion forming a first coat and of the aqueous dispersion forming a second coat may further contain a plurality of sub-micronic pigment particles dispersed therein. Suitable compositions and kits including the same are also disclosed, as well as fibers coated thereby.

12 Claims, 5 Drawing Sheets

METHODS FOR TEXTILE TREATMENT

CROSS-REFERENCE TO RELATED APPLICATIONS

This application is a Continuation-In-Part (CIP) of International Application No. PCT/IB2019/050509, filed Jan. 22, 2019, which claims priority from patent application U.S. 62/620,083, filed Jan. 22, 2018. All of the aforementioned applications are incorporated herein by reference for all purposes as if fully set forth herein.

FIELD

The present disclosure relates to methods for coloring textile and fibers thereof. Methods for preparing suitable coloring compositions are also disclosed, as well as kits enabling practicing such methods, and the coated fibers and textile resulting therefrom.

BACKGROUND

In textile manufacturing, the coloration is one of the most important steps for providing the fabric its final appearance, including color and luster. There are numerous coloration methods which have various efficacies, depending on the types of textile fibers that make up the yarns and fabric, as well as when they are applied during the manufacturing process.

Textile fibers may be of natural origin, or artificially made from synthetic polymers. Natural fibers usually exhibit large variations in length, shape and quality of its individual constituting filaments, and may also contain impurities, derived from the animal or plant from which they originate. Artificial or synthetic fibers, being prepared under controlled conditions, are typically of more uniform characteristics and may generally contain less impurities which may impede coloring.

Natural fibers include keratinous protein fibers of animal-origin, such as wool, silk, mohair or cashmere; and cellulose fibers of plant-origin, such as cotton, linen, ramie or hemp. Artificial fibers include synthetic fibers, such as nylons, polyesters, acrylics, rayon or polyolefins; and regenerated fibers, such as viscose or cellulose acetate. Synthetic fibers could be manufactured according to desired specification, for instance, with predetermined dimensions (e.g., diameter), mechanical properties, and even shade (e.g., the coloring agent being mixed with the polymer ahead of forming a strand). Natural fibers, however, are typically prepared as follows.

Monofilament fibers are spun or otherwise grouped together to form a thread, which in turn can be assembled to form a yarn, which may be arranged to form a fabric by a number of techniques (e.g., by weaving, knitting, crocheting, felting, sewing, etc.). The fabric can then be cut, and/or various pieces assembled to form any intended article made of textile (e.g., a garment).

Coloration of textile fibers can be performed at the thread or yarn stage, the fabric stage or the garment stage, each stage having its own advantages and disadvantages. For example, fabric or garment coloring can be more economical, the coloration being performed only where needed, but it may be less efficient when high coloring density is desired, and the fabric arrangement reduces exposure of its constituting fibers to the colorant. In such a case, coloration of the textile fibers at the earlier stage of thread and yarn manufacturing may prove more advantageous.

Coloring compositions for textile may comprise chemical, organic, herbal or natural coloring agents. Regardless of their origin, the coloring agents generally fall into two categories, a) soluble dyes that may penetrate the fibers, and b) water-insoluble pigments, which in view of their dimensions are typically restricted to external coloring of fibers.

When coloring textile, a permanent effect is generally desired, namely that the colors retain their original shades over time (e.g., upon exposure to light) and that they do not wash off (e.g., upon exposure to chemical and/or mechanical stress, such as applied, for instance, during cleaning). Dyes being relatively small molecules, they may more easily permeate textile fibers and be retained therein, optionally following the application of an additional treatment step (e.g., using a fixative). Therefore, dyes are the leading coloring agents, when considering chemical- and/or mechanical-resistance, their relatively internal position within the textile fibers physically protecting the resulting color from undesired fading. However, dyes are generally less resistant than pigments to sun exposure.

While pigments should be preferred over dyes with respect to resistance to sun light, their relatively external position on the outer surface of the textile fibers increase the risk of discoloration as a result of undesired chemical- and/or mechanical exposure (e.g., exposure to detergents and abrasion by contact during washing).

Thus, there remains a need for textile coloring methods, which provide efficient and, when desired, long-lasting coloration of textile fibers.

SUMMARY

The present inventors have disclosed methods and compositions for coating or coloring keratinous fibers, such as human hair, the compositions being aqueous dispersions comprising a plurality of polymeric particles, formed of a hydrophilic polymeric material having neutralized acid moieties, wherein the hydrophilic polymeric material optionally envelops at least one pigment core particle. The optionally pigmented aqueous dispersions are applied onto mammalian hair having an amino-silicone coating, so as to produce an overlying, optionally pigmented polymeric layer. The amino-silicone coating can result from the application onto the hair fibers of at least one reactive condensation-curable amino functional silicone pre-polymer disposed in the oil phase of an oil-in-water emulsion. The oil phase may further comprise same or different pigments to strengthen or modify the coloration contributed by the pigmented polymeric layer. The amino-silicone coating is formed by in situ condensation-curing of the pre-polymers on the individual hair fibers. Hair fibers externally coated by these two sequential coats advantageously provides one or more of a pleasant feel to the touch, a satisfactory coloration (e.g., in terms of optical density, depth, vividness, etc.) and color permanency (e.g., resistance to repeated washes or other external factors). Details concerning this technology, associated methods and compositions, can be found in WO 2018/187246.

The present disclosure relates to methods of pre-treatment of the oil phase and/or of its constituents, the methods providing for improved performance of the amino-silicone emulsion and amino-silicone coating resulting therefrom. The improved performance of a first amino-silicone coat enhances in turn the effects of a second polymeric coat. Any feature or combination of features of the present disclosure can be combined with any feature or combination of features as detailed in WO 2018/187246. While the use disclosed and claimed in WO 2018/187246 was the coating or coloration of individual keratinous mammalian hair fibers, the present methods and enabling compositions further allow coating or coloring textile fibers.

As used herein, the terms "mammalian hair", "individual mammalian hair", "mammalian hair fibers", "individual mammalian hair fibers", and like variants, can be used interchangeably. As used herein, the term "textile fibers" refers to any form of a natural or synthetic textile material, from the primary form of a thread (typically formed from a plurality of individual filaments in elongated overlapping alignment) or a yarn (typically formed from a plurality of individual threads in elongated overlapping alignment) to the more advanced form of a fabric made therefrom by any known method such as weaving, knitting, crocheting, felting and sewing. Unless otherwise clear from context, this terminology further encompasses final products prepared from such woven or non-woven fabrics.

While the term "fibers" may refer to hair filaments, to textile filaments or to both hair and textile filaments, as clear from context, such filaments are typically distinctly arranged in these two categories. Mammalian hair fibers are typically arranged as individual fibers, each attached to a mammalian subject at a distinct locus. For instance, human hair fibers are attached by their roots to a multitude of points over a scalp, and other than for undesired entanglement, there would be no physical attachment of human hair fibers one with another. Mammalian hair fibers can be viewed as a spaced array of mono-filaments. In contrast, in order to provide the mechanical properties necessary for the use of textile threads or yarns in the manufacturing of fabrics or final products made of textile materials, the textile fibers, in particular natural textile fibers, are essentially composed of a plurality of individual filaments (e.g., assembled by spinning) overlapping one with another along the entire length of the strand. Hence, textile fibers, with the possible exception of some synthetic fibers, do not refer to mono-filaments, but at least to elongated thread of compactly packed multi-filaments.

In a first aspect, there is provided a method of coating textile fibers, the method comprising:
(a) providing an oil phase containing at least one reactive condensation-curable film-forming amino-silicone pre-polymer, said oil phase fulfilling at least one of the following:
  (i) said at least one reactive condensation-curable film-forming amino-silicone pre-polymer includes at least one reactive condensation-curable film-forming amino-silicone monomer having a molecular weight of at most 1000 g/mole;
  (ii) said oil phase further contains a non-amino cross-linking agent adapted or selected to cure said at least one reactive condensation-curable film-forming amino-silicone pre-polymer, said non-amino cross-linking agent having a molecular weight of at most 1000 g/mole;
  (iii) said oil phase according to (i) and/or (ii) further comprising at least one of a silicone oil, an amino-silicone oil and a reactive hydrophobic inorganic filler; and
wherein said oil phase contains at least 0.01 wt. %, at least 0.05 wt. %, at least 0.1 wt. %, at least 0.15 wt. %, at least 0.2 wt. %, at least 0.25 wt. %, at least 0.5 wt. %, at least 0.75 wt. %, or at least 1 wt. % of water by weight of said oil phase;
(b) after subjecting said oil phase to a pre-treatment duration to obtain a pre-treated oil phase, emulsifying said pre-treated oil phase with an aqueous phase containing water, so as to obtain a pre-treated oil-in-water emulsion;
(c) applying, on an external surface of the textile fibers, said pre-treated oil-in-water emulsion;
(d) after partial condensation curing of said pre-polymer of the pre-treated oil-in-water emulsion has occurred so as to form an at least partially cured amino-silicone coat on the external surface of the textile fibers, optionally washing the textile fibers with a rinsing liquid to remove any excess of said pre-treated oil-in-water emulsion;
(e) applying, on the at least partially cured amino-silicone film, an aqueous dispersion containing a plurality of polymeric particles being dispersed within said aqueous dispersion, the polymeric particles being formed of a hydrophilic polymeric material having neutralized acid moieties, to produce an overlying, polymeric layer adhering to the external surface of the amino-silicone film; and optionally
(f) washing the textile fibers with a rinsing liquid to remove any excess of said aqueous dispersion.

In a second aspect, there is provided a method of coating textile fibers, the method comprising:
(a) providing an oil phase containing at least one reactive condensation-curable film-forming amino-silicone pre-polymer, said oil phase fulfilling at least one of the following:
  (i) said at least one reactive condensation-curable film-forming amino-silicone pre-polymer includes at least one reactive condensation-curable film-forming amino-silicone monomer having a molecular weight of at most 1000 g/mole;
  (ii) said oil phase further contains a non-amino cross-linking agent adapted or selected to cure said at least one reactive condensation-curable film-forming amino-silicone pre-polymer, said non-amino cross-linking agent having a molecular weight of at most 1000 g/mole; and
  (iii) said oil phase according to (i) and/or (ii), wherein at least one of said reactive condensation-curable film-forming amino-silicone pre-polymer, said reactive condensation-curable film-forming amino-silicone monomer, said non-amino cross-linking agent, or any of a silicone oil, an amino-silicone oil and a reactive hydrophobic inorganic filler optionally further comprised therein, is a water-rich reactant; and
(b) pre-treating said oil phase for a pre-treatment duration, so as obtain a pre-treated oil phase having at least 0.01 wt. %, at least 0.05 wt. %, at least 0.1 wt. %, at least 0.15 wt. %, at least 0.2 wt. %, at least 0.25 wt. %, at least 0.5 wt. %, at least 0.75 wt. %, or at least 1 wt. % of water by weight of said pre-treated oil phase;
(c) emulsifying said pre-treated oil phase with an aqueous phase containing water, so as to obtain a pre-treated oil-in-water emulsion;
(d) applying, on an external surface of the textile fibers, said pre-treated oil-in-water emulsion;
(e) after partial condensation curing of said pre-polymer of the pre-treated oil-in-water emulsion has occurred so as to form an at least partially cured amino-silicone coat on the external surface of the textile fibers, optionally washing the textile fibers with a rinsing liquid to remove any excess of said pre-treated oil-in-water emulsion;
(f) applying, on the at least partially cured amino-silicone film, an aqueous dispersion containing a plurality of polymeric particles being dispersed within said aqueous dispersion, the polymeric particles being formed of a hydrophilic polymeric material having neutralized acid moieties, to produce an overlying, polymeric layer adhering to the external surface of the amino-silicone film; and optionally
(g) washing the textile fibers with a rinsing liquid to remove any excess of said aqueous dispersion.

In a third aspect, there is provided a method of treating an external surface of textile fibers, the method comprising:

(a) pre-treating an oil phase containing at least one reactive condensation-curable film-forming amino-silicone pre-polymer that, subsequent to condensation curing, forms an amino-silicone coat, said oil phase fulfilling at least one of the following:
  (i) said at least one reactive condensation-curable film-forming amino-silicone pre-polymer includes at least one reactive condensation-curable film-forming amino-silicone monomer having a molecular weight of at most 1,000 g/mole, at least one of said pre-polymer and said monomer being a water-rich or pre-treated reactant;
  (ii) said at least one reactive condensation-curable film-forming amino-silicone pre-polymer includes at least one reactive condensation-curable film-forming amino-silicone monomer having a molecular weight of at most 1,000 g/mole, the oil phase further comprising at least one water-rich or pre-treated reactant;
  (iii) said oil phase further contains a non-amino cross-linking agent adapted or selected to cure said pre-polymer, said non-amino cross-linking agent having a molecular weight of at most 1,000 g/mole, at least one of said pre-polymer and said cross-linking agent being a water-rich or pre-treated reactant; and
  (iv) said oil phase further contains a non-amino cross-linking agent adapted or selected to cure said pre-polymer, said non-amino cross-linking agent having a molecular weight of at most 1,000 g/mole, the oil phase further comprising at least one water-rich or pre-treated reactant;

(b) incubating said oil phase for a pre-treatment duration, so as obtain a pre-treated oil phase;
(c) emulsifying said pre-treated oil phase with an aqueous phase containing water, so as to obtain a pre-treated oil-in-water emulsion;
(d) applying, on an external surface of the textile fibers, said pre-treated oil-in-water emulsion;
(e) after partial condensation curing of said pre-polymer of the pre-treated oil-in-water emulsion has occurred so as to form an at least partially cured amino-silicone coat on the external surface of the textile fibers, optionally washing the textile fibers with a rinsing liquid to remove any excess of said pre-treated oil-in-water emulsion;
(f) applying, on the at least partially cured amino-silicone film, an aqueous dispersion containing a plurality of polymeric particles being dispersed within said aqueous dispersion, the polymeric particles being formed of a hydrophilic polymeric material having neutralized acid moieties, to produce an overlying, polymeric layer adhering to the external surface of the amino-silicone film; and optionally
(g) washing the textile fibers with a rinsing liquid to remove any excess of said aqueous dispersion.

In some embodiments of any one of said first, second and third aspect, the textile fibers are natural keratinous fibers. In an alternative of such embodiments, the textile fibers are natural non-keratinous fibers. In a further alternative of such embodiments, the textile fibers are synthetic fibers, in which case the textile fiber may optionally be a mono-filament.

In some embodiments of any one of said aspects, the pre-treated oil-in-water emulsion can further comprise a pigment, the pigment particles being dispersed in the pre-treated oil phase, optionally in presence of a pigment dispersant. In such cases, the resulting amino-silicone coating or coat may be termed a "pigmented amino-silicone coating" and similar variants. Furthermore, the pigment and/or the pigment dispersant can be, in some embodiments, a water-rich reactant or a pre-treated reactant.

As used herein, the term "water-rich reactant" refers to a reactant containing a certain amount of water, in ranges further detailed herein, whereas a "pre-treated reactant" is a reactant treated with an aqueous pre-treatment solution, so that following incubation with the aqueous pre-treatment solution, the pre-treated reactant contains water in a similar range of desired amount. The reactant treated with the aqueous pre-treatment solution can be a substantially dry reactant or a water-rich reactant having a water content deemed insufficient. Regardless of the way such reactants are obtained, as "water-rich" per se or pre-treated, the reactants able to convey water to the compositions according to the present methods can collectively be referred to as "water-enriched" reactants. Oil phase components which can be water-enriched reactants (whether originally water-rich or pre-treated with an aqueous pre-treatment solution) include reactive condensation-curable film-forming amino-silicone pre-polymers, for instance, reactive condensation-curable film-forming amino-silicone monomers, non-amino cross-linking agents, silicone oils, amino-silicone oils, dispersants and fillers (e.g., a reactive hydrophobic inorganic filler).

In one embodiment of any one of said aspects, the aqueous dispersion can further comprise a pigment, at least a portion of the pigment particle being enveloped in the hydrophilic polymeric material in at least a portion of the polymeric particles. In such case, the resulting polymeric layer may be termed a "pigmented polymeric layer" and similar variants.

In a further embodiment of any one of said aspects, the aqueous dispersion and the pre-treated oil-in-water emulsion may each independently further comprise a pigment being same or different, the pigment particles being disposed within the dispersion and the emulsion as aforesaid and as described in more details herein-below.

In an alternative embodiment of any one of said aspects, the pre-treated oil-in-water emulsion and the aqueous dispersion are substantially devoid of coloring agents, such as pigments, a coating resulting from the present methods being predominantly intended to reduce, delay or prevent loss of color from a colored textile fiber. As readily appreciated, the presence of pigments in any of the layer of the present coating is not expected to diminish this color retention effect, but may mask it in view of the own coloring effect of the pigmented coatings. Therefore, the absence of pigments from the present coatings is not essential to obtain said reduction, delay or prevention of color loss from a colored textile fiber.

In another aspect, there is provided a method of treating an external surface of textile fibers, as herein described, wherein prior to the application of an oil-in-water emulsion according to the present teachings, and optionally following a degreasing step, if performed, applying, on the external surface of the textile fibers, a film-forming masking formulation so as to produce a masking film on the textile fibers. In some embodiments, the film-forming masking formulation is an oil-in-water emulsion as herein described, the emulsion further comprising metallic pigments adapted or selected to mask, following their application onto the textile fibers, the color of the fibers. In some embodiments, the film-forming masking formulation is an aqueous dispersion as herein described, the dispersion comprising metallic pigments adapted or selected to mask, the color of the fibers, following their application onto the textile fibers.

In some embodiments of said aspect, the pre-treated oil-in-water emulsions are applied on an external surface of textile fibers, and the method is used for coating textile fibers. In some embodiments, the textile fibers are natural keratinous fibers. In an alternative of such embodiments, the textile fibers are natural non-keratinous fibers. In a further alternative of such embodiments, the textile fibers are synthetic fibers, in which case the textile fiber may optionally be a mono-filament.

In another aspect, there is provided a textile fiber having a coating on its external surface, wherein the coating comprises:
a) a thermosetting layer comprising or consisting of cross-linked amino-silicones, the thermosetting layer having a Tg between −100° C. and +20° C. and being in contact with the textile fibers; and
b) a thermoplastic layer comprising a polymeric material having acid moieties, the thermoplastic layer being disposed on the thermosetting layer.

In some embodiments, the coating further comprises a pigment, optionally as a plurality of sub-micronic pigment particles, wherein the pigment is present in the thermosetting layer and/or in the thermoplastic layer.

In some embodiments, the coating further comprises a reactive hydrophobic inorganic filler in the thermosetting layer.

In some embodiments, the thermoplastic layer of the coated textile fibers further comprises alkali metal ions.

In some embodiments of said aspect, the textile fibers are keratinous or non-keratinous, natural or synthetic, fibers. In particular embodiments, the textile fibers are non-keratinous.

In another aspect, there is provided a method of reducing, delaying or preventing color loss in colored textile fibers, the method comprising coating said textile fibers according to the methods of the present invention.

In another aspect, there is provided a kit for producing a reactive composition for coating, coloring or masking an external surface of textile fibers, the kit comprising:
(a) a first oil phase compartment containing a first oil phase including:
  (i) at least one reactive condensation-curable film-forming amino-silicone monomer having a molecular weight of at most 1000 g/mole; and optionally,
  (ii) a non-amino cross-linking agent; and further optionally,
  (iii) at least one of an amino-silicone oil and a non-amino-silicone oil; and further optionally,
  (iv) at least one reactive condensation-curable film-forming amino-silicone pre-polymer including at least one of a reactive condensation-curable film-forming amino-silicone polymer and a reactive condensation-curable film-forming amino-silicone oligomer;
(b) an aqueous dispersion compartment containing an aqueous dispersion including:
  (i) an aqueous medium; and
  (ii) sub-micronic particles including, or made of, a hydrophilic polymeric material having neutralized acid moieties, disposed within the aqueous medium, each of at least a portion of the sub-micronic particles optionally containing at least one pigment particle, the at least one pigment particle optionally being at least partially enveloped by the polymeric material; and
(c) an optional second oil phase compartment containing a second oil phase including:
  (i) at least one of an or the amino-silicone oil and a or the non-amino-silicone oil, and optionally,
  (ii) a solid, hydrophobic reactive inorganic filler; and further optionally,
  (iii) the at least one reactive condensation-curable film-forming amino-silicone pre-polymer including at least one of a reactive condensation-curable film-forming amino-silicone polymer and a reactive condensation-curable film-forming amino-silicone oligomer; and further optionally,
  (iv) pigment particles, disposed within the second oil phase;
wherein at least one of the first oil phase compartment or optional second oil phase compartment further contains an aqueous pre-treatment solution; and
wherein the kit further optionally comprises at least one of: a thickening agent, an emulsifier, a surfactant and a dispersant.

In some embodiments of said aspect, the textile fibers, the surface of which being modified as per the present teachings, are of natural origin, being animal or plant-based materials, said materials being detached from the body of the animal or isolated from the plant the textile fibers would originate from. In one embodiment, the coatings achieved by the reactive compositions of the kit may be used to reduce, delay or prevent color loss in colored textile fibers, by applying said composition on colored textile fibers according to the methods of the present invention.

In one particular embodiment, the methods and kits of the present invention are applied and used on natural keratinous fibers. In another embodiment, the methods and kits are applied and used on natural non-keratinous fibers. In some embodiments of the present invention, the methods and kits are applied and used on synthetic fibers.

BRIEF DESCRIPTION OF THE DRAWINGS

Some embodiments of the invention are described herein with reference to the accompanying figures. The description, together with the figures, makes apparent to a person having ordinary skill in the art how some embodiments of the invention may be practiced.

The figures are for the purpose of illustrative discussion and no attempt is made to show structural details of an embodiment in more detail than is necessary for a fundamental understanding of the invention. For the sake of clarity, some objects depicted in the figures are not to scale.

In the Figures:

FIG. 1A is a schematic illustration of a single textile thread in presence of some emulsion droplets containing reactive amino-silicone pre-polymers, according to some embodiments;

FIG. 1B is a schematic illustration representing how some of the emulsion droplets of FIG. 1A can migrate towards the textile thread and arrange thereupon;

Figure 1A:
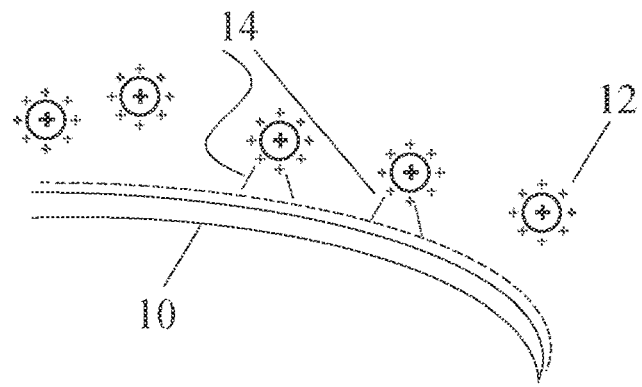
Figure 1B:
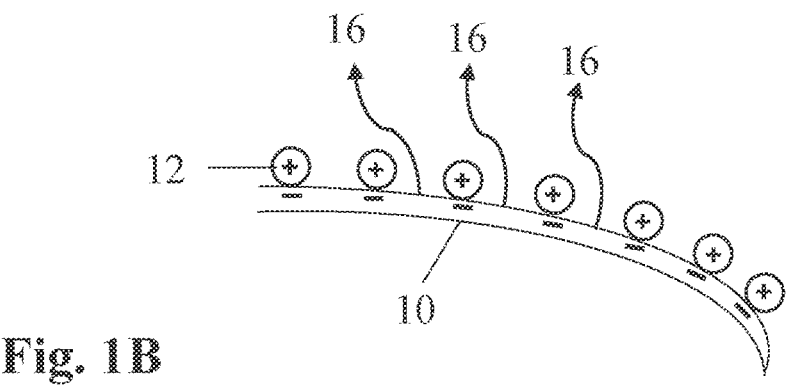
Figure 1C:
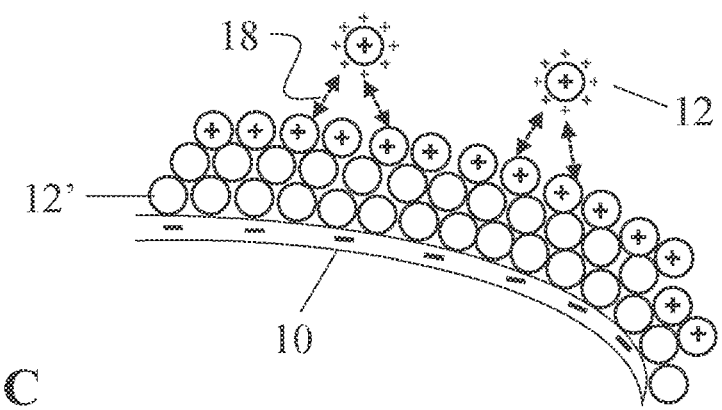
Figure 1D:
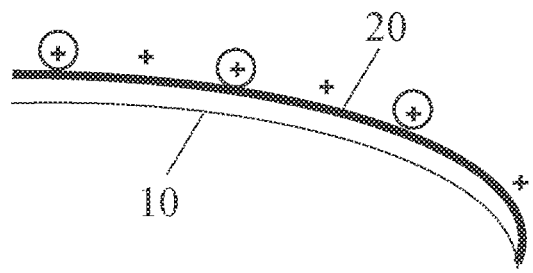
Figure 1E:
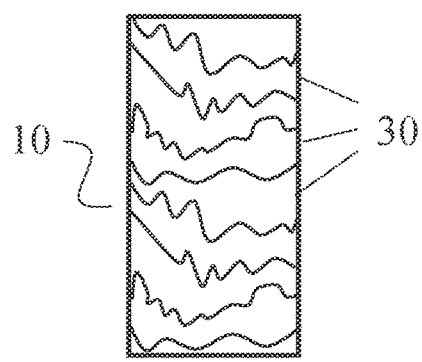
Figure 1F:
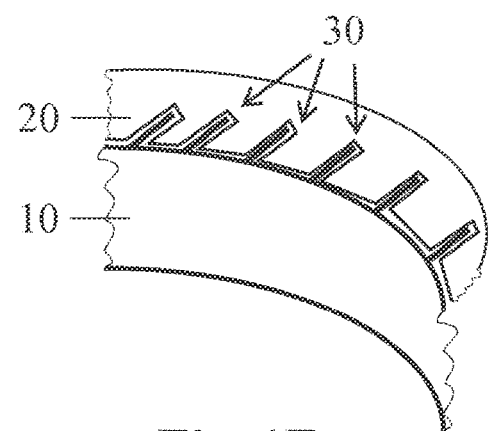
Figure 2A:
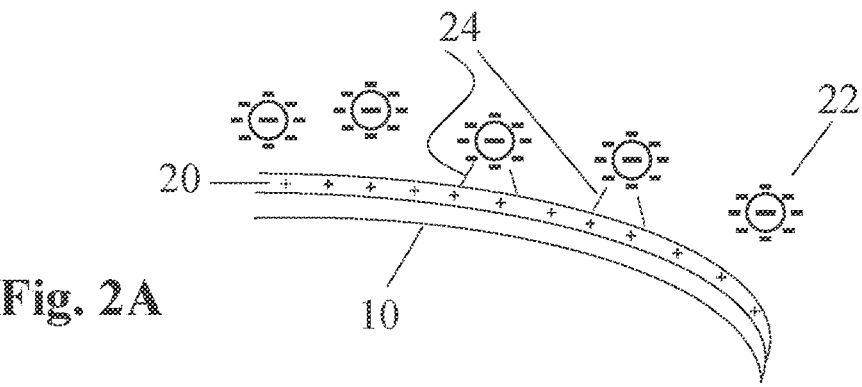
Figure 2B:
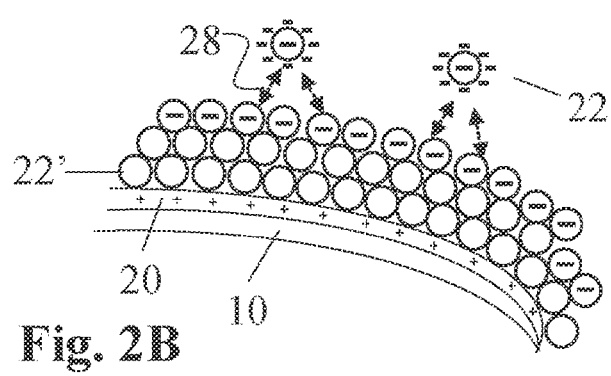
Figure 2C:
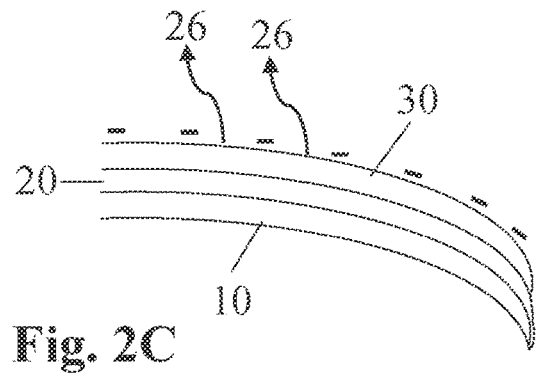
Figure 2D:
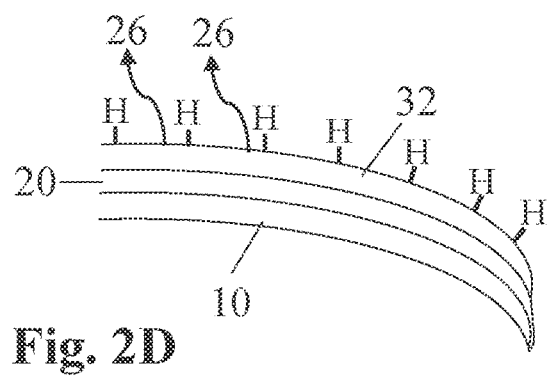
Figure 2E:
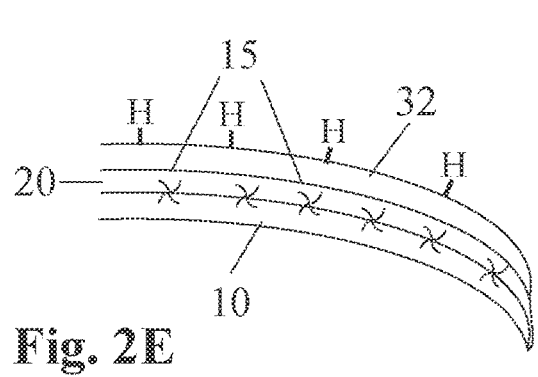
Figure 3A:
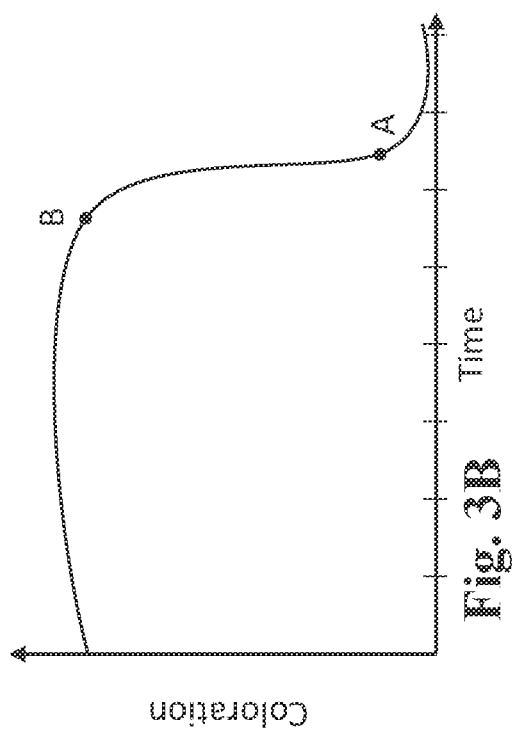
Figure 3B:
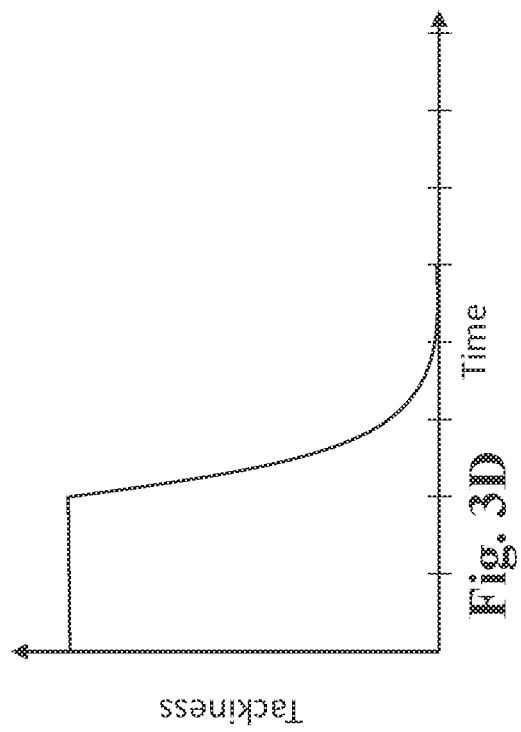
Figure 3C:
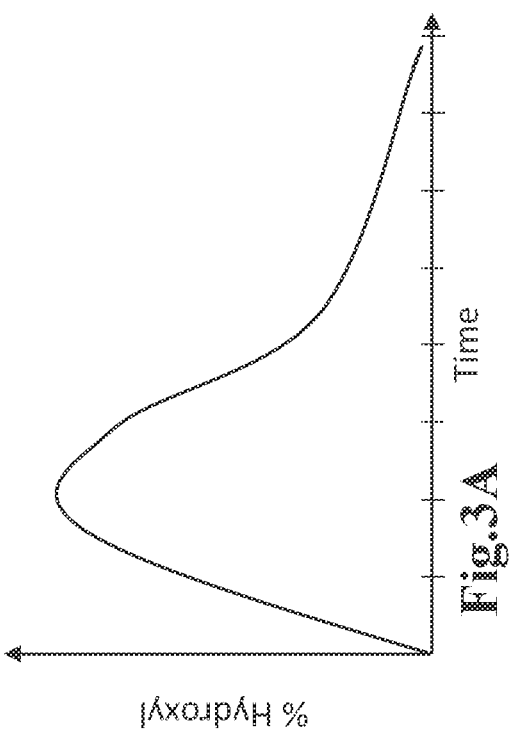
Figure 3D:
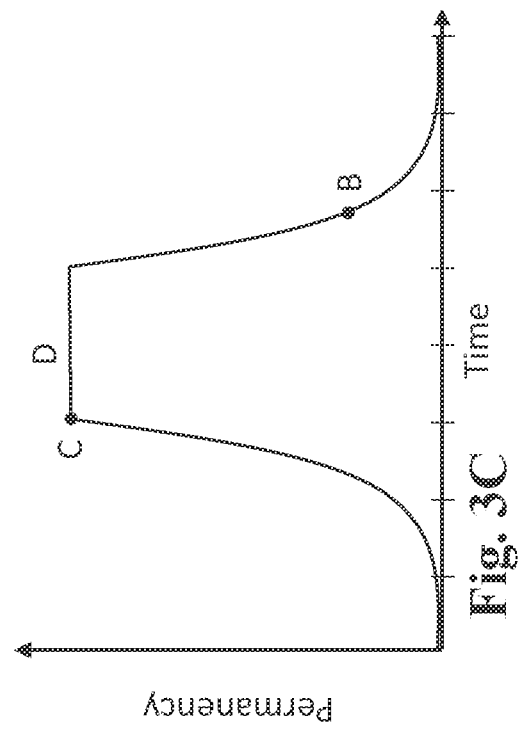
Figure 4:
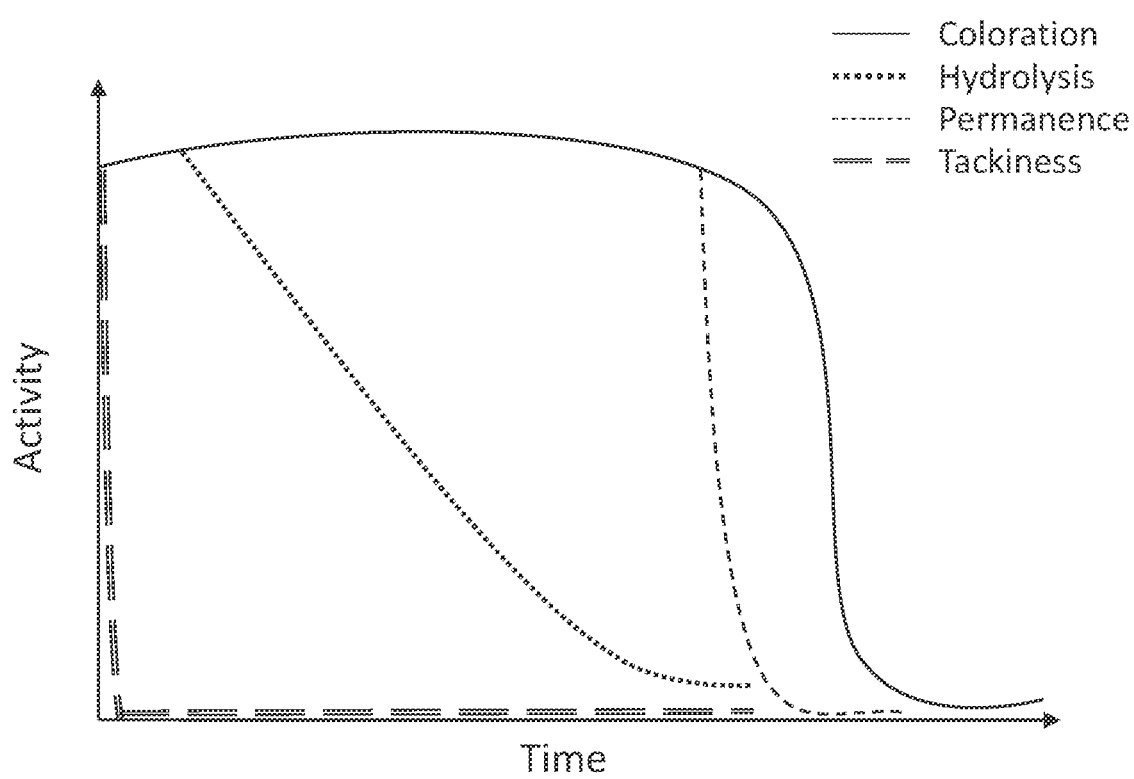
Figure 5:
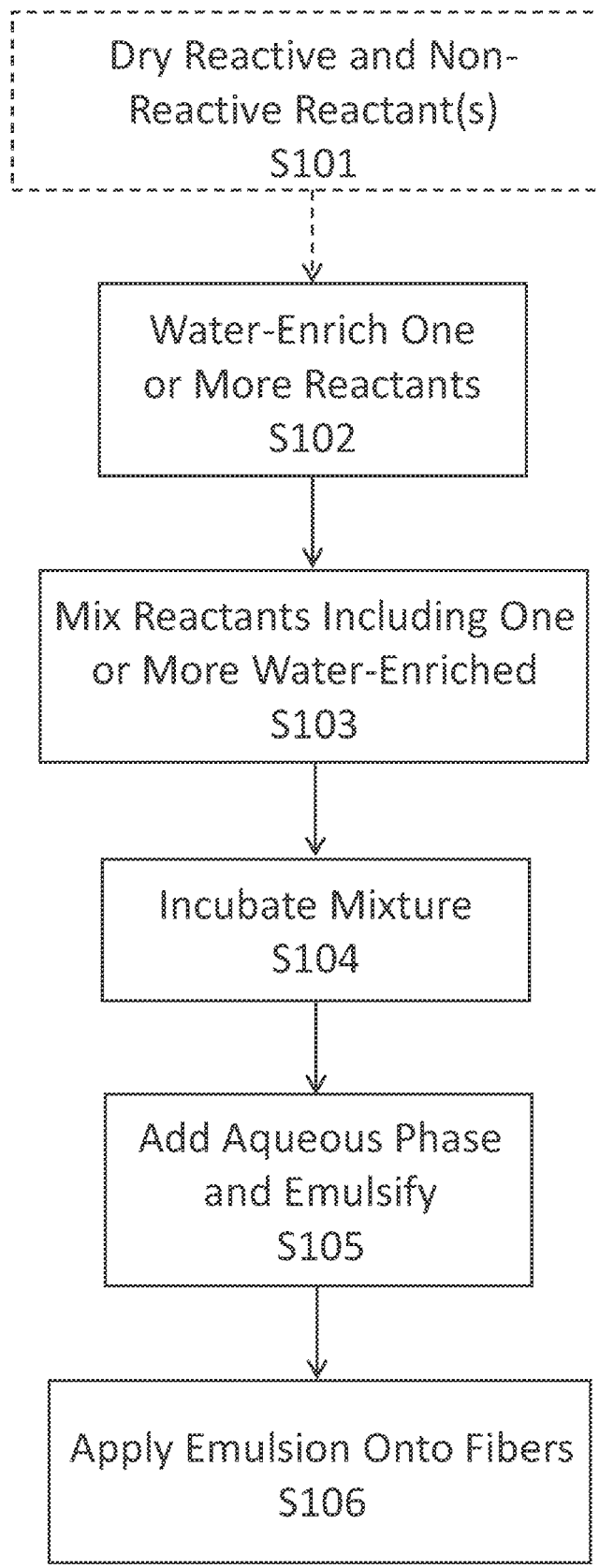

FIG. 1C schematically shows how the emulsion droplets may further accumulate on the external surface of the textile thread;

FIG. 1D schematically shows how the emulsion droplets may coalesce to form a continuous film on the external surface of the textile thread;

FIG. 1E schematically illustrates a top view of the surface of uncoated wool thread, displaying scales, at enlarged magnification;

FIG. 1F schematically illustrates a side view of a longitudinal cross-section through the surface of a coated wool thread, including lifted scales, at enlarged magnification;

FIG. 2A schematically shows how polymeric particles of a neutralized polymer having acid moieties may migrate toward an amino-silicone film on the external surface of the textile thread;

FIG. 2B schematically shows how the polymeric particles may further accumulate on the external surface of the amino-silicone film;

FIG. 2C schematically shows how the polymeric particles may coalesce to form a continuous layer on the external surface of the amino-silicone film;

FIG. 2D schematically shows how a neutralizing agent may evaporate from a polymeric layer modifying the properties of the polymeric material;

FIG. 2E schematically illustrates how the amino-silicone film beneath the polymeric layer can attach to the external surface of an underlying thread;

FIG. 3A is a schematic plot showing the percentage of hydroxyl present in an illustrative pre-treatment composition, as a function of pre-treatment duration of the reactive oil phase;

FIG. 3B is a schematic plot showing the extent of coloration achievable by an illustrative oil-in-water emulsion, as a function of pre-treatment duration of its reactive oil phase;

FIG. 3C is a schematic plot showing the extent of coloration permanence achievable by an illustrative oil-in-water emulsion, as a function of pre-treatment duration of its reactive oil phase;

FIG. 3D is a schematic plot showing the level of tackiness displayed by an illustrative oil-in-water emulsion, as a function of pre-treatment duration of its reactive oil phase;

FIG. 4 is a schematic graph wherein plots similar to FIG. 3A to FIG. 3D are displayed on a single graph, the individual curves representing the extent of hydrolysis, coloration, permanency and tackiness in an improved embodiment; and FIG. 5 depicts a simplified schematic diagram of a method for preparing compositions, including pre-treatment compositions, according to various embodiments of the present teachings.

DETAILED DESCRIPTION

The present disclosure relates to methods for coloring or treating natural keratinous and non-keratinous textile fibers and synthetic textile fibers, and particularly to a method employing oil-in-water emulsions comprising an oil phase including a reactive condensation-curable amino-silicone pre-polymer able to form an amino-silicone coat on the external surface of the textile fibers. The amino silicone coat (also referred to herein as the thermosetting layer, in particular in its cured form) can in turn serve as substrate for aqueous dispersions comprising polymeric particles (including micelles of a hydrophilic polymeric material optionally enveloping pigment particles) being applied in a subsequent step. The present invention is more particularly concerned with a method of pre-treating the oil phase, so as to improve inter alia the performance of the oil-in-water emulsion emulsified therefrom, of the resulting amino-silicone coat and of the subsequent layer of polymeric material (also referred to herein as the thermoplastic layer, in particular in its cured form).

Overview of the Coating Process

Before detailing the pre-treatment method, an overview of the innovative coating or coloring process using a reactive condensation-curing amino-silicone for the formation of a first coat is provided with reference to FIG. 1. For simplicity, the various phases of the process are illustrated on a single side of an isolated textile thread, but may similarly apply to textile fibers in other forms such as a yarn or a fabric, in which case the illustrated shape would correspond to the contour of a normal cross-section of a woven or un-woven fabric. The formation of an amino-silicone coat ("AS coat") on the external surface of the textile thread 10 requires a driving force. Without wishing to be limited by theory, the inventors believe that in various methods of the present invention, the initial driving force for delivering from within the emulsion, the amino-silicone containing reactive-phase droplets 12, to the thread surface, includes, or primarily includes, an electrostatic attraction 14 between negatively-charged functional groups (e.g., hydroxyl, carboxylic) disposed on the external surface of the thread (above the isoelectric pH) and positively-charged functional amine groups in the amino-silicone containing, reactive-phase droplets. This electrostatic attraction is shown schematically in FIG. 1A. Such drive can also be assessed by the gap in surface energy of the wetting liquid and the wetted surface Amino-silicones having a surface energy of no more than the surface energy of the substrate are deemed advantageous. For instance, polyester fibers typically have a surface energy of 40-45 milliNewton/meter (mN/m; also referred to as dyn/cm), and the surface energy of cotton fibers is usually in the range of 70-75 mN/m. The amino-silicones of the present teachings have a surface energy of 24-28 mN/m, which, therefore, allows the wetting of the textile fibers by the amino-silicones.

The inventors believe that after the reactive-phase droplets, which are hydrophobic, reach the thread surface, the droplets displace any water or air disposed thereon, as schematically provided in FIG. 1B by arrow 16, and that some of the positively-charged functional amine groups in the amino-silicone species are drawn sufficiently close to link or otherwise associate with some of the negatively-charged functional groups disposed on the thread surface (see FIG. 1B).

Within a short period of time, typically up to a few minutes, an initial amino-silicone film forms on the thread surface, having an exemplary thickness of approximately 500 nanometers (and typically within a range of 100 nm-2,000 nm). The film may advantageously be self-terminating. Without wishing to be limited by theory, the inventors believe that following the formation of the initial amino-silicone monolayer, successive amino-silicone-containing droplets continue to be attracted by the negative charge of the thread surface, even "through" the first (and interceding) layer 12' of the amino-silicone, but are repelled by the positive charge of the amine-based moieties therein. Initially, the net force of attraction vs. repulsion is positive, such that amino-silicone-containing droplets continue to be attracted towards the thread surface, where the amino-silicone builds up as illustrated in FIG. 1C. This build-up of amino-silicone on the thread is electrostatically driven to continue as long as the net force of attraction vs. repulsion remains positive.

As the thickness of this aggregation increases, the negatively-charged textile thread surface is distanced from the positively-charged droplets disposed in the bulk, at or near the aggregated amino-silicone, diminishing the attractive forces thereon. In addition, the overall positive charge of the amino-silicone aggregation increases with increasing mass of the aggregation, such that the repelling forces continue to increase. After the net force approaches zero, there is substantially no net flux of amino-silicone-containing droplets to the thread surface, such that self-termination has been effected. A self-terminated, positively-charged amino-silicone aggregation disposed on the negatively-charged thread surface is schematically shown in FIG. 1C. The film is self-terminated as soon as the migration of the charged species reach a point where repulsion between the stationary layer on the textile thread and the droplets of the bulk overcomes previous attraction. In other words, when self-termination is achieved no more material can accumulate on the textile thread.

This self-termination of the process, once there is no longer a driving gradient, advantageously prevents an endless build-up of material that conventionally lead to uncontrolled thickness of coatings. In extreme cases, the endless deposition of materials builds-up inseparable lumps of textile of no practical use. In more tolerable situations, while the build-up of materials cannot be prevented, the coating can be interrupted and the textile threads which have been liquid bridged in this undesired process can be individualized and untangled by mechanical means, typically resulting in a poor appearance and/or weakened mechanical resistance/attachment of a color coating, if any. Advantageously, the self-terminating process according to the present teachings results in a coating of reasonable thickness, which allows the coated threads to remain separate and not stuck together. The thickness of the coat can be controlled via the size of the droplets of the emulsion (e.g., droplets having a $D_V50$ of 1-2 μm, as readily formed by vigorous manual shaking, will yield a coat of 0.5-1 μm thickness).

Over time, the amino-silicone aggregation enveloping the textile thread surface undergoes coalescence to form the AS film or coat (FIG. 1D).

According to some embodiments, the reactive condensation-curable amino-functional silicone pre-polymer forms, when in emulsion, emulsion droplets having an average size ($D_V50$) in the range of 200 nm to 100 μm, 200 nm to 50 μm, 200 nm to 25 μm, or from 1 μm to 20 μm, or from 200 nm to 1 μm, or from 0.5 μm to 5 μm, or from 0.7 μm to 3 μm, or from 1 μm to 2.5 μm, or from 1 μm to 10 μm. The size of the droplets and/or the size homogeneity of the population of the droplets can be modified by selecting any desired emulsification method, modulating for instance the energy invested in the process and its duration. Low energy processes (e.g., shaking the mixture manually) may suffice to provide droplets in the 1-5 μm range, which may be heterogeneous in size. Medium energy processes (e.g., using a planetary centrifugal mill) may provide a more homogeneous population, the size of which can be modulated by duration and speed (e.g., providing droplets in the 10-20 μm range, if brief). High energy processes (e.g., using a sonicator) may rapidly provide droplets in the sub-micron range.

Advantageously, as the textile fibers wetted by the positively-charged coat of amino-silicone are repulsing one another, there can be no liquid bridges between adjacent fibers, hence cluster of textile fibers stuck together are prevented. When the partial condensation curing is sufficiently rapid, the outermost layer of the amino-silicone coat can be solid enough prior to drying (forming a crust-like barrier), preventing clumps from forming.

Without wishing to be bound by theory, it is believed that pre-polymers having a relatively low molecular weight (MW), and therefore a relatively low viscosity, have a better prospect to sufficiently wet the textile fibers than a pre-polymer having a relatively higher MW (a relatively higher viscosity). Hence, once the composition constituents are driven to be in sufficient proximity to the textile fibers thanks to electrostatic bonding, additional mechanisms, such as acid:base hydrogen bonding or even covalent bonding, may become available for the attachment of the amino-silicone molecules to the textile fibers' surface. Such processes, in combination with the ongoing condensation curing of the pre-polymer molecules are believed to provide (a) attachment ("adhesivity") to the underlying fibers and (b) "cohesivity" of the amino-silicone film.

While not shown in the figure, pigment particles optionally applied in combination with amino-silicone compositions according to the present invention are advantageously entrapped within the growing network of the pre-polymers, the curing of which is completed in situ on the textile fibers. Such entrapment is believed to improve the attachment of pigment particles to the textile fibers and to ensure their retention thereon for a longer time period than affordable by mere physical deposition in presence of non-reactive polymers. When a pigment dispersant is used in a separate preliminary step to size reduce and/or disperse the pigment into particles, the pigment particles are believed to be first partially enveloped by the pigment dispersant, which in turn forms the interface with the surrounding amino-silicone matrix. In such case, a pre-treatment is preferably applied to the pigment dispersant, rather than to the pigment particles. Moreover, the pre-treatment of the pigment dispersant is preferably performed following the dispersion of the pigment.

While not shown in the figure, it is believed that the amino-silicone film 20 formed according to the above described exemplary embodiment would be positively charged (e.g., under basic pH permitting the protonation of the amine moieties).

The inventors have surprisingly discovered that applying an AS formulation (e.g., an oil-in-water emulsion) having a basic pH (at least 9.0, at least 9.5 or at least 9.75, and typically 9.0-11.5, 9.0-11.0, 9.5-11.5, 9.5-11.0, or 9.5-10.7) may appreciably enhance the adhesion of the AS film to the textile fibers' surface. Without wishing to be limited by theory, considering keratinous textile fibers, the inventors believe that at such a basic pH, the cuticle scales 30 of the fibers on the external surface of the textile thread 10 (as schematically illustrated in a top view, in FIG. 1E) open up. This allows some of the amino-silicone to contact the area "beneath" the opened cuticle scales 30 (FIG. 1F, not drawn to scale). Subsequently, after the pH is reduced (e.g., by evaporation of the volatile carrier modifying the extent of protonation), the cuticle scales of the keratinous textile fibers return to their normally closed, overlapping configuration, thereby mechanically trapping or holding portions of the amino-silicone film 20, and strengthening the amino-silicone film adhesion. Such mechanically trapping of the amino-silicone film may be termed "mechanical macro-adhesion" or simply "macro-adhesion".

It is further believed that such basic pH of an oil-in-water emulsion further increases the difference of charge between the textile fibers being coated and the droplets of reactive amino-silicone pre-polymers. At basic pH, the pre-polymers of the composition (cationic as per their amine functions) are positively charged, while the surface of the textile fibers is negatively charged at a similar pH. Understandingly, according to these principles, anionic and nonionic polymers would not be subjected to such an electrostatic drive towards textile fibers, their prospective attachment therewith, if any, being accordingly reduced (e.g., allowing at most physical deposition or hydrophobic:hydrophobic interactions).

While the electrostatic attraction may be cardinal to enabling the initial adhesion of the film, the inventors have discovered that there may exist appreciable additional hurdles that must be overcome in order for this initial attraction to establish adhesion, and subsequently, for this adhesion to be maintained and strengthened.

One such hurdle pertains to the transport of the species containing the interacting moiety (e.g., an amino or silanol moiety) to the interface with the outer surface of the textile fibers. The inventors have discovered that such transport may be strongly affected, or controlled by, the degree to which the textile fibers are wetted by the amino-silicone containing, reactive-phase droplets within the emulsion. More specifically, the surface tension of this reactive phase is preferably controlled such that this liquid phase amply wets the hydrophobic surface of the textile fibers. The inventors have further discovered that, in some embodiments, the viscosity of the formulation, and more particularly, the viscosity of the reactive phase, should preferably be sufficiently low to facilitate the transport of such species to the textile fibers' surface.

The inventors believe that the various advantages of utilizing viscous polymeric materials notwithstanding, such materials may be significantly less suitable for achieving permanent textile coloring, with respect to their less viscous, monomeric and/or oligomeric counterparts.

Moreover, the inventors have found that even if all of these conditions are satisfied, the electrostatic attraction between the negatively-charged functional groups disposed on the textile fibers' surface and the positively-charged functional amine groups that have been transported to the fibers' surface, along with any other attractive interactions, may be insufficient to overcome various types of steric hindrance. For example, large polymeric structures may not suitably maneuver into position on the textile fibers' surface, because of other such structures (even much smaller ones) that have already established a position on the fibers' surface. Even in the absence of such interference, large polymeric structures may not align with the textile fibers' surface in such a way that the electrostatic attractions, which diminish appreciably with increasing distance, fail to draw the polymeric structure closer to the fibers' surface, or fail to achieve any significant or sufficient linkage between the charged functional groups. In some cases, even when such linkages are formed, they may be insufficient to hold the large polymeric structures in place when subjected to shear forces and/or drag forces (e.g., during washing). The large polymeric structures may have very little surface area available (situated sufficiently close) to the textile fibers' surface, further detracting from the ability of the linkage to withstand such shear and drag.

According to some embodiments, the reactive condensation-curable amino-functional silicone pre-polymer has an average molecular weight in the range of from about 100 to about 100,000 g/mol. Typically, a monomer has a MW in the range of from about 100 to about 1,000 g/mol, an oligomer has an average MW in the range of from about 200 to about 2,000 g/mol, and a polymer has an average MW of at least about 2,000 g/mol, and in some embodiments, of at most 50,000 g/mol.

The inventors have found that strength of the initial AS link to the textile fibers may be generally correlated with increasing Amine Number of the one or more amino-silicone species disposed in the reactive phase of the emulsion. Clearly, however, the accessibility of each amine group (e.g., due to steric hindrance and the like) also needs to be considered. The inventors have found that for sufficient electrostatic attraction and/or linkage to the textile fibers to occur, the Amine Number or average (e.g., weight average) Amine Number of these one or more amino-silicone species should be at least 3 or at least 4, and more typically, at least 5, at least 6, at least 8, or at least 10, and/or within a range of 3-200, 5-500, 10-1,000, 10-400, 10-300, or 25-250. While the amino-silicone pre-polymers are predominantly considered when referring to Amine Number, it should be recalled that amino-silicone oils while lacking condensation-cure group may also contribute to the overall and average Amine Number of the reactive oil phase.

The Amine Number of an amino-silicone pre-polymer, of an amino-silicone oil or of any other amino-silicone specie is generally supplied by the manufacturer, but can be independently determined by standard methods, as described for example in ASTM D 2074-07. It can be provided in terms of the volume (in milliliters) of 0.1N HCl needed to neutralize 10 g of the material under study.

According to aspects of the present invention, an aqueous dispersion containing a polymeric material having neutralized acid moieties may be applied to the underlying AS film, so as to produce an overlying polymeric film coating this AS film. In some embodiments, this polymeric material has acid moieties that can be neutralized, including for instance carboxylic acid groups, which by way of non-limiting example, can be found in acrylic and methacrylic acid moieties.

In many embodiments, this polymeric material may include, mainly include, consist essentially of, or consist of a neutralized alkene-acrylic acid copolymer (such as ethylene-acrylic acid (EAA) copolymer), or of a neutralized alkene-methacrylic acid copolymer (such as ethylene-methacrylic acid (EMAA) copolymer), or of a neutralized acrylamide/acrylate (AAA) copolymer. In some embodiments, this polymeric material may include, mainly include, consist essentially of, or consist of an acrylic copolymer having both neutralized acrylic acid and neutralized methacrylic acid moieties.

Such a polymeric layer, which may include pigment particles, may provide the (pigmented) film structure with various advantageous properties, including abrasion resistance, resistance to intercalation of chemical species (such as soap and shampoo), and more.

Moreover, the inventors have discovered that such copolymers may advantageously serve as pigment dispersants, thereby obviating or at least mitigating the need for a dedicated dispersant (for example, as typically necessary when pigments are dispersed in the AS coat). Hence, much more pigment may be loaded within this overlying polymeric film, thereby improving optical density (coloration) for a given film thickness. Such a dedicated dispersant may also detract from the cohesivity of the overlying polymeric film, and/or from the adhesivity of the overlying polymeric film to the underlying AS coat, and/or from the water resistance. Such a dedicated dispersant may also (typically disadvantageously) reduce the softening point temperature and/or the glass transition temperature of the polymeric layer.

The formation of this polymeric layer, on top of and enveloping the AS film, requires a driving force. Without wishing to be limited by theory, the inventors believe that in various methods of the present invention, the initial driving force for delivering, to the external AS surface, the polymeric material having neutralized acid moieties, includes or primarily includes an electrostatic attraction between positively-charged functional amine groups disposed on and within the AS film and negatively-charged functional groups (e.g., carboxylic moieties) in the dispersed polymeric particles 22 within the aqueous dispersion. This electrostatic attraction 24 is shown schematically in FIG. 2A. This electrostatic attraction is enhanced at basic pH. The inventors believe that the dispersed polymeric particles, driven by this electrostatic attraction, reach the AS film surface, where the negatively-charged functional groups near the outer surface of the particles, and facing the AS film, link up with the positively-charged functional amine groups disposed on the external surface of the AS film, so as to envelop the AS film. This outer (with respect to the underlying AS film) polymeric layer may advantageously be self-terminating. Again, without wishing to be limited by theory, the inventors believe that the dispersed, negatively-charged polymeric particles 22 continue to be attracted by the overall positive charge of the AS film, such that multiple layers 22' of the polymeric particles may become associated with the surface of the AS film (see FIG. 2B). However, since polymeric particles in the "bulk" of the dispersion are repelled (see arrows 28 in FIG. 2B) by the negative charge of these polymeric particles, the electrostatically driven build-up of these polymeric particles on the AS film gradually comes to a halt (substantially as explained hereinabove with respect to the AS film), such that the build-up of this polymeric layer is self-terminating. In other words, the formation of the polymeric layer proceeds as long as there is a zeta potential differential between the surface of the AS coating and the layer of polymeric particles accumulating thereon.

Since as above-explained, the coating of the amino-silicone coat by the polymeric particles is believed to be driven in part by their respective charge during the process, an alternative way of describing the threshold conditions favoring the present method relies on the initial surface zeta potential of the materials due to interact with one another. At the pH of the applied aqueous dispersion, the textile fibers pre-coated with the amino-silicone coat have a first surface zeta potential ($\zeta_1$) while the aqueous dispersion has a second zeta potential ($\zeta_2$). The gap between the two values, also termed the zeta potential differential ($\Delta\zeta$) at said pH is defined as $\Delta\zeta=\zeta_1-\zeta_2$, each of $\zeta_1$, $\zeta_2$ and $\Delta\zeta$ being provided in millivolts (mV). In some embodiments, $\Delta\zeta$ is at least 10 mV, at least 15 mV, at least 20 mV, at least 25 mV, at least 30 mV, at least 40 mV, or at least 50 mV. In some embodiments, $\Delta\zeta$ is within a range of 10 to 80 mV, 10 to 70 mV, 10 to 60 mV, 15 to 80 mV, 15 to 70 mV, 15 to 60 mV, 20 to 80 mV, 20 to 70 mV, 20 to 60 mV, 25 to 80 mV, 25 to 70 mV, 25 to 60 mV, 30 to 80 mV, 30 to 70 mV, 30 to 60 mV, 35 to 80 mV, 35 to 70 mV, or 35 to 60 mV. The pH of the aqueous dispersion being within a range of 4 to 11, 4 to 10.5, 4 to 10, 6 to 11, 6 to 10.5, 6 to 10, 7 to 11, 7 to 10.5, or 7 to 10, the first surface zeta potential ($\zeta_1$) of the amino-silicone coat, is greater than zero ($\zeta_1>0$).

The surface zeta potential of a material is typically measured in liquid phase. Zeta potential of a solid coat can be measured using a streaming current detector in a zeta potential analyzer adapted to force a flow of water through a tube wherein the sample is disposed. Results obtained by such method reflect to some degree the zeta potential of same particles in suspension. Vice versa the zeta potential of the amino-silicone oil-in-water emulsion is deemed predictive of the surface zeta potential of the amino-silicone coat resulting therefrom.

The coating of the amino-silicone coat by the overlying polymeric layer is self-terminated once the zeta potential differential ($\Delta\zeta$) between the two surfaces is essentially zero or is zero.

Over time, the aggregation of dispersed polymeric particles on the AS film undergoes coalescence to form the polymeric overcoat 30 schematically provided in FIG. 2C. In parallel, the volatile materials, including the water carrier and a neutralizing agent, evaporate as schematically illustrated by arrows 26.

The post-application waiting time may be at most 10 minutes or at most 5 minutes, and more typically, at most 3 minutes at most 2 minutes, at most 1.5 minutes, or at most 1 minute. The polymeric overcoat may have a thickness of approximately 100-25,000 nm, 100-20,000 nm, 100-15,000 nm, 100-10,000 nm, or 100-5,000 nm, and more typically, 150-2,000 nm, and yet more typically, 150-1,000 nm or 150-600 nm.

As schematically shown, the external surface of this polymeric overcoat, which faces and contacts the bulk of the aqueous dispersion, contains negatively-charged moieties. It may be advantageous to neutralize these moieties on the external surface, e.g., via the volatile base (such as ammonia) typically present in the aqueous dispersion containing a polymeric material having neutralized acid moieties. Such an operation may result in a coat of conjugate acid of the polymeric material (schematically shown as 32 in FIG. 2D) that exhibits improved water resistance and/or improved mechanical properties, particularly after the volatile base has evaporated.

As excess of neutralizing agent is preferably to be avoided, for the sake of a more rapid evaporation leading inter alia to an accelerated acid conjugation of the neutralized moieties of the hydrophilic material back to native hydrophobic polymer, formation of a water-resistant polymeric layer, and the reduction of stickiness. Additionally, an excess of the neutralizing agent (e.g., base) could block the silanol groups of the amino-silicones of the first coat, by hydrogen bonding therewith, limiting the accessibility of such hydroxyl groups to amine moieties of other amino-silicones and consequently delaying condensation-curing of the amino-silicone coat. In other words, excess base in the second coat can inhibit the curing of the first coat.

In order to avoid excess of neutralizing agent, the amount of a particular base to be added to a particular polymeric material (having a specific content of acid moieties) based on the desired degree of neutralization can be estimated. Furthermore, the amount of base in the neutralized dispersion can be monitored. For instance, it can be monitored by way of pH using a pH meter. In one embodiment, the amount of neutralizing agent in the neutralized dispersion was monitored by conductivity. Base is added, or the dispersion is left to evaporate until a conductivity of less than 3 milliSiemens is reached.

It may be desirable to produce one or more additional coats on top of the above-described overcoat polymeric layer. Addition of another amino-silicone containing formulation (typically emulsion). In basic medium, this neutralizes the acid groups on the external surface of the polymeric overcoat to form negatively-charged moieties, such that the positively-charged amine moieties may be electrostatically attracted to, and subsequently linked to, these negatively-charged moieties.

Over the long term (e.g., 12 to 36 hours, unless particular pre-treatment), additional bonding between the textile fibers and the amino-silicone film may advantageously ensue. FIG. 2E provides a schematic, cross-sectional view illustration of a textile thread 10 having an amino-silicone film 20 covalently bonded 15 thereto, the amino-silicone coat being further enveloped by the polymeric over coat 30.

A polymer (or a film formed from reactive pre-polymers) is believed to be fully cured when, for instance, its glass transition temperature no longer changes over time, in other words has reached a substantially stable value, suggesting that no further cross-linking is taking place. Alternatively and additionally, an amino-silicone polymer (or film resulting therefrom) would be fully cured, when the number of siloxane bonds the pre-polymer can form in the curable fluid and under the curing conditions applicable, does not substantially change over time. The number of siloxane bonds in a cured amino-silicone polymer can be assessed by routine analytical methods, such as by Fourier transform infrared (FTIR) spectroscopy.

The Amino-Silicone Coat

In the following, unless otherwise clear from context, an oil phase or a reactive oil phase (and like variants) encompasses or relates to a reactive oil phase pre-treated according to the present teachings. Similarly, a (reactive) amino-silicone oil-in-water emulsion encompasses or relates to an emulsion, the oil phase of which was pre-treated according to the present teachings.

Pre-polymers generally refer to materials (e.g., uncured/curable monomers, oligomers and/or polymers) that can be cross-linked to form larger macro molecules through cross-linkable groups, also termed reactive groups, by techniques known as curing processes. As used herein, the pre-polymers are deemed reactive (being still able to participate in polymerization or curing) when they lack a glass transition (Tg) temperature (when initially in oil phase). A variety of curing processes exist depending on the chemical composition of the pre-polymers to be cross-linked, their reactive groups and the curing auxiliary factors (cross-linkers, curing accelerators or catalysts, and the like).

While reactive amino-silicone pre-polymers lack an initial Tg, once introduced to the emulsion and applied on the textile fibers and following sufficient curing, a network forms and for the at least partially cured amino-silicone film to behave as a flexible elastomer, lacking brittleness, the pre-polymers preferably cure to form a 3D network having a Tg below about 25° C., namely having a Tg between −100° C. and +20° C., the Tg often not exceeding +15° C., +10° C., +5° C., or 0° C., being possibly below −5° C., below −15° C., or below −25° C.; and optionally in the range between −80° C. and +15° C., between −60° C. and +10° C., between −40° C. and +5° C., between −20° C. and +5° C., between −80° C. and −20° C., or between −70° C. and −30° C.

However, brittleness can also be avoided by using very thin coats (e.g., of one micron or less thickness). In such a case, films of cured polymers having a Tg above about 25° C. can also be used. Cured films having a relatively high Tg have a higher cross-linking density than cured films having a comparatively lower Tg. Cured films having a higher Tg/cross-linking density are expected to be more resistant to abrasion, swelling or chemical attacks (e.g., resistant to alcohols).

Typically, the condensation-curable amino-silicone pre-polymers form a phase separate from water, being substantially non-miscible therewith. Such a distinct phase may also be referred to as an "oil phase", a reactive oil phase or the like variants. For reasons to be further detailed in the following, the reactive oil phase may, in some embodiments, further include, in addition to the reactive amino-silicone pre-polymers, at least one of a silicone oil, an amino-silicone oil, a cross-linking agent, a 3D-network former, pigment particles and a pigment dispersant. All materials present in the oil phase can be termed "reactants", even if lacking any particular ability to react or interact with other molecules of the oil phase.

The present disclosure is concerned with silicone pre-polymers being condensation-curable, namely bearing cross-linkable groups able to react with one another so as to form by condensation a siloxane bond, while liberating in the process a molecule of alcohol, oxime or water. While a variety of condensation-curable reactive groups exist, they can be for ease classified into silanol groups and hydrolysable groups (e.g., alkoxy groups) which upon hydrolysis form silanol groups. Condensation-curable amino-silicone pre-polymers can be classified not only by the chemical identity of their reactive groups, but also by the number of reactive groups per molecule. For simplicity, condensation-curable amino-silicone pre-polymer having a single reactive group per molecule, whether a silanol or a hydrolysable group, can be indicated as 1-SiOH, a molecule having two reactive groups as 2-SiOH and a molecule having three or more reactive groups as 3+SiOH. Condensation-curable amino-silicone pre-polymers having two groups or more may have different groups for each reactive moiety.

While condensation-curable amino-silicone pre-polymers having a single reactive group (1-SiOH) can participate in polymerization (curing) via their unique condensation-cure group, they are generally considered as terminating such process, as far as network progression is concerned. Therefore, when a three-dimensional (3D) network of an amino-silicone film is desired, the presence of condensation-curable amino-silicone pre-polymers having a single condensation-cure reactive group per molecule in a mixture of pre-polymers should remain low and preferably be avoided. The same principle similarly applies to any other material present in the oil phase. Preferably, no reactant should act in a manner equivalent to polymerization termination or curing inhibition. In some embodiments, the concentration of amino-silicone pre-polymers having a single condensation-cure reactive group per molecule and/or of any reactant capable of inhibiting curing is at most 7 wt. %, at most 5 wt. %, at most 2 wt. %, or at most 1 wt. % by weight of the oil phase. In some embodiments, the oil phase is devoid of said 1-SiOH pre-polymer or terminating reactant.

Amino-silicone pre-polymers having two condensation-cure reactive groups per molecule (2-SiOH) can participate in network formation in a more meaningful manner than previously mentioned 1-SiOH counterparts. Preferably, such a network should not rely exclusively on linear chain extension to enable the formation of a sufficiently cohesive 3D-matrix in-between such chains of pre-polymers undergoing curing. By analogy, a reactant able to interact with two distinct groups (generally, but not exclusively on different molecules) can be termed herein "bi-functional". An example of a bi-functional reactant, not being an amino-silicone pre-polymer, can be a non-amino cross-linking agent. In some embodiments, the concentration of amino-silicone pre-polymers having two condensation-cure reactive groups per molecule and/or of any bi-functional reactant is at most 30 wt. %, at most 20 wt. %, at most 10 wt. %, or at most 5 wt. % by weight of the oil phase. In some embodiments, the oil phase is devoid of said 2-SiOH pre-polymer and/or bi-functional reactant.

A reactive polymer-forming condensation-curable amino-silicone pre-polymer having at least three condensation-cure reactive groups (e.g., three silanol and/or hydrolysable groups) advantageously favors the formation of a 3-dimensional network. Similarly, "tri-functional" reactant accelerating or otherwise enhancing the formation of a 3D-network is preferred over less functionalized counterparts. Examples of such "tri-functional" reactants include some cross-linking agents and reactive fillers. In some embodiments, the polymer-forming amino-silicone first reactant includes at least one reactant and/or 3D-network former having at least three condensation-cure reactive groups per molecule.

Condensation-curable amino functional silicones are further characterized by the presence of amino groups attached via carbon atoms to the backbone of the silicone pre-polymers. These amino groups (on terminal or side chains) are further capable of attaching to or interacting with other molecules through nucleophilic reactions or interactions (for example, but not limited, on carboxylic, anhydride or epoxy functional molecules or substrates). Therefore, while some of the silicone pre-polymers disclosed herein are termed "reactive" or "condensation-curable" amino functional silicones, this terminology is not intended to be limiting the curing process exclusively through condensation of the condensation-cure reactive groups, the amino groups being capable of curing also through "non-condensation" processes, such as resulting in the formation of nitrogen-carbon bonding. The products of such curing processes are networks of cross-linked oligomers or polymers termed elastomers or elastomeric networks (rubber like), in reference to their viscoelastic properties. While elastomers generally refer to cured polymers having a glass transition temperature below typical ambient values, thin coats of "elastomeric" polymers having a Tg above such ambient values, and behaving for all practical purposes as formal elastomers, can be tolerated. Thus, as the cured amino-silicone coats resulting from the present methods are thin, both elastomers (e.g., having a Tg<30° C.) and elastomeric networks (e.g., having a Tg>30° C.) are suitable. As such cured networks (preferably three-dimensional to enhance cohesivity) may form a continuous film, the pre-polymers participating in such formation, alone or in combination with additional film-forming agents (e.g., cross-linkers, 3D-network formers), can also be termed film-forming pre-polymers.

The amino functional silicone pre-polymers of the present disclosure (alternatively referred to as "amino-silicone(s)"), may be considered as positively charged or positively chargeable under suitable chemical environment (e.g., at pH above the isoelectric point of the textile fibers). The charge of a particular material can be deduced from its chemical structure and the types of protonation it can undergo. It can be assessed when the material is dispersed or dissolved in water or any other aqueous environment of relevance to the operative conditions of the material under study. In the present case, the amino-silicone pre-polymers are used (alone or in combination with other reactants) in the form of an oil-in-water emulsion.

In some embodiments, the said oil-in-water emulsion has a surface zeta potential greater than zero, or at least +1 mV, at least +2 mV, at least +3 mV, at least +5 mV, at least +7 mV, at least +10 mV, at least +15 mV, at least +20 mV, at least +30 mV, at least +40 mV, or at least +60 mV; optionally, at most +100 mV, or at most +80 mV.

In some embodiments, the oil-in-water emulsion has a surface zeta potential greater than zero and below 90 mV, or within a range of 1-50 mV, 1-30 mV, 1-20 mV, 1-15 mV, 2-100 mV, 2-30 mV, 3-100 mV, 3-50 mV, 3-30 mV, 3-20 mV, 5-100 mV, 5-50 mV, 5-30 mV, 5-20 mV, 7-100 mV, 10-80 mV, 15-80 mV, 20-80 mV, or 20-60 mV.

In some embodiments, the surface zeta potential of the oil-in-water emulsion is measured at a pH of 9. In other embodiments, the surface zeta potential is measured at a native pH of said oil-in-water emulsion (circa pH 10). If the oil-in-water emulsion has too high a solid content, the zeta potential can be determined on a diluted sample comprising 2 wt. % or less of materials on a solid basis.

Such materials can in part be characterized by their Amine Number, indicative of the amount of amino groups per molecule (or per a given weight of an amino-silicone material, whether or not film-forming). In some embodiments, at least one of, and optionally all of the reactive condensation-curable film-forming amino-silicone pre-polymers disposed in the reactive oil phase, has an Amine Number or weight average Amine Number in a range of 3-1,000, 3-500 or 3-200. In some embodiments, the entire reactive oil phase displays an Amine Number in a range of 3-1,000, 3-500 or 3-200.

In some embodiments, the condensation-curable amino-silicone pre-polymer is insoluble or substantially insoluble in water, in which case the pre-polymer can also be said to be hydrophobic. In some embodiments, the solubility of the pre-polymer is of 5 wt. % or less, 2 wt. % or less, 1 wt. % or less, 0.5 wt. % or less, or 0.1 wt. % or less, with respect to the weight of the aqueous composition wherein it is disposed. Solubility can be assessed by the naked eye, the composition being typically at 23° C. A material is water-soluble at or below a threshold concentration, if forming a clear solution in water. When the material is a large macromolecule, such as a polymer, the polymer is said to be water soluble if the micelles formed therefrom are undetectable, the water carrier remaining clear. Conversely, the material (or the pre-polymer) is insoluble if not water-soluble (e.g., forming a visually detectable dispersion or emulsion).

In some embodiments, the reactive condensation-curable film-forming amino-silicone pre-polymer has at least three condensation-cure reactive groups per molecule and has a solubility in water of less than 1 wt. % by weight at 23° C. In some embodiments, the reactive condensation-curable film-forming amino-silicone pre-polymer having at least three condensation-cure reactive groups per molecule includes a reactive condensation-curable amino-silicone monomer having a solubility in water of less than 1 wt. % by weight at 23° C.

As mentioned, the amino-silicone pre-polymers used in the present compositions and methods are reactive and condensation-curable. While the presence or absence of a glass transition temperature allows assessing the reactive potential of a material or a mixture, the viscosity may provide an alternative indication, typically more readily available or assessable. Amino-silicone materials having a relatively high viscosity, and in particular materials being solid at the temperatures of relevance to the performance of the present methods (e.g., at ambient temperature circa 23° C.) are significantly or fully cross-linked. Even if not fully cross-linked, amino-silicones having too high a viscosity are deemed unable to participate in further cross-linking, under conditions (e.g., temperature, time-frame, etc.) of relevance to the present method. For similar reasons, amino-silicone materials having a relatively high molecular weight (MW), which in the case of polymers generally refer to the weight average molecular weight of the material in view of some possible heterogeneity, may also be less reactive or more slowly cured than amino-silicone pre-polymers having relatively lower MW.

The molecular weight of an amino-silicone pre-polymer can depend on the number of same or different repeating units within the pre-polymer. A pre-polymer having a single unit is a monomer. A pre-polymer having a few repeating units is an oligomer. Larger pre-polymers may be defined as polymers. The three main classes of pre-polymer can be distinguished by chemical structure or arbitrarily by molecular weight, when chemical information is missing. The molecular weights or weight average MW of materials are generally provided by the manufacturer, but can be independently determined by known analytical methods, including for instance gel permeation chromatography, high pressure liquid chromatography (HPLC) or matrix-assisted laser desorption/ionization time-of-flight mass spectroscopy MALDI-TOF MS.

In some embodiments, the amino-silicone pre-polymer(s) consists or consists essentially of amino-silicone monomer(s), including mixture thereof. Amino-silicone monomers are able to condensation-cure more rapidly than their oligomer or polymer counterparts, in view of their smaller size/higher accessibility to reactive groups. Such monomers can form three-dimensional (3D) network with high cross-linking density. In some embodiments, when the amino-silicone pre-polymers are predominantly monomers, the reactive oil phase can further include silicone oils and/or amino-silicone oils.

In some embodiments, the condensation-curable amino-silicone monomer(s) has an Amine Number of at least 200, at least 220, at least 240, at least 275, at least 325, or at least 400. In some embodiments, the amino-silicone monomer(s) has an Amine Number of at most 1,500, at most 1,250, at most 1,150, at most 1,050, or at most 1,000. In some embodiments, the amino-silicone monomer(s) has an Amine Number within a range of 200 to 1,500, 220 to 1,250, 200 to 1,250, 200 to 1,150, 200 to 1,100, 220 to 1,250, or 220 to 1,150.

In some embodiments, the amino-silicone pre-polymer(s) consists or consists essentially of amino-silicone oligomer(s), including mixture thereof. Amino-silicone oligomers are able to condensation-cure more rapidly than polymer counterparts, while providing a more flexible coat than sole monomers. Such oligomers can form 3D networks with cross-linking lower than monomers and higher than polymers. In some embodiments, when the amino-silicone pre-polymers are predominantly oligomers, the reactive oil phase can further include silicone oils, amino-silicone oils, non-amino cross-linking agents and/or reactive fillers.

In some embodiments, the condensation-curable amino-silicone oligomer(s) has an Amine Number of at least 20, at least 40, at least 60, at least 75, at least 85, at least 100, at least 125, at least 150, at least 200, or at least 250. In some embodiments, the amino-silicone oligomer(s) has an Amine Number of at most 600, at most 500, at most 450, or at most 400. In some embodiments, the amino-silicone oligomer(s) has an Amine Number within a range of 20 to 600, 40 to 600, 60 to 500, 60 to 400, or 75 to 500.

In some embodiments, the amino-silicone pre-polymer(s) consists or consists essentially of amino-silicone polymer(s), including mixture thereof. Amino-silicone polymers are able to provide a flexible 3D network with low cross-linking density, as suitable for supple substrates such as textile fibers. In some embodiments, when the amino-silicone pre-polymers are predominantly polymers, the reactive oil phase can further include non-amino cross-linking agents, silicone oils, amino-silicone oils and/or reactive fillers.

In some embodiments, the condensation-curable amino-silicone polymer(s) has an Amine Number of at least 2, at least 5, at least 10, at least 15, at least 25, at least 40, at least 75, at least 100, or at least 125. In some embodiments, the amino-silicone polymer(s) has an Amine Number of at most 200, at most 180, at most 160, or at most 140. In some embodiments, the amino-silicone polymer(s) has an Amine Number within a range of 2 to 200, 5 to 200, 10 to 200, 25 to 200, 5 to 150, or 10 to 135.

The inventors have found that mixing the different types of pre-polymers or mixing at least a particular type of pre-polymer with additional non-reactive silicones allows tailoring the characteristics of a cured film that may result therefrom, by harvesting the advantages of each type, while reducing their respective drawbacks. For instance, while the following observations may depend on the exact chemical compounds of each sub-type, it is generally observed that monomers, if used alone, can result in the formation of too brittle coats, while polymers alone may be too slow to fully cure or result in coats lacking sufficient cohesivity. Hence, in order to reduce brittleness, it may be desired to reduce the extent of cross-linking amongst the pre-polymers. Such effect can be achieved, for instance, by adding larger pre-polymers, usually condensation-curable amino-silicone polymers. Alternatively or additionally, amino-silicone oils and/or non-amino silicone oils may be added. Such molecules can diminish the cross-linking density, alleviating brittleness.

Too much of such large pre-polymers and silicone oils may reduce cross-linking density and may also compromise various mechanical properties of the film or coating. In addition, too much non-amino silicone oils may reduce the positive charge density of the amino groups, detracting from the electrostatic attraction mechanism, and/or weakening or destroying the self-terminating mechanism of the film.

In some embodiments, the amino-silicone pre-polymers consist of a mixture of at least two types of pre-polymers selected from condensation-curable amino-silicone monomers, amino-silicone oligomers and amino-silicone polymers. For instance, the pre-polymer mix can comprise condensation-curable amino-silicone monomers (e.g., for their rapidity to cure), condensation-curable amino-silicone oligomers (e.g., for their ability to control the density of the cross-linking) and condensation-curable amino-silicone polymers (e.g., for their contribution to the coat flexibility).

In some embodiments, the condensation-curable amino-silicone monomers are present in a mixture of pre-polymers in an amount greater than the amount of condensation-curable amino-silicone oligomers. In some embodiments, the condensation-curable amino-silicone monomers are present in an amount greater than the amount of condensation-curable amino-silicone polymers. In some embodiments, the condensation-curable amino-silicone monomers are present in an amount greater than the total amount of condensation-curable amino-silicone oligomers and polymers.

With regards to viscosity, amino-silicone pre-polymers having a relatively low one are not only prospectively more reactive and/or more mobile than more viscous counterparts, they additionally may better wet textile fibers following their application thereon.

In some embodiments, the oil phase, exclusive of all inorganic content, has no glass transition temperature.

In some embodiments, the condensation-curable film-forming amino-silicone pre-polymer is a liquid at 23° C.

According to some embodiments, the reactive condensation-curable amino-silicone pre-polymer satisfies at least one, at least two or at least three of the following structural properties:

a) the pre-polymer includes reactive groups selected from the group consisting of alkoxy-silane reactive groups, silanol reactive groups and combinations thereof;

b) the pre-polymer has no glass transition temperature;

c) the pre-polymer is not solid at 23° C.;

d) the pre-polymer has a viscosity in the range of 1-2,000 milliPascal-second (mPa·s, also referred to as cps), 10-2,000 mPa·s, 2-1,000 mPa·s, 2-500 mPa·s, 5-100 mPa·s, 10-20,000 mPa·s, 10-15,000 mPa·s, 20-15,000 mPa·s, 30-15,000 mPa·s, 40-10,000 mPa·s or 50-10,000 mPa·s as measured at 23° C. in a suitable rheometer;

e) the pre-polymer is capable of wetting said textile fibers;
f) the pre-polymer is a film-forming pre-polymer;
g) the pre-polymer includes a primary amine;
h) the pre-polymer has an Amine Number in the range of 3-1,000, 3-500 or 3-200;
i) the pre-polymer includes terminal amino-moieties;
j) the pre-polymer includes pendant amino-moieties;
k) the pre-polymer is miscible in a reactive oil phase comprising, in addition to the pre-polymer, at least one of a different pre-polymer, a non-reactive silicone oil, a non-reactive amino-silicone oil, a cross-linker and a pigment dispersant;
l) the pre-polymer has a refractive index within ±10% of a refractive index of a reactive oil phase comprising at least one of a different pre-polymer, a non-reactive silicone oil, a non-reactive amino-silicone oil, a cross-linker, a hydrophobic fumed silica and a pigment dispersant;
m) the pre-polymer is hydrophobic;
n) the pre-polymer has a solubility in water (e.g., circa pH 7) at 23° C. of less than 5 wt. % by weight, less than 2 wt. % by weight, less than 1 wt. % by weight, less than 0.5 wt. % by weight, or less than 0.25 wt. % by weight;
o) the pre-polymer is a linear or a branched polymer;
p) the pre-polymer is a linear or a branched oligomer;
q) the pre-polymer is a monomer; and
r) the pre-polymer has a ratio of Amine Number (AN) to viscosity (Visc.) in mPa·s, which when multiplied by 1000, is of at least 40, at least 100, at least 200, or at least 500, which can be mathematically expressed as 1000*(AN/Visc.)≥40, and so on.

While silicone materials solid at 23-25° C. have been disclosed as suitable to improve textile lubricity, when applied as particles, it is readily apparent that such solids are non-reactive and unable to participate in the prospective formation of a continuous layer, as enabled by the coalescence of droplets of silicone materials fluid at same temperature. Solid silicone particles are believed to act as friction reducers in a manner similar to mechanical bearings.

In some embodiments, the pre-polymer has no glass transition temperature and has a solubility in water (pH 7) at 23° C. of less than 1 wt. %, less than 0.5 wt. %, or less than 0.25 wt. % by weight of aqueous composition.

In some embodiments, the pre-polymer has no glass transition temperature and has a viscosity in the range of 1-2,000 mPa·s, 10-2,000 mPa·s, 2-1,000 mPa·s, 2-500 mPa·s, 5-100 mPa·s, 10-20,000 mPa·s, 10-15,000 mPa·s, 20-15,000 mPa·s, 30-15,000 mPa·s, 40-10,000 mPa·s or 50-10,000 mPa·s as measured at 23° C.

In some embodiments, the pre-polymer has no glass transition temperature and has a reactive group selected from the group consisting of alkoxy-silane reactive groups, silanol reactive groups and combinations thereof.

In some embodiments, the pre-polymer has an Amine Number in the range of 3-1,000, 3-500 or 3-200 and has a viscosity in the range of 1-2,000 mPa·s, 10-2,000 mPa·s, 2-1,000 mPa·s, 2-500 mPa·s, 5-100 mPa·s, 10-20,000 mPa·s, 10-15,000 mPa·s, 20-15,000 mPa·s, 30-15,000 mPa·s, 40-10,000 mPa·s or 50-10,000 mPa·s as measured at 23° C.

In some embodiments, the pre-polymer has an Amine Number in the range of 3-1,000, 3-500 or 3-200 and has a solubility in water at 23° C. of less than 1 wt. %, less than 0.5 wt. %, or less than 0.25 wt. % by weight of aqueous composition.

In some embodiments, the pre-polymer has an Amine Number in the range of 3-1,000, 3-500 or 3-200 and is miscible in a reactive oil phase comprising, in addition to the pre-polymer, at least one of a different pre-polymer, a non-reactive silicone oil, a non-reactive amino-silicone oil, a cross-linker and a pigment dispersant.

In some embodiments, the pre-polymer has no glass transition temperature; has a reactive groups selected from the group consisting of alkoxy-silane reactive groups, silanol reactive groups and combinations thereof; and has a viscosity in the range of 1-2,000 mPa·s, 10-2,000 mPa·s, 2-1,000 mPa·s, 2-500 mPa·s, 5-100 mPa·s, 10-20,000 mPa·s, 10-15,000 mPa·s, 20-15,000 mPa·s, 30-15,000 mPa·s, 40-10,000 mPa·s or 50-10,000 mPa·s as measured at 23° C. in a suitable rheometer.

In some embodiments, the pre-polymer has an Amine Number in the range of 3-1,000, 3-500 or 3-200; has a solubility in water at 23° C. of less than 1 wt. %, less than 0.5 wt. %, or less than 0.25 wt. % by weight of aqueous composition; and is miscible in a reactive oil phase comprising, in addition to the pre-polymer, at least one of a different pre-polymer, a non-reactive silicone oil, a non-reactive amino-silicone oil, a cross-linker and a pigment dispersant.

In some embodiments, the pre-polymer has no glass transition temperature; has a reactive groups selected from the group consisting of alkoxy-silane reactive groups, silanol reactive groups and combinations thereof; has a viscosity in the range of 1-2,000 mPa·s, 10-2,000 mPa·s, 2-1,000 mPa·s, 2-500 mPa·s, 5-100 mPa·s, 10-20,000 mPa·s, 10-15,000 mPa·s, 20-15,000 mPa·s, 30-15,000 mPa·s, 40-10,000 mPa·s or 50-10,000 mPa·s as measured at 23° C.; and has an Amine Number in the range of 3-1,000, 3-500 or 3-200.

In some embodiments, the pre-polymer has no glass transition temperature; has a reactive groups selected from the group consisting of alkoxy-silane reactive groups, silanol reactive groups and combinations thereof; has a viscosity in the range of 1-2,000 mPa·s, 10-2,000 mPa·s, 2-1,000 mPa·s, 2-500 mPa·s, 5-100 mPa·s, 10-20,000 mPa·s, 10-15,000 mPa·s, 20-15,000 mPa·s, 30-15,000 mPa·s, 40-10,000 mPa·s or 50-10,000 mPa·s as measured at 23° C.; has an Amine Number in the range of 3-1,000, 3-500 or 3-200; and has a solubility in water at 23° C. of less than 1 wt. %, less than 0.5 wt. %, or less than 0.25 wt. % by weight of aqueous composition.

According to some embodiments, suitable reactive condensation-curable amino-silicone pre-polymers can be selected from the group comprising: ATM 1322, Bis[methyl-diethoxysilyl-propyl] amine, Diethoxydimethylsilane, aminopropyltriethoxysilane, DMS-S12, Dynasylan® SIVO 210, Dynasylan® 1146, KF-857, GP-145, GP-34, GP-397, GP-657, GP-846, KF-862, OFX 8630, OFX 8822, SIB1824.5, SF 1706, Silquest® VX-225, Silquest® Y-15744, SI06629.1, SIT8187.2, TSF 4703, TSF 4707, TSF 4708 and any commercially available equivalent of the foregoing. According to some embodiments, the oil-in-water emulsion (which can be in one formulation or resulting from the combination of sub-formulations) further comprises an oil, miscible with the at least one pre-polymer, and/or miscible with the cross-linking agent, and/or miscible with the condensation-cure accelerator or catalyst, the oil including, but not limited to, a silicone oil.

As textile fibers coated according to the present teachings may serve for the manufacture of fabrics or garments for human use, the ingredients used for the preparation of the compositions applied in the steps of the present method may preferably be compatible for contact with human skin, without undue allergy, hypersensitivity, toxicity, instability, and the like.

In the above, and as further detailed herein, a few properties of an amino-silicone pre-polymer suitable for the present invention were considered for an individual material. However, as a reactive oil phase may comprise more than one amino-silicone pre-polymer and furthermore additional reactant(s), the recommended properties of such mixture shall also be pointed out. The skilled person readily appreciates that while a particular property can be permissible or on the contrary undesirable for an isolated material, mixing the material in an oil phase may provide different tolerances. As the reactants of an oil phase may include solid inorganic particles (e.g., pigment particles, 3D-network formers) which may affect particular measurements, the fact they can be omitted for the sake of particular determinations does not imply that such inorganic particles are absent of a complete oil phase being emulsified for application to textile fibers.

In some embodiments, a reactive oil phase comprising at least one of a condensation-curable amino-silicone pre-polymer, a non-reactive silicone oil, a non-reactive amino-silicone oil, a liquid hydrophobic cross-linker and a pigment dispersant, has no glass transition temperature.

In some embodiments, a reactive oil phase comprising at least one of a condensation-curable amino-silicone pre-polymer, a non-reactive silicone oil, a non-reactive amino-silicone oil, a cross-linker, a reactive filler, a pigment and a pigment dispersant, has a viscosity in the range of 1-2,000 mPa·s, 2-1,000 mPa·s, 2-500 mPa·s, 2-400 mPa·s, 2-300 mPa·s, 2-200 mPa·s, 2-200 mPa·s, or 2-50 mPa·s, as measured at 23° C. in a suitable rheometer.

In some embodiments, a reactive oil phase comprising at least one of a condensation-curable amino-silicone pre-polymer, a non-reactive silicone oil, a non-reactive amino-silicone oil, a liquid hydrophobic cross-linker and a pigment dispersant, has a solubility in water at 23° C. of less than 5 wt. % by weight, less than 2 wt. % by weight, less than 1 wt. % by weight, less than 0.5 wt. % by weight, less than 0.25 wt. % by weight of the total aqueous composition.

When assessing the solubility of an oil phase is desired, but the phase is in emulsified or any other mixed form, the oil can be separated by any suitable method known to the skilled person (e.g., by centrifugation). The oil phase so extracted can then be assessed for any desired property (e.g., solubility, glass transition temperature, chemical analysis), by any appropriate standard method.

As solvents, such as organic solvents, can inter alia modify solubility of materials, such solvents are to be avoided in order to maintain a suitable oil-in-water emulsion and/or a suitable partition of the components of the oil-in-water emulsion between the aqueous and oil phase.

As used herein in the specification and in the claims section that follows, the term "organic solvent" within or with respect to an oil phase, refers to an organic liquid that is disposed within an oil phase containing at least one solute (e.g., a pre-polymer or a reactant), and which organic liquid does not positively participate in the intra-polymer bonding nor in the bonding of an amino-silicone film to the surface of the textile fibers.

As used herein in the specification and in the claims section that follows, the term "co-solvent" within or with respect to an aqueous phase, refers to an organic liquid that is at least partially miscible within an aqueous phase, the organic liquid further characterized in that it increases the solubility, within the aqueous phase, of at least one component that is disposed in the oil phase. Taken to the extreme, water miscible co-solvents may essentially lead to the "solubilization" of the entire oil phase within the aqueous phase.

Organic solvents may include, by way of non-limiting examples, volatile $C_1$-$C_6$ alkanols, such as ethanol; volatile $C_5$-$C_7$ alkanes such as hexane; esters of liquid $C_1$-$C_{20}$ acids and of volatile $C_1$-$C_8$ alcohols such as methyl acetate; volatile ketones that are liquid at room temperature (RT, circa 23° C.), such as acetone; volatile hydrocarbon-based oils, such as $C_8$-$C_{16}$ alkanes, for instance isododecane; volatile ethers or glycol ethers such as dimethoxymethane or diethylene glycol monomethyl ether; and mixtures thereof.

As used herein, "silicone-compatible co-solvents" refers to water-miscible organic solvents in which silicone-based components, such as detailed with reference to the reactive oil phase, are miscible. The presence of such silicone compatible co-solvents in an aqueous phase can therefore lead to the undesired transition of any one of the silicone components from an oil phase to the aqueous phase. Silicone-compatible co-solvents may include, by way of non-limiting examples, volatile $C_1$-$C_6$ alkanols, such as ethanol; esters of liquid $C_1$-$C_{20}$ acids and of volatile $C_1$-$C_8$ alcohols such as methyl acetate; and volatile ketones that are liquid at RT, such as acetone; and mixtures thereof.

It is believed that such solvents, in addition to detracting from the efficacy of an oil phase and/or preventing the formation of an emulsion, may also, if present in the same phase as the condensation-curable amino-silicone pre-polymer, reduce or delay condensation curing.

In some embodiments, the total concentration of organic solvents within the oil phase of the emulsion, on a weight basis, is at most 10 wt. %, at most 5 wt. %, at most 2 wt. %, or at most 1%. In some embodiments, the oil phase is devoid of any organic solvent.

In some embodiments, the total concentration of silicone-compatible co-solvents within the aqueous phase of the emulsion, on a weight basis, is at most 10 wt. %, at most 5 wt. %, at most 2 wt. %, or at most 1 wt. %. In some embodiments, the aqueous phase is devoid of any said co-solvent.

In some embodiments, the total concentration of organic solvents within the oil phase and of silicone-compatible co-solvents within the aqueous phase of the emulsion, is at most 10 wt. %, at most 5 wt. %, at most 2 wt. %, or at most 1 wt. %, by weight of the oil-in-water emulsion. In some embodiments, the oil-in-water emulsion is substantially devoid of an organic solvent and of a silicone-compatible co-solvent.

The oil-in-water emulsions of the present invention are two-phase systems, composed of an oil phase in the form of droplets dispersed in a continuous second phase. The second phase can be water or an aqueous medium, or alternatively, a carrier within which the oil phase remains distinct and immiscible. Such carriers must not be silicone-compatible, thus preventing any undesired transition of silicone compounds from the oil phase into the continuous second phase. Suitable carriers are selected from glycols (either liquid, or solid dissolvable in water), pegylated silicones or silicone polyethers. These carriers can be present as the sole components of the continuous second phase, or in combination with up to 50% water by weight of the continuous second phase, so as to maintain a positive surface zeta potential of the oil-in-water emulsion.

As used herein in the specification and in the claims section that follows, the term "solubility" with respect to a component or mixture of components ("component") and a solvent or solvent mixture ("solvent"), is meant to refer to the solubility of the component in the solvent at the native pH, i.e., at the natural pH attained by adding solely the component to the solvent, in the absence of other components and in the absence of any pH modifiers. In the particular case of water solubility, the definition assumes the water has an initial pH of 7.

Pigments are typically water-insoluble, as opposed to dyes. In some embodiments, the pigment particles optionally dispersed within the reactive oil phase of the emulsion are not soluble therein.

In some embodiments, the concentration of a condensation-curable amino-silicone pre-polymer having 3 or more silanol and/or hydrolysable groups per molecule, within the oil phase, is at least 15 wt. %, at least 20 wt. %, at least 30 wt. %, at least 40 wt. %, at least 50 wt. %, or at least 60 wt. %, by weight, of said oil phase. In some embodiments, the concentration of the 3-SiOH pre-polymer is at most 95 wt. %, at most 90 wt. %, at most 85 wt. %, at most 80 wt. %, at most 75 wt. %, or at most 70 wt. %. In some embodiments, the concentration of the amino-silicone pre-polymer, within the oil phase, is within a range of 20-95 wt. %, 20-85 wt. %, 30-95 wt. %, 30-85 wt. %, 40-95 wt. %, 40-85 wt. %, 40-75 wt. %, 45-95 wt. %, 45-85 wt. %, 50-95 wt. %, 50-85 wt. %, 55-95 wt. %, 55-85 wt. %, 55-75 wt. %, 60-95 wt. %, 60-90 wt. %, 60-85 wt. %, or 60-80 wt. %.

In some embodiments, a non-amino cross-linking agent is present in the oil phase. In such embodiment, a combined concentration of the amino-silicone pre-polymer and the non-amino cross-linking agent, within the oil phase, is within a range of 35-95 wt. %, 40-95 wt. %, 40-85 wt. %, 40-75 wt. %, 45-95 wt. %, 45-85 wt. %, 50-95 wt. %, 50-85 wt. %, 55-95 wt. %, 55-85 wt. %, 55-75 wt. %, 60-95 wt. %, 60-90 wt. %, 60-85 wt. %, or 60-80 wt. %, by weight, of said oil phase.

In some embodiments, a concentration of the non-amino cross-linking agent within the combined concentration is limited by a condition that the oil-in-water emulsion has a surface zeta potential greater than zero (>0), or at least +1 mV, at least +2 mV, at least +3 mV, at least +5 mV, at least +7 mV, or at least +10 mV.

In some embodiments, within the oil phase, a total concentration of an amino-silicone oil, a non-amino-silicone oil and any condensation-curable amino-silicone pre-polymer having less than three condensation-cure reactive group per molecule is within a range of 3 wt. % to 65 wt. %, 3 wt. % to 60 wt. %, 3 wt. % to 55 wt. %, 3 wt. % to 50 wt. %, 3 wt. % to 45 wt. %, 3 wt. % to 40 wt. %, 7 wt. % to 40 wt. %, 10 wt. % to 40 wt. %, 10 wt. % to 50 wt. %, 15 wt. % to 50 wt. %, 15 wt. % to 45 wt. %, 15 wt. % to 40 wt. %, 20 wt. % to 45 wt. %, 25 wt. % to 45 wt. %, 25 wt. % to 50 wt. %, 30 wt. % to 45 wt. %, 30 wt. % to 60 wt. %, 35 wt. % to 50 wt. %, or 35 wt. % to 60 wt. %, by weight. In some embodiments, the total concentration of the afore-said different constituents of the oil phase is subject to the oil phase having a viscosity of no more than 2,000 mPa·s, no more than 500 mPa·s, or no more than 100 mPa·s, as measured at 23° C.

In some embodiments, the oil-in-water emulsion further comprises a solid, hydrophobic reactive inorganic filler, said filler disposed or dispersed within the oil phase, said filler selected or adapted to facilitate curing of the condensation-curable film-forming amino-silicone pre-polymer(s). Such a film reinforcing filler can also be referred to as a reactive filler. Advantageously, the reactive reinforcement filler is a hydrophobic 3D network former contributing to the increase in cohesivity of the amino-silicone film.

Reinforcement fillers can generally be selected from the group of fumed silica, precipitated silica, magnesia, alumina (e.g., $Al_2O_3 \cdot 3H_2O$), black, amorphous, carbon (carbon black, channel black, or lamp black). The reinforcement filler can be selected to suit a particular coloration. For instance, if a reinforcement filler is desired in a relatively high quantity, then black fillers are to be avoided if in a size range that may affect a relatively light shade. Conversely, if a dark shade is desired, then black reinforcement fillers can be advantageous.

Suitable reactive fillers can be selected from hydrophobic fumed silica, the surface of which being at least partially covered by siloxane groups or other groups having a hydrophobic nature, such groups typically reacting with silanol functional units on the silica. Hence, in such cases, the hydrophobic fumed silica can be referred to as a silanol blocked silica, the surface treatment of the fumed silica blocking the silanol functionalities being achieved by one or more of HDMS, poly siloxane, cyclic poly siloxane, silazane, amino silane and silicone oils. The blocking treatment needs not to be complete, some residual silanol groups being permissible and even desirable for ensuring or facilitating at least partial curing. Hydrophobic fumed silica, when present, is typically disposed in the oil phase of the oil-in-water emulsion of condensation-curable silicone.

In some embodiments, the reactive filler includes, mainly includes, or consists of, a hydrophobic fumed silica.

In some embodiments, the average particle size ($D_V 50$) of the solid, hydrophobic reactive inorganic filler is within a range of 5 to 500 nm, 5 to 250 nm, 10 to 200 nm, 20 to 200 nm, 40 to 300 nm, 60 to 300 nm, 60 to 250 nm, or 60 to 200 nm.

In some embodiments, the concentration of the solid, hydrophobic reactive inorganic filler disposed or dispersed within the oil phase is within a range of 0.2 wt. % to 12 wt. %, 0.2 wt. % to 10 wt. %, 0.2 wt. % to 8 wt. %, 0.4 wt. % to 10 wt. %, 0.4 wt. % to 8 wt. %, 0.6 wt. % to 10 wt. %, 0.6 wt. % to 8 wt. %, 0.8 wt. % to 8 wt. %, or 0.8 wt. % to 6 wt. %, by weight of the oil phase. In some embodiments, the concentration of the solid, hydrophobic reactive inorganic filler within the oil-in-water emulsion is within a range of 0.005 wt. % to 0.5 wt. %, 0.005 wt. % to 0.3 wt. %, by weight of the oil-in-water emulsion.

In some embodiments, the refractive index of the solid, hydrophobic reactive inorganic filler, being optionally a fumed silica filler, is within a range of ±10%, ±7%, ±5%, or ±3%, of a refractive index of the oil phase, exclusive of any pigment particles disposed therein.

According to some embodiments, the oil-in-water emulsion, has a pH of at least 4.0, at least 5.5, at least 7.0, at least 8.5, at least 10.0; and optionally of at most 11.0. In some embodiments, the oil-in-water emulsion, has a pH within a range of 4.0 to 12.0, 5.5 to 12.0, 7.0 to 11.0, or 8.5 to 11.0. A pH above the isoelectric point of the textile fibers to be coated enables a negative charging of the fibers and/or a positive charging of amino functions of the amino-silicone pre-polymers. Taking for example cotton fibers, its isoelectric point was reported to be about pH 2.9, while the isoelectric point of wool was reported at a pH of about 4.7, and the isoelectric points of synthetic fibers, such as acrylic or polyester, were reported to be 3 or less than 2.5, respectively. As shall be detailed in the following, a gradient of charge between the surface of textile fibers and the pre-polymers of the composition is expected to permit electrostatic attachment between the two, as a first step in the formation of a coat. In particular embodiments, the oil-inwater emulsion has a basic pH of at least 7.5, at least, 8.0, at least 9.0 or at least 9.5, and of at most 11.0.

The textile fibers' surface shall be negatively charged when using a composition having a pH above the isoelectric point of the fibers (e.g., >4, preferably >7). In some embodiments, the reactive condensation-curable amino-functional silicone pre-polymer is positively charged when dispersed (e.g., emulsified) in a carrier. For instance, amino-silicone pre-polymers can be positively charged as of a pH of 4.0 and until they reach their isoelectric point (typically in the range of pH 10-12). Interestingly, the protonation of the amine groups above the acidic pH (assuming a sufficient concentration) can maintain the composition within the basic pH range even in absence of a dedicated pH buffering agent. It is to be noted, for keratinous textile fibers that at a relatively high pH (>9), the keratinous fibers' scales are sufficiently charged to repulse one another, resulting in the opening of the channels leading to the fibers' shafts. The lifting of the scales increases the surface area of the fibers, enhancing contact surface with the emulsion of reactive amino-silicone pre-polymers. As carrier evaporates, the pH of the coat gradually decreases, and the scales return to their original positions, possibly entrapping in the process a portion of the amino-silicone film, furthering its adherence to the keratinous textile fibers by mechanical interlocking.

According to some embodiments, the oil-in-water emulsion is applied on the textile fibers for sufficient time for such a gradient to drive enough droplets to wet and form a continuous coat on the fibers. In one embodiment, the application time is between 5 seconds and 60 minutes, or between 5 seconds and 30 minutes, or between 5 seconds and 10 minutes, or between 10 seconds and 2 minutes, or of 1 minute or less. According to some embodiments, the duration of time enabling the partial curing is between 5 seconds and 30 minutes, or between 1 minute and 15 minutes. While partial curing may initiate at the time of application of the oil-in-water emulsion, it can also proceed once excess of the emulsion is removed (e.g., before rinsing the textile fibers).

In some embodiments, the at least partially cured film is self-terminated on the external surface of the textile fibers.

In some embodiments, the partial condensation curing is effected or transpires at a temperature of at most 75° C., at most 65° C., at most 55° C., at most 45° C., at most 38° C., at most 36° C., at most 34° C., at most 32° C., at most 30° C., or at most 28° C., and optionally, at least 15° C. In some embodiments, the partial condensation curing is effected or transpires at a temperature within the range of 15° C. to 75° C., 15° C. to 65° C., 20° C. to 55° C., or 20° C. to 45° C.

The maximal curing temperature can be determined according to the heat sensitivity of the most sensitive of the components of the amino-silicone emulsion, hence if the composition includes an ingredient which could decompose above a temperature of about 75° C., the partial condensation curing shall be performed at a lower temperature.

In some embodiments, the washing of the textile fibers is performed within 30 minutes, within 20 minutes, within 15 minutes, within 10 minutes, within 5 minutes, within 3 minutes, within 2 minutes, or within 1 minute, after the application of the oil-in-water emulsion has been completed.

In some embodiments, following the washing, further curing transpires solely by or substantially solely by humidity or ambient humidity.

In some embodiments, within at least half-a-day, within at least one day, within at least two days, at least three days, at least five days, or at least a week of said washing, all further curing proceeds in the absence of any non-cationic surfactant added to the textile fibers.

In some embodiments, within at least half-a-day, within at least one day, within at least two days, at least three days, at least five days, or at least a week of the washing, treating the textile fibers can be performed with a textile formulation containing a cationic surfactant.

In some embodiments, the rinsing liquid is (i) water, or (ii) a cationic rinsing liquid containing a cationic surfactant, or (iii) a rinsing liquid devoid of non-cationic surfactants, degreasing agents and/or swelling agents, the degreasing and swelling agent respectively able to degrease and swell the at least partially cured film.

In some embodiments, the cationic surfactant is a primary, secondary, tertiary, or quaternary ammonium compound or polymer.

In some embodiments, the total concentration of reactive condensation-curable amino-silicone components within the oil phase is at least 45 wt. %, at least 55 wt. %, at least 60 wt. %, or at least 65 wt. %, by weight of the oil phase, on a pigment-less basis. In some embodiments, the total concentration of reactive components within a range of 50-100 wt. %, 50-95 wt. %, 50-90 wt. %, 50-85 wt. %, 50-80 wt. %, 55-95 wt. %, 55-85 wt. %, 60-95 wt. %, 60-85 wt. %, 65-95 wt. %, 65-90 wt. %, or 70-95 wt. %.

In some embodiments, the amino-silicone pre-polymer includes reactive groups selected from the group consisting of alkoxy-silane reactive groups, silanol reactive groups and combinations thereof.

In some embodiments, the solubility in water of the at least one reactive condensation-curable film-forming amino-silicone pre-polymer, by weight, is less than 0.5 wt. % or less than 0.25 wt. %.

In some embodiments, the total concentration of amino-silicone oil within the oil phase, by weight, is at most 40 wt. %, at most 35 wt. %, at most 30 wt. %, at most 20 wt. %, at most 15 wt. %, at most 10 wt. %, or at most 5 wt. %.

In some embodiments, the total concentration of amino-silicone oil within the oil phase, by weight, is within a range of 1 wt. % to 40 wt. %, 5 wt. % to 40 wt. %, 10 wt. % to 40 wt. %, 20 wt. % to 40 wt. %, 1 wt. % to 30 wt. %, 5 wt. % to 30 wt. %, 10 wt. % to 30 wt. %, 15 wt. % to 30 wt. %, 20 wt. % to 35 wt. %, or 20 wt. % to 30 wt. %.

In some embodiments, the total concentration of non-amino-silicone oil within the oil phase, by weight, is at most 15 wt. %, at most 12 wt. %, at most 10 wt. %, at most 7 wt. %, or at most 5 wt. %, subject to a surface zeta potential of said oil-in-water emulsion being greater than zero, or at least +1 mV, at least +2 mV, at least +3 mV, at least +5 mV, at least +7 mV, or at least +10 mV.

In some embodiments, the total concentration of non-amino-silicone oil within said oil phase, by weight, is within a range of 1 wt. % to 15 wt. %, 3 wt. % to 15 wt. %, 5 wt. % to 15 wt. %, 8 wt. % to 15 wt. %, 1 wt. % to 12 wt. %, 3 wt. % to 12 wt. %, 5 wt. % to 12 wt. %, 3 wt. % to 10 wt. %, 3 wt. % to 8 wt. %, or 2 wt. % to 5 wt. %.

In some embodiments, the non-amino cross-linking agent includes, mainly includes, or consists of a reactive condensation-curable film-forming non-amino-silicone monomer.

In some embodiments, the non-amino cross-linking agent includes, mainly includes, or consists of an ethyl silicate, a poly(dimethoxysiloxane), a poly(diethoxysiloxane), methyltrimethoxysilane, methyltriethoxysilane, isocyanates and Bisphenol A diglycidyl ether. In some embodiments, the total concentration of the non-amino cross-linking agent within the oil phase is at most 35%, at most 30%, at most 20%, at most 15%, at most 10%, or at most 5 wt. % by weight of the oil phase, subject to a surface zeta potential of the oil-in-water emulsion being greater than zero, or at least +1 mV, at least +2 mV, at least +3 mV, at least +5 mV, at least +7 mV, or at least +10 mV.

In some embodiments, the total concentration of the pre-polymer, the non-amino cross-linking agent, the solid, hydrophobic reactive inorganic filler, the amino-silicone oil and the non-amino-silicone oil, including any pigment particles and dispersant for the pigment particles, within the oil phase, is at least 90 wt. %, at least 93 wt. %, at least 95 wt. %, at least 97 wt. %, at least 98 wt. %, or at least 95 wt. %, by weight of the oil phase.

In some embodiments, the aqueous phase further contains an oil-in-water emulsifier that is optionally non-ionic, said oil-in-water emulsifier having an HLB number within a range of 12 to 18, 12 to 17, 12 to 16, 12 to 15, or 13 to 16. In some embodiments, the total concentration of the water and any emulsifier, within the aqueous phase, is at least 90 wt. %, at least 95 wt. %, at least 97 wt. % at least 99 wt. %, on a weight basis.

In some embodiments, the aqueous phase further contains a pH modifying agent. In some embodiments, the pH modifying agent is added to the aqueous phase so that the oil-in-water emulsion has a suitable pH and/or an appropriate surface zeta potential as herein described.

In some embodiments, the textile fibers to which the oil-in-water emulsion is applied are dry or non-wetted textile fibers, or to pre-dyed textile fibers. In some embodiments, the textile fibers to which said oil-in-water emulsion is applied is at least one of unpre-degreased, unpre-shampooed, and unpre-bleached.

While neither for the sake of reducing, delaying or preventing color loss from a colored textile fiber, nor for the sake of coloring a textile fiber with pigments dispersed in the thermoplastic polymeric coat, pigments may be necessary in the first amino-silicone coat, nevertheless in some embodiments, the oil phase may further contain at least one pigment selected from a plurality of sub-micronic pigment particles or a plurality of metallic pigments.

In some embodiments, the oil-in-water emulsion further contains a dispersant, the sub-micronic pigment particles being dispersed within the dispersant.

In some embodiments, the aqueous phase contains, by weight, at most 20 wt. %, at most 10 wt. %, at most 5 wt. %, or at most 2 wt. %, of the amount of the pigment within the oil phase. In some embodiments, the aqueous phase is devoid of said pigment.

In some embodiments, at a relative humidity of 30% to 50%, and at a temperature of 23° C., the at least partially cured film achieves permanence within 24 hours after the applying of said oil-in-water emulsion on the textile fibers, and optionally, within 12 hours, within 4 hours, within 2 hours, or within 1 hour. In particular embodiments, said permanency is achieved within 45 minutes, in less than 30 minutes, in less than 15 minutes, in less than 10 minutes or in less than 5 minutes.

Pre-Treatment of the Reactive Oil Phase

Prior to condensation curing of the amino-silicone layer, various silicone-based molecules may need to undergo hydrolysis. The inventors have discovered that the rate of condensation curing of the amino-silicone layer may be significantly impacted, or even controlled, by the extent of this hydrolysis, and that the hydrolysis—particularly in the film region closest to the textile fibers' external surface—may be diffusion-controlled (i.e., limited by the diffusion of water/humidity from the environment through an overlying film, if any), the thinness of the AS coating (typically on the order of 0.5 micrometers) notwithstanding. The inventors believe that incomplete curing in the film region closest to the textile fibers' surface may appreciably detract from the coloring permanence: when mechanical shear, drag, or other forces are applied to the fibers, the weak linkage between the film and the fibers may be severed or otherwise compromised, leading to deterioration and at least partial detachment of the film from the textile fibers. Perhaps even more significantly, such incomplete curing may enable laundry detergent, textile shampoo, soap, and other materials containing anionic and/or non-ionic surfactants to intercalate via the AS film to the textile fibers' surface, or reach the fibers' surface via a defect in the film, where they may successfully compete with the anionic functional groups of the fibers' surface, thereby weakening the linkage (similar to a "degreasing" operation) between the textile fibers and the AS film at the interface. This deterioration "window" may be potentially available for over a week after the initial film formation, due to the overall (i.e., including diffusion limitations) slow kinetics of the condensation-cure reaction, particularly at the textile fibers-AS interface.

The inventors have yet further discovered that in vitro, partial condensation-curing of the one or more amino-silicone species, prior to application to the textile fibers, may significantly improve various properties of the amino-silicone film obtained. This in vitro step can be referred to as a pre-treatment and the time such step is allowed to proceed may be termed an incubation time, a pre-treatment time or a pre-treatment duration. The properties improved by a suitable pre-treatment for a sufficient time duration include inter alia amino-silicone film adhesivity. The extent of this partial hydrolysis and pre-curing should be sufficient to trigger the formation of "reactive patches", while retaining sufficient reactivity to attach to the textile fibers and undergo additional curing thereon. Without wishing to be bound by any particular theory, the formation of the elastomeric network of cured amino-silicone is believed to initially proceed in an "exponential" manner. The rate of curing and extent of pre-curing at any pre-treatment time point being considered is commensurate, inter alia, with the amount of reactive condensation-curable groups in the participating pre-polymers, the amount of reactive pre-polymers, and in the case of pre-treated oil phase, the amount of pre-treatment solution in the reactants. For simplicity, network formation can be assimilated to a chain reaction with an early slow pace gaining momentum with time, until a plateau is reached at which time curing pace is significantly reduced.

When the oil phase is readily emulsified following its preparation (without any particular pre-treatment), and the resulting oil-in-water emulsion is rapidly applied to the textile fibers (e.g., within less than 30 minutes), the in vitro curing process is substantially inexistent. Thus, in situ curing has to initiate with essentially native amino-silicone species. The partial condensation curing on the textile fibers therefore starts from the lag phase of the curing, when the polymerization is proceeding at an initial relatively slower rate. The pre-treatment allows the partial curing to reach the accelerated "exponential" phase of the network formation process. An in vitro generated reactive patch is believed to act as a nucleus for the continuing curing occurring in situ on the textile fibers following the application of an oil-in-water emulsion prepared from such a pre-treated oil phase. Thus, the in situ curing can proceed, rather than initiate, on the textile fibers, providing a more advanced starting point to the formation of a cohesive network.

A sufficient pre-treatment duration may depend on the oil phase being pre-treated. An increase in the viscosity of the oil phase of 20% or more, as compared to the initial viscosity of the same oil phase at initiation of the pre-treatment, can indicate a sufficient pre-treatment duration.

The extent of this partial pre-curing should be sufficient to enable the detection of a peak of hydroxyl by FTIR analysis of the pre-treatment composition. At this stage of partial hydrolysis and pre-curing, the pre-treatment composition is devoid of fully cured polymers in an amount that would be detected by the formation of a glass transition temperature and therefore lacks Tg. The in vitro pre-curing is sufficiently brief to prevent the formation of a 3D network having a detectable Tg. In some embodiments, the viscosity of the partially pre-cured pre-treatment composition (independently of the viscosity of the isolated reactants of the initial mixture) is of 100 mPa·s or less, or of 50 mPa·s or less, or of 25 mPa·s or less. In some embodiments, the viscosity of the partially pre-cured pre-treatment composition is of at least 1 mPa·s, or of at least 5 mPa·s, or of at least 10 mPa·s.

The pre-treatment of the reactive oil phase further reduces the mass-transfer limitations described hereinabove. The inventors found that advantageously, coloration may be largely unaffected by such a pre-hydrolysis step, as long as condensation-curing can proceed on the textile fibers. Consequently, this additional step substantially does not detract from the target optical density, and may advantageously further improve permanency of the film, as well as the requisite time for attaining such permanency.

The inventors have found that cross-linking density and cross-linking speed may be enhanced by using reactive silicones, and that the density and speed may be further enhanced by utilizing a suitable cross-linker for these reactive silicones. The cross-linking may appreciably contribute to the three-dimensional bonding and strength of the polymer film. This is of particular importance for strengthening or anchoring the film to the textile fibers' surface. Again, without wishing to be limited by theory, the inventors believe that the strength of the adhesion to the textile fibers (associated with "permanence") may be appreciably improved by interactions and/or bonding between the silanol groups from the reactive silicone and various functional groups (e.g., —OH) on the fibers' surface. In addition, the enhanced entanglement within the entire volume of the film improves the cohesive strength of the film, and may contribute (e.g., via steric inhibition) to the stability of the fibers-film bonds.

In some embodiments, a reinforcement filler for these reactive silicones is incorporated into the formulation. The reinforcement filler may include, mainly (more than 50% by weight or by volume) include, or consist essentially of a three-dimensional reactive filler, such as fumed silica. The fumed silica is hydrophobic, in the sense that it is non-self-dispersing in water. In the reactive AS-containing phase, however, the hydrophobic three-dimensional reactive filler is preferably selected and/or adapted so as to be at least somewhat self-dispersing (i.e., disperses in the reactive AS-containing phase down to sub-micronic average particle size (e.g., to a D50, by volume, of 200 nanometers) or below, such that the hydrophobic three-dimensional reactive filler particles can readily serve as nucleation centers to rapidly promote strong three-dimensional cross-linking. In this manner, both the cohesivity of the film, and the adhesion to the textile fibers' surface are improved within a relatively short time frame, and typically, well before the condensation curing has neared completion.

It must be emphasized that the presence—in-and-of-itself—of such a filler, within a formulation, far from indicates any functionality as a three-dimensional reactive filler. For example, in various industrial applications known in the art, fumed silica may serve as a thickening agent. In such a case, and assuming the thickening is for an aqueous medium, the fumed silica would naturally be hydrophilic. However, in order to function as a reactive, three-dimensional cross-linking filler, the filler (e.g., the hydrophobic fumed silica) needs to be disposed in the reactive phase of the formulation (in this case, in the non-aqueous phase containing the reactive amino-silicone materials).

The inventors have yet further discovered that such fillers may be used to overcome or appreciably mitigate the mass-transfer limited kinetics of the overall condensation curing process. Typically, such fillers are characterized by extremely high specific surface areas. The overall specific external and internal surface area of porous solids, such as fumed silica, can be determined by measuring the amount of physically adsorbed gas according to the Brunauer, Emmett and Teller (BET) method. The specific surface area can be determined according to ISO 9277, and in one embodiment, if of at least 25 $m^2/g$, at least 50 $m^2/g$ or at least 75 $m^2/g$, and more typically, at least 100 $m^2/g$, at least 110 $m^2/g$ or at least 120 $m^2/g$, and/or within a range of 25-400 $m^2/g$, 60-400 $m^2/g$, 60-300 $m^2/g$, 80-400 $m^2/g$, 80-350 $m^2/g$, 80-300 $m^2/g$, 90-400 $m^2/g$, 90-350 $m^2/g$, 90-300 $m^2/g$, or 100-350 $m^2/g$. These filler materials may have a low concentration of adsorbed water (e.g., about 0.5%) that is also well-distributed. Consequently, when the filler material is disposed within the reactive phase of the formulation, this low but well-distributed and available water content may serve to partially bypass or get around the mass-transfer limitations of the water diffusing from the environment, through the film, to the textile fibers' surface.

This effect may be enhanced by using reactive filler materials having a relatively high water concentration (e.g., as close as practically possible to the saturation point, e.g., at room temperature, and/or utilization of reactive filler materials of particularly high specific surface areas). In fact, in some embodiments, the inventors have introduced a pre-treatment step in which the solid reactive filler materials are exposed to saturated water vapor, so as to significantly increase the water concentration thereof. A corresponding improvement in film permanence was observed.

The inventors have further discovered that water can additionally or alternatively be added to liquid constituents of the reactive oil phase to achieve similar improvements. A method of introducing a known amount of a pre-treatment solution (e.g., water) to reactants of condensation-curable amino-silicone emulsions, according to some embodiments, is illustrated with reference to FIG. 5. For the purpose of this description, the term "reactant" relates to any material participating in the pre-treatment, whether or not reactive with respect to condensation-curing of a finished emulsion prepared using the water-rich or pre-treated reactants (i.e., the water-enriched reactants). The term reactant may therefore encompass the reactive condensation-curable amino-silicone pre-polymers, and to the extent present in the reactive oil phase, the amino-silicone oils, the non-amino silicone oils, the cross-linking agents, the solid reactive fillers, and the pigment dispersant. Depending on the initial amount of water in the supplied reactants, a preliminary optional drying step S101 can be desired. Such a step may assist better controlling the amount of pre-treatment solution being added to reactants possibly having fluctuating native water contents, reducing variations that may result from such native contents.

Various methods of drying reactants (e.g., water-rich reactants) so as to remove excess amounts of water are known to the skilled person. Drying methods can be selected and adapted to the reactant to be dried. For instance, solid reactants, such as a reactive filler of hydrophobic fumed silica, can be dried in an oven to evaporate excess water. For liquid reactants, such as reactive-condensation-curable amino-silicone pre-polymers, certain cross-linkers or silicone oils, removal of excess water can be performed using molecular sieves having pores adapted to selectively trap water. Following step S101, if required, the reactants dried accordingly are substantially dry, with minimal amounts of residual water, if any. Dry or dried reactants are generally stored in desiccators under dry inert atmosphere or vacuum to ensure their water content, if any, is kept to their respective minima until use. A reactant is substantially dry when containing less than 1 wt. % water by weight of reactant, or less than 0.5 wt. %, or less than 0.1 wt. %, or less than 0.05 wt. %, or less than 0.01 wt. % of water.

In step S102, dry reactants are supplemented with known amounts of water or any desired aqueous pre-treatment solution. This step S102 of controlled water addition can also be referred to as a humidification step, the humidified reactant also called a pre-mix or a pre-treated reactant. In some embodiments, the amount of added water exceeds the amount of water that is conventionally absorbed by the reactant in its native supplied state (e.g., by at least 25% or more or even by at least an order of magnitude). For a particular pre-treatment, it can suffice to humidify a single reactant of the pre-treatment composition. However, more than one reactant can be separately humidified for pre-treatment compositions according to other embodiments. The reactants containing at least one humidified reactant are mixed in step S103 to form the pre-treatment composition of time point 0. Alternatively, the at least one humidified reactant can be humidified and pre-treated individually, the "pre-treatment" mixture being formed following such separately performed pre-treatment. Provided that the amount of added water is sufficiently low, the pre-treatment composition forms a uniform oil phase (without a visibly detectable separate aqueous phase). The pre-treatment oil phase is clear (lacking turbidity) further confirming that the amount of added water is low enough. The aqueous pre-treatment solution is typically progressively added to the dry or dried reactant, allowing for a more gradual and homogenous water adsorption, reducing the risks of phase separation.

In some embodiments, the pre-treatment solution essentially consists of distilled water having a pH in the range of 6.5 to 7.5

In some embodiments, water (or the aqueous pre-treatment solution) constitutes 10 wt. % or less by weight of the reactant, or less than 5 wt. %, or less than 4 wt. %, or less than 3 wt. %, or less than 1 wt. %; optionally constituting at least 0.1 wt. %, or at least 0.2 wt. % or at least 0.3 wt. % of the weight of the reactant.

In some embodiments, water (or the aqueous pre-treatment solution) is added to the reactant in an amount of 15 wt. % or less, 12.5 wt. % or less, 10 wt. % or less by weight of the reactant, or less than 5 wt. %, or less than 4 wt. %, or less than 3 wt. %, or less than 1 wt. %; optionally added in at least 0.1 wt. %, or at least 0.2 wt. % or at least 0.3 wt. % by weight of the reactant. In some embodiments, the water (or aqueous pre-treatment solution) is added to the reactant in an amount within a range of 0.1 wt. % to 15 wt. %, 0.2 wt. % to 15 wt. %, or 0.3 wt. % to 12.5 wt. % by weight of the reactant.

In some embodiments, water (or the aqueous pre-treatment solution) constitutes 8 wt. % or less, 6.7 wt. % or less, 5 wt. % or less, 2.5 wt. % or less 2 wt. % or less, 1 wt. % or less, or 0.5 wt. % or less by weight of the oil phase. In some embodiments, water (or the aqueous pre-treatment solution) constitutes at least 0.01 wt. %, or at least 0.05 wt. % or at least 0.1 wt. %, or at least 0.15 wt. %, or at least 0.2 wt. %, or at least 0.25 wt. %, or at least 0.5 wt. %, or at least 0.75 wt. %, or at least 1 wt. % of the weight of the oil phase. In some embodiments, water (or the aqueous pre-treatment solution) is present in the oil phase in an amount within a range of 0.01 wt. % to 8 wt. %, 0.1 wt. % to 8 wt. % or 0.2 wt. % to 6.7 wt. % by weight of the oil phase.

In some embodiments, water (or the aqueous pre-treatment solution) is added to at least one reactant of the oil phase in a total amount of 8 wt. % or less, 7 wt. % or less, 5 wt. % or less, 2.5 wt. % or less 2 wt. % or less, 1 wt. % or less, or 0.5 wt. % or less by weight of the oil phase. In some embodiments, water (or the aqueous pre-treatment solution) is added to the at least one reactant in at least 0.01 wt. %, or at least 0.05 wt. % or at least 0.1 wt. % by weight of the oil phase. In some embodiments, the water (or aqueous pre-treatment solution) is added to the at least one reactant in an amount within a range of 0.01 wt. % to 8 wt. %, 0.05 wt. % to 8 wt. % or 0.1 wt. % to 5 wt. % by weight of the oil phase.

In some embodiments, a ratio of volume of oil to aqueous phase within the oil phase or the pre-treated oil phase is at least 9:1, at least 9.33:0.67 (14:1), at least 9.5:0.5 (19:1), or at least 9.75:0.25 (39:1), the oil phase or pre-treated oil phase being optionally entirely devoid of aqueous phase.

It should be noted that the amounts of aqueous pre-treatment solutions added to the reactants are insignificant as compared to the amount of water or aqueous medium surrounding the droplets following emulsification of the oil phase. The inventors have established that the water phase of the emulsion only mildly contributes to the processes triggered by the in vitro pre-treatment. It is believed that the surrounding water can only interact with the external surface of the oil droplets, a further diffusion towards the content of the droplet being de facto very slow. For similar reasons, water present on textile fibers, or further added as a moisturizer, do not contribute in a manner comparable to the pre-treatment. In this particular case, it is further believed that the oil droplets, following their deposition on the textile fibers have a tendency to repel such water (making it unavailable for film formation). The presence of water within the oil phase is believed to mitigate the slow diffusion of such molecules from external/surrounding sources.

The pre-treatment composition of step S103 can then be incubated for any predetermined amount of time in step S104. Incubation can be performed at room temperature (circa 23° C.) or at any other temperature, generally not exceeding 50° C., when above ambient. It is believed that during the incubation time of the pre-treatment composition, the water is in an amount sufficient to trigger hydrolysis of at least part of the hydrolysable moieties of the relevant reactants. While complete hydrolysis is not sought during the pre-treatment period, it should be understood that even in such case the pre-polymers can remain reactive with respect to condensation curing. The fact that the pre-polymers are still reactive can readily be confirmed by the fact that the pre-treatment composition is still liquid and/or lack a glass transition temperature.

Following incubation, the pre-treated oil phase can be added to a desired aqueous phase (e.g., with or without added emulsifier) for emulsification in step S105. Following this step, the emulsion of reactive condensation-curable amino-silicone is ready to be applied. The actual application to textile fibers S106 can take place generally within 30 minutes from emulsification.

Without wishing to be bound by any particular theory, it is believed that the minute amount of water (or aqueous pre-treatment solution) present in the pre-treatment composition (i.e., in the reactive oil phase) can promote the hydrolysis of the hydrolysable moieties of the reactive reactants. This partial in vitro hydrolysis can in turn promote condensation-curing of the hydrolyzed moieties of the reactive reactants (i.e., amino-silicone pre-polymers). The inventors discovered that triggering in vitro the condensation-curing of the amino-silicone pre-polymers accelerate their ongoing condensation, once applied on the textile fibers, typically shortening the duration required for full curing. The incubation time of the pre-treatment composition (which may depend, for example, on temperature, type of aqueous pre-treatment solution, amount added per reactant and in total, and like factors) should be sufficient to provide such trigger, but short enough to ensure that the amino-silicone pre-polymers being applied following emulsification are still reactive and capable of condensation-curing on the textile fibers following their application thereon.

FIG. 3A is a schematic plot illustrating the hydroxyl concentration as a function of time, in an in-vitro pre-treatment reaction of a reactive amino-silicone formulation (e.g., oil-in-water emulsion), according to embodiments of the present invention. The times (along the X axis) shown are qualitative and illustrative, as the absolute times might be slower or faster, depending on the particular pre-polymer, formulation constituents, and operating parameters.

According to some embodiments of the present invention, the reaction takes place within a pH range of 7.5 to 12, and more typically, between 8 and 11, or between 8 and 10.5. The inventors believe that the initial rise in the hydroxyl concentration stems from the hydrolysis of hydrolysable groups (typically alkoxy, acyloxy, and/or oxime) to form silanol groups. This initial rise may begin to level off as the rate of production of the hydroxyl groups slows. With time, the relatively slow curing reaction ensues, and the silanol groups polymerize via a condensation reaction to produce siloxane bonds (and liberating water). This condensation reaction consumes hydroxyl groups, such that the hydroxyl concentration is reduced as reaction time progresses.

FIG. 3B is a schematic plot illustrating textile coloration efficacy of the partially-reacted amino-silicone formulation of FIG. 3A, applied to textile fibers, as a function of the in-vitro reaction time of the pre-treatment formulation, prior to the application of the partially-reacted formulation to the textile fibers. As described in further detail herein, the partially-reacted amino-silicone formulation produced is subsequently emulsified with water (with or without further additives, such as emulsifiers or pH modifying agents) to produce the textile fibers-treatment emulsion that may be applied directly to the textile fibers. It is evident from the qualitative plot provided in FIG. 3B that efficacious coloration of the textile fibers may be attained even at t=0, which corresponds to no in-vitro reaction of the reactive amino-silicone formulation before applying the formulation to the textile fibers. The inventors have found that textile coloration efficacy may remain high for a long period of time, until a relatively high extent of cross-linking has been achieved. Textile coloration efficacy may then decrease, or appreciably decrease, as the extent of cross-linking continues to increase. The inventors believe that upon application of the partially-cured amino-silicone formulation to the textile fibers, highly cross-linked material achieves poor wetting of the fibers, and much of the polymer embedded pigment is simply washed away upon removal of excess material. By way of example, such a state is denoted by point A in FIG. 3B.

This result using highly cross-linked material would appear to be corroborated by the failure of various disclosed non-reactive amino-silicone based hair-coloring formulations and methods to achieve satisfactory initial coloration of the hair fiber. The same outcome would be expected when coloring textile fibers. Such cross-linked silicones, inadequate for the present teachings, are often referred to as silicone resins, which, as explained, can be characterized by at least one of a high molecular weight, a high viscosity (or even a solid state at ambient temperature), or a glass transition temperature (Tg).

Moreover, even if satisfactory initial coloration is achieved, e.g., by a formulation containing less highly cross-linked material that sufficiently wets the textile fiber surface, such a formulation may manifestly fail to exhibit coloring permanence (e.g., wash-resistance). By way of example, such a state is denoted by point B in FIG. 3B. Point B is also denoted in FIG. 3C, which provides a schematic plot illustrating textile fibers coloration permanency as a function of the in-vitro reaction time of the partially-reacted AS formulation, prior to emulsification and application of the formulation to the textile fibers. It is evident that for the in-vitro reaction time of point B, the coloration appears satisfactory, but the permanence is low.

As provided in further detail herein, the coloration permanence is measured after removing, from the textile, excess amounts of the applied formulation and then allowing the applied formulation to cure on the textile fibers (e.g., for 24 hours), at ambient conditions. FIG. 3C schematically illustrates permanency as assessed by wash resistance of coloration 24 hours after application. As shall be illustrated herein-below and in the Examples, in some embodiments, the pre-treatment of the reactive oil phase allows permanency of coloration to develop at an earlier time point within the 24 hours following coloration.

Substantially as described hereinabove, the inventors believe that incomplete curing in the film region closest to the textile fibers' external surface may appreciably detract from the coloring permanence, due to mechanical forces as well as susceptibility to intercalation and chemical attack, at the interface between the AS film and the external surface of the fiber.

It must be emphasized that various amino-silicone formulations deemed "reactive" are, in practice, substantially non-reactive, in that the formulations, prior to application, are already highly cross-linked, such that the potential for additional cross-linking post application may be minor in extent (particularly under ambient conditions), and may be insufficient to achieve satisfactory (initial) coloration. Alternatively, the initial coloration may be satisfactory, however, permanence may be poor, or less than satisfactory.

With reference again to FIG. 3C, it is evident from this qualitative plot that coloration permanence of the textile fibers may be unsatisfactory at t=0, which corresponds to no in-vitro reaction of the reactive amino-silicone formulation before applying the formulation to the textile fibers. While efficacious coloration of the textile fibers may be attained at low in-vitro reaction times, the inventors have found that coloration permanency may be unsatisfactory, as described, due in part to the extremely low level of cross-linking at the interface between the AS film and the external surface of the fibers. As the level of cross-linking at the interface increases with time, permanence correspondingly increases, as indicated by first shoulder C. As the level of cross-linking at the interface further increases with time, permanence may plateau or substantially plateau, as indicated by permanency plateau D.

FIG. 3D is a schematic plot illustrating the tackiness of the partially-reacted amino-silicone formulation of FIG. 3A, applied to textile fibers, as a function of the in-vitro reaction time of the formulation, prior to the application of the formulation to the textile fibers. The inventors believe that textile fibers tackiness decreases with an increase in cross-linking. Thus, by controlling the in-vitro reaction time and operating conditions, the inventive method enables operation within an overlap of the coloration, tackiness, and permanence "time windows" ("windows"), so as to achieve sufficient textile coloration (e.g., as characterized by optical density or the like) as well as coloration permanence.

The inventors have surprisingly found, in addition, that the pH of the pre-treatment solution used to humidify reactants of in-vitro reaction mixtures can be controlled to accelerate the hydrolysis and condensation reactions, so as to reduce tackiness virtually immediately (e.g., a low in-vitro reaction time of at most 10 minutes) and/or to widen the overlap of the coloration, tackiness, and permanence time windows. More specifically, the pH of the pre-treatment solution should be at most 2.5, at most 2, and more typically, at most 1.8, at most 1.6, at most 1.4, or at most 1.2. The pH should be within a range of 0.5 to 2.5, 0.5 to 2.0, 0.7 to 2.0, 0.7 to 1.8, 0.7 to 1.6, 0.7 to 1.4, 0.7 to 1.2, 0.9 to 2.0, 0.9 to 1.7, 0.9 to 1.5, 0.9 to 1.3, or 0.9 to 1.2.

The inventors have found, however, that typical acids used to lower the pH may contribute "permanent" ionic content to the reaction mixture, which may ultimately detract from the properties of the amino-silicone film.

Surprisingly, the inventors have discovered that by using a volatile acid (preferably concentrated acetic acid, e.g., containing at least 30%, at least 40%, at least 50%, at least 60%, or at least 80%) to reduce the pH, the pH of the pre-treatment solution may be sufficiently lowered to advantageously modify the time windows of the in-vitro reaction, and yet may be volatilized such that there remains no residual ionic content from the acid. Consequently, the requisite in-vitro reaction time may be reduced, reaction control may be relaxed, and process robustness may be improved, all without introducing contaminants via the acidifying agent.

FIG. 4 provides a schematic plot illustrating the extent of hydrolysis (as detectable by hydroxyl/silanol concentration), coloration efficacy, tackiness, and coloration permanency of textile fibers as a function of the in-vitro reaction time (prior to application of the partially-reacted formulation to said textile fibers) of, or utilizing, a pH-modified aqueous pre-treatment solution, reactive amino-silicone formulation based on the formulation of FIG. 3A.

The pre-treatment duration may therefore depend inter alia on the type and onset of desired outcome, as well as on the type of pre-treatment solution and its total concentration in the reactive oil phase, based on the presence of the accordingly pre-treated reactants. In some embodiments, the pre-treatment duration does not exceed 24 hours (hrs), alternatively being of less than 12 hrs, less than 8 hrs, less than 6 hrs, or less than 4 hrs. Advantageously, the pre-treatment duration can be of 120 minutes or less, less than 90 minutes, less than 60 minutes, less than 30 minutes, less than 20 minutes, less than 10 minutes, or less than 5 minutes.

As the rate of hydrolysis and/or (partial) condensation-curing may depend on temperature, the pre-treatment duration can be shortened with an increase in temperature of pre-treatment. While pre-treatment is conveniently performed at ambient temperature, it can alternatively be performed at elevated temperatures, typically not exceeding 75° C. In some embodiments, pre-treatment is performed at a temperature in the range of 15–75° C., 15-70° C., 15-65° C., 15-60° C., 15-55° C. 15-50° C., 18-45° C., 20-40° C., 20-35° C., 20-30° C., or 20-25° C.

The reactive oil phases pre-treated according to the present teachings can thereafter be emulsified for the preparation of oil-in-water emulsions of reactive condensation-curable amino-silicone pre-polymers fulfilling the respective teachings pertaining to emulsions being applied to textile fibers according to the present invention.

According to some embodiments, the reactive condensation-curable amino-functional silicone pre-polymer is present at a concentration in the range of from about 0.001 wt. % to 20 wt. % by weight of the total weight of the composition (e.g., oil-in-water emulsion), such as from about 0.005 wt. % to 10 wt. %, from about 0.005 wt. % to 5 wt. %, from about 0.005 wt. % to 2.5 wt. % or from 0.01 wt. % to 1 wt. % by weight of the total weight of the composition.

According to some embodiments, the concentration of reactive condensation-curable amino-functional silicone compounds is at least 45 wt. % at least 55 wt. %, at least 60 wt. %, or at least 65 wt. %, and optionally within a range of 50-100 wt. %, 50-95 wt. %, 50-90 wt. %, 50-85 wt. %, 50-80 wt. %, 55-95 wt. %, 55-85 wt. %, 60-95 wt. %, 60-85 wt. %, 65-95 wt. %, 65-90 wt. %, or 70-95 wt. % by weight of the oil phase.

According to some embodiments, suitable non-amino-silicone oils can be linear, branched or cyclic organosiloxanes, such as decamethylcyclopentasiloxane (D5), octamethyl-cyclotetrasiloxane (D4), or hexamethyl-disiloxane (M2).

According to some embodiments, the total concentration of non-amino-silicone oil is at most 15 wt. %, at most 12 wt. %, at most 10 wt. %, at most 7 wt. %, or at most 5 wt. % by weight of the oil phase.

According to some embodiments, the sub-micronic pigment particles, if included in any of the amino-silicone emulsion and the aqueous dispersion of neutralized polymer, comprise an organic pigment, for example an organic pigment selected from the group consisting of perylene pigments; phthalocyanine pigments; quinacridone pigments; and imidazolone pigments.

According to some embodiments, the sub-micronic pigment particles comprises an inorganic pigment, for example an inorganic pigment selected from the group consisting of titanium dioxide, cadmium sulfoselenide, iron oxide, bismuth vanadate, cobalt titanate, sodium aluminosulfosilicate, mixed Fe—Mg—Ti oxides, manganese ferrite, and metallic or alloy pigments.

In some embodiments, the sub-micronic organic or inorganic pigments (or combinations thereof) serve as color imparting agents. The sub-micronic pigments may also be referred to as light absorbing pigments or simply as absorbing pigments.

According to some embodiments, the sub-micronic pigment is an organic or inorganic pigment selected from the group consisting of the following colors: CI 10006, CI 10020, CI 10316, CI 11680, CI 11710, CI 11725, CI 11920, CI 12010, CI 12085, CI 12120, CI 12370, CI 12420, CI 12480, CI 12490, CI 12700, CI 13015, CI 14270, CI 14700, CI 14720, CI 14815, CI 15510, CI 15525, CI 15580, CI 15620, CI 15630, CI 15800, CI 15850, CI 15865, CI 15880, CI 15980, CI 15985, CI 16035, CI 16185, CI 16230, CI 16255, CI 16290, CI 17200, CI 18050, CI 18130, CI 18690, CI 18736, CI 18820, CI 18965, CI 19140, CI 20040, CI 20470, CI 21100, CI 21108, CI 21230, CI 24790, CI 26100, CI 27755, CI 28440, CI 40215, CI 40800, CI 40820, CI 40825, CI 40850, CI 42045, CI 42051, CI 42053, CI 42080, CI 42090, CI 42100, CI 42170, CI 42510, CI 42520, CI 42735, CI 44045, CI 44090, CI 45100, CI 45190, CI 45220, CI 45350, CI 45370, CI 45380, CI 45396, CI 45405, CI 45410, CI 45430, CI 47000, CI 47005, CI 50325, CI 50420, CI 51319, CI 58000, CI 59040, CI 60724, CI 60725, CI 60730, CI 61565, CI 61570, CI 61585, CI 62045, CI 69800, CI 69825, CI 71105, CI 73000, CI 73015, CI 73360, CI 73385, CI 73900, CI 73915, CI 74100, CI 74160, CI 74180, CI 74260, CI 75100, CI 75120, CI 75125, CI 75130, CI 75135, CI 75170, CI 75300, CI 75470, CI 75810, CI 77000, CI 77007, CI 77266, CI 77267, CI 77268:1, CI 77891, CI 77947, lactoflavin, caramel, capsanthin, capsorubin, beetroot red, anthocynanins, bromothymol blue, bromocresol green, and acid red 195.

According to some embodiments, the sub-micronic pigment is selected from the group consisting of the following organic colors:

D&C Black No. 2, D&C Black No. 3, FD&C Blue No. 1, D&C Blue No. 4, D&C Brown No. 1, FD&C Green No. 3, D&C Green No. 5, D&C Green No. 6, D&C Green No. 8, D&C Orange No. 4, D&C Orange No. 5, D&C Orange No. 10, D&C Orange No. 11, FD&C Red No. 4, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, FD&C Red No. 40, Ext. D&C Violet No. 2, FD&C Yellow No. 5, FD&C Yellow No. 6, D&C Yellow No. 7, Ext. D&C Yellow No. 7, D&C Yellow No. 8, D&C Yellow No. 10 and D&C Yellow No. 11.

In some embodiments, the pigments of the present compositions provide a special visual effect, instead of or in addition to a coloring effect and/or a metallic appearance. Special effects include, by way of non-limiting example, a fluorescent effect, a glittering effect, a pearlescent effect, a nacreous effect and a phosphorescent effect. These effects may be visible under regular illumination or may require (or be further increased) by special conditions of observation, such as a function of lighting conditions, angle of observation etc. For instance, fluorescent pigments may become visible or may provide a fluorescent effect when subjected to ultraviolet (UV) light. At the other end of the spectrum, up-converting pigments are luminescent materials which are able to convert near infrared (NIR) light to visible (VIS) light. Additional colorants providing for less typical coloring further include, by way of non-limiting example, thermochromic pigments or dyes, allowing the compositions comprising them to change color as a result of a change in temperature, and pH dependent pigments, whose color is modified by pH.

Any of the afore-said pigments can further be surface treated, for instance with an organic agent, so as to further improve any desired property of the pigment (e.g., visual effect, chemical stability, dispersibility, charge, ability to adhere to fibers, ability to interact with the amino-silicone matrix, etc.). Surface treatment techniques need not be detailed herein, and surface-treated pigments may be commercially available in the required form (e.g., non-ionic, cationic, anionic, or positively charged, negatively charged, or substantially non-charged). The surface treatment of the pigment particles can be a chemical coat, which for instance can be a fatty acid, such as oleic acid, stearic acid, an adhesion promoting polymer coat, such as an acrylic polymer, a silane polymer or an amino-silane polymer, and such chemical coats known in the art of pigments.

All of such pigments may be employed, if desired, by all aspects and embodiments of the present textile-coloring methods and the kits therefor, the pigments being adapted to the matrix into which they are incorporated. In one embodiment, when pigments are desired in an amino-silicone coat, the pigment particles can be surface treated (e.g., by acid groups), so as to ameliorate interaction between the pigment and the amino-silicone pre-polymers entrapping them during the formation of a 3D network of amino-silicone on the textile fibers. However, as pigments, when incorporated in a polymeric coat, are differently compounded in the polymeric material having neutralizable acid moieties, such pigment treatment can be superfluous and even undesired. Color imparting agents as used in the present invention are pigments, which may optionally be combined or replaced by dyes in particular cases (e.g., for tinting). However, even when dyes are used as color imparting agent to a composition or to a pigment coat, they are not oxidative dyes. In some embodiments, compositions according to the present teachings are substantially devoid of oxidative dyes and of any chemical agent conventionally used in combination with oxidative dyes, including by way of non-limiting example, dyes' couplers and oxidizing agents (e.g., a hydrogen peroxide developer).

In some embodiments, the pigments are size reduced and/or dispersed ahead of incorporation into the reactive oil phase of the present emulsions. In such case, the size reduction and/or dispersion step can be performed in the presence of a pigment dispersant.

According to some embodiments, the pigment dispersant is present in the oil-in-water emulsion in an amount ranging from 25% to 400% by weight of the sub-micronic pigment particles. In some embodiments, the dispersant and the pigment particles are present at a relative weight by weight ratio in the range of 0.5:1 to 2:1, 0.75:1 to 1.5:1, or 0.8:1 to 1.2:1.

According to some embodiments, the dispersant adapted to disperse the pigments is compatible with the condensation-curable formulation. By compatible, it is meant, for instance, that the pigment dispersant is miscible in the reactive oil phase of the formulation, that the pigment dispersant does not delay, reduce or prevent condensation curing, and that the pigment dispersant is stable (e.g., non-reactive) during the size reduction of the pigment. Preferably, the pigment dispersant can have a positive charge.

Such dispersant can have a silicone backbone, such as silicone polyether and silicone amine dispersants. Suitable pigment dispersants include for example silicone amines such as BYK LPX 21879, by BYK, GP-4, GP-6, GP-344, GP-851, GP-965, GP-967, and GP-988-1, by Genesee Polymers, silicone acrylates such as Tego® RC 902, Tego® RC 922, Tego® RC 1041, and Tego® RC 1043, by Evonik, PDMS silicones with a carboxylic function such as X-22162 and X-22370 by Shin-Etsu, silicone epoxy such as GP-29, GP-32, GP-502, GP-504, GP-514, GP-607, GP-682, and GP-695, by Genesee Polymers, or Tego® RC 1401, Tego® RC 1403, Tego® RC 1412, by Evonik, or polyglycerine modified silicones such as KF-6106 by Shin-Etsu. The silicone amine dispersants are positively charged and can be advantageous in some embodiments according to the present teachings.

In some embodiments, the pigment dispersants being amino-silicones have an Amine Number in the range of 3-1,000, 3-500 or 3-200.

Pigment dispersants having functional moieties able to react with the reactants of the reactive oil phase may advantageously, in addition to pigment dispersion per se, further improve the amino-silicone 3D network forming therefrom. For instance, silicone epoxy pigment dispersants can favorably interact with the amine-moieties of the amino-silicone pre-polymer to further increase the cohesivity of the pigmented amino-silicone film.

Generally, a material used in the compositions according to the present teachings is said to be compatible with another, if it does not prevent its activity or does not reduce it to an extent that would significantly affect the intended purpose. For instance, a pigment dispersant would not be compatible if, among other things, preventing the curing of the condensation-curable amino-silicone pre-polymers, or reducing or retarding curing to an extent that the amino-silicone film would not sufficiently and/or rapidly attach to substrate fibers, or would be deleterious to the pigments, and any like undesired effects. In some embodiments, compatibility may additionally mean that the materials deemed compatible share a common property, such as a common silicon-based chemistry or a similar physical parameter. For instance, materials having a similar refractive index (RI; within ±10% from one another) are believed to yield clearer cured films, as compared to materials having relatively dissimilar RI that may appear more turbid.

According to some embodiments, the plurality of pigment particles present in the reactive oil phase can be a mixture of different pigments each providing for a different color or a different shade of a same color.

Depending on their morphology, particles (e.g., sub-micronic (absorbing) pigments, reinforcement fillers, and the like) may be characterized by their length, width, thickness, diameter, or any such representative measurement of their X-, Y- and Z-dimensions. Typically, such sizes are provided as average of the population of particles and are provide by the manufacturer of such materials. These sizes can be determined by any technique known in the art, such as microscopy and Dynamic Light Scattering (DLS). In DLS techniques, the particles are approximated to spheres of equivalent behavior and the size can be provided in terms of hydrodynamic diameter. DLS also allows assessing the size distribution of a population. The same applies to liquid droplets and may assist for instance in the characterization of emulsion droplets, all typically having a globular shape. As used herein, particles having a size of, for instance, 1 μm or less, have at least one dimension equal to or smaller than 1 μm, and possibly two or even three, depending on shape. When concerned with emulsion droplets having, by way of example, a size of 5 μm or less, the droplets are understood to have an average diameter ($D_V50$) equal to or smaller than 5 μm.

Though not essential, the particles or emulsion droplets of any particular kind may preferably be uniformly shaped and/or within a symmetrical distribution relative to a median value of the population and/or within a relatively narrow size distribution for this particular kind. In the following, and unless otherwise clear from context, the term "particle" refers both to solid particles (e.g., pigments and the like) and to liquid droplets (e.g., emulsion droplets, micelles and the like).

A particle size distribution (PSD) is said to be relatively narrow if at least one of the two following conditions applies:

A) the difference between the hydrodynamic diameter of 90% of the particles and the hydrodynamic diameter of 10% of the particles is equal to or less than 150 nm, or equal to or less than 100 nm, or equal to or less than 50 nm, which can be mathematically expressed by: (D90−D10)≤150 nm and so on; and/or B) the ratio between a) the difference between the hydrodynamic diameter of 90% of the particles and the hydrodynamic diameter of 10% of the particles; and b) the hydrodynamic diameter of 50% of the particles, is no more than 2.0, or no more than 1.5, or no more than 1.0, which can be mathematically expressed by: (D90−D10)/D50≤2.0 and so on.

D10, D50 and D90 can be assessed by number of particles in the population, in which case they may be provided as $D_N10$, $D_N50$ and $D_N90$, or by volume of particles, in which case they may be provided as $D_V10$, $D_V50$ and $D_V90$. The foregoing measurements can be obtained by DLS techniques when the samples to be studied are suitably fluid or by microscopy when the particles under study are in dry form. As used herein, D50, which can also be termed the "average measured particle size" or simply the "average particle size" may refer, depending on the measuring method most suited to the particles being considered and their media, either to $D_V50$ (by DLS and the like) or to the volume average size of particles found in a field of view of a microscope adapted to analyze in the scale of the particles. D90 accordingly relate to measurements applying to 90% of the population under study, thus also termed the "predominant measured particle size" or simply the "predominant particle size" which can for instance be assessed by DLS techniques as $D_V90$.

As mentioned above, such relatively uniform distribution may not be necessary for certain applications. For instance, having a relatively heterogeneously sized population of sub-micronic pigments particles may allow, in a coating formed thereby, relatively smaller particles to reside in interstices formed by relatively larger particles providing in combination a relatively uniform coating.

The particles may be characterized by an aspect ratio, i.e., a dimensionless ratio between the smallest dimension of the particle and the longest dimension or equivalent diameter in the largest plane orthogonal to the smallest dimension, as relevant to their shape. The equivalent diameter (Deq) is defined by the arithmetical average between the longest and shortest dimensions of that largest orthogonal plane. Particles having an almost spherical shape, and emulsion droplets amongst them, are characterized by an aspect ratio of approximately 1:1, whereas rod-like particles can have higher aspect ratios and flake-like particles can even have an aspect ratio of up to 1:100, or even more.

Such characteristic dimensions are generally provided by the suppliers of such particles and can be assessed on a number of representative particles by methods known in the art, such as microscopy, including, in particular, by light microscope for particles of several microns or down to estimated dimensions of about 200 nm, by scanning electron microscope SEM for smaller particles having dimensions of less than 200 nm (SEM being in particular suitable for the planar dimensions) and/or by focused ion beam FIB (preferably for the thickness and length (long) dimensions of sub-micronic particles, also referred to herein as nanoparticles or nanosized particles). While selecting a representative particle, or a group of representative particles, that may accurately characterize the population (e.g., by diameter, longest dimension, thickness, aspect ratio and like characterizing measures of the particles), it will be appreciated that a more statistical approach may be desired. When using microscopy for particle size characterization, a field of view of the image-capturing instrument (e.g., light microscope, Scanning Electron Microscopy (SEM), Focused Ion Beam (FIB)-SEM, Transmission Electron Microscopy (TEM) etc.) is analyzed in its entirety. Typically, the magnification is adjusted such that at least 5 particles, at least 10 particles, at least 20 particles, or at least 50 particles are disposed within a single field of view. Naturally, the field of view should be a representative field of view as assessed by one skilled in the art of microscopic analysis. The average value characterizing such a group of particles in such a field of view is obtained by volume averaging. In such case, $D_V 50 = \Sigma[(Deq (m))^3/m]^{1/3}$, wherein m represents the number of particles in the field of view and the summation is performed over all m particles. As mentioned, when such methods are the technique of choice for the scale of the particles to be studied or in view of their media, such measurements can be referred to as D50.

According to some embodiments, the sub-micronic pigment comprises on average particles having a $D_V 50$ of at most 1,000 nm, at most 750 nm, at most 500 nm, at most 250 nm, at most 150 nm, or at most 100 nm, and optionally, a $D_V 10$ of at least 10 nm, at least 25 nm, or at least 50 nm. In some embodiments, the sub-micronic pigment particles are in a range comprised between a $D_V 10$ of at least 10 nm and a $D_V 90$ of at most 2,500 nm, or in a range between a $D_V 10$ of at least 25 nm and a $D_V 90$ of at most 1,500 nm, or in a range between a $D_V 10$ of at least 50 nm and a $D_V 90$ of at most 1,000 nm.

According to some embodiments, the sub-micronic pigment predominantly comprises particles having a $D_V 90$ of at most 1,000 nm, at most 750 nm, at most 500 nm, at most 250 nm, at most 150 nm, or at most 100 nm, and optionally, a $D_V 50$ of at most 300 nm, at most 250 nm, at most 200 nm, at most 150 nm, at most 100 nm, or at most 75 nm. In some embodiments, the sub-micronic pigment particles have a $D_V 10$ of at least 10 nm, at least 25 nm, or at least 50 nm. In some embodiments, the sub-micronic pigment particles are in a range comprised between a $D_V 10$ of at least 10 nm and a $D_V 90$ of at most 1,000 nm, or in a range between a $D_V 10$ of at least 25 nm and a $D_V 90$ of at most 750 nm, or in a range between a $D_V 10$ of at least 25 nm and a $D_V 90$ of at most 500 nm.

According to some embodiments, the composition or kit disclosed herein further comprises a cross-linker, for example, an organosilicon compound able to react through all non-amino reactive groups of the reactive silicone, and a cross-linking agent comprising a mercapto group, an epoxy group or an acrylate group, all able to react through amino reactive groups of the reactive silicone.

Generally, cross-linking agents comprise at least three reactive groups for the formation of the network of oligomers and polymers resulting in the elastomeric network.

The organosilicon cross-linking agent must have hydrolysable groups (Y). After hydrolysis, the silanol groups obtained can undergo condensation reaction with the reactive amino-silicone pre-polymer to give siloxane bonds.

The organosilicon cross linker can contain:
tetrafunctional hydrolysable groups and consist for example of silane having a Q units ($SiO_{4/2}$), such as $SiY_4$
or trifunctional hydrolysable groups and consist of silane or siloxane oligomers having T units of the formula $R^a SiO_{3/2}$, like $RaSiY_3$
or difunctional hydrolysable groups and consist of silane or siloxane oligomers having D units of the formula $R^b_2 SiO_{2/2}$, like $R^b_2 SiY_2$, as long as the cross-linker has a total of at least three hydrolysable groups,
or monofunctional hydrolysable groups having M units, as long as the cross-linker has a total of at least three hydrolysable groups,
where the hydrolysable group (Y) can be selected from
Alkoxy (e.g., methoxy, ethoxy, propoxy, isopropoxy, methoxyethoxy and the like)
Oxime (e.g., methylethylketoxime)
Acyloxy (e.g., acetoxy)
where the $R^a$ and $R^b$ substituents are selected from
$C_1$-$C_6$ or $C_1$-$C_4$ Alkyl groups,
Alkenyl groups (vinyl, allyl, etc.),
Aminoalkyl groups (monoamino, such as aminopropyl $NH_2(CH_2)_3$; diamino, such as aminoethylaminopropyl $NH_2(CH_2)_2 NH(CH_2)_3$; or triamino)
Epoxy group (e.g., glycidoxypropyl)
Acrylate group (e.g., methacryloxypropyl)
Mercapto group (e.g., mercaptopropyl)

According to some embodiments, the cross-linking agent can be a branched or a linear polyorganosiloxane comprising at least one of Q units, T units, D units and M units, with the proviso that the total amount of hydrolysable groups and/or of silanols in the cross-linking agent is of at least three, allowing the formation of a 3D network. When a mixture of cross-linking agents is used, at least one cross-linking agent of the mixture must contain a total of at least three hydrolysable groups and/or of silanols.

According to some embodiments, the cross-linker can be an ethylsilicate, such as tetraethylsilicate (CAS No 78-10-4), poly(diethoxysiloxane) oligomers, such as Evonik Dynasylan® 40 with a silicon dioxide content of approximately 40-42% upon complete hydrolysis, Colcoat® Ethylsilicate 48 with a silicon dioxide content of approximately 48% upon complete hydrolysis (CAS No. 11099-06-2), poly(dimethoxysiloxane) (CAS No. 25498-02-6), 3-Glycidyloxypropyl trimethoxysilane by Evonik, Carbodilite Emulsion E-05, having 40% multifunctional polycarbodiimide in anionic emulsion, and Carbodilite V02-B, having 100% multifunctional polycarbodiimide.

According to some embodiments, the cross-linker can be a reactive amino-silicone monomer, such as aminopropyltriethoxysilane (CAS No. 919-30-2), bis(triethoxy-silylpropyl)amine (CAS No. 13497-18-2), or mixtures thereof.

According to some embodiments, the cross-linker is a non-amino silicone having a molecular weight of less than 1,000 g/mol, thus includes, mainly includes, or consists of a reactive condensation-curable film-forming non-amino-silicone monomer. In some embodiments, the total concentration of the non-amino cross-linking agent is at most 35 wt. %, at most 30 wt. %, at most 20 wt. %, at most 15 wt. %, at most 10 wt. %, or at most 5 wt. % by weight of the oil phase.

As used herein in the specification and in the claims section that follows, the term "mainly includes", typically with respect to a component within a formulation, refers to a weight content of at least 50% of that component.

According to some embodiments, the total concentration of: reactive condensation-curable film-forming amino-silicone pre-polymers; amino- and non-amino-silicone oils; non-amino cross-linking agent; and reactive filler, including any pigment particles and dispersant for said pigment particles, within said oil phase, is at least 90 wt. %, at least 93 wt. %, at least 95 wt. %, at least 97 wt. %, at least 98 wt. %, or at least 95 wt. %, by weight of the total composition.

According to some embodiments, the oil-in-water emulsion is prepared in the presence of a non-ionic emulsifier, preferably having a hydrophile-lipophile balance (HLB) value between 12 to 18, 12 to 17, 12 to 16, 12 to 15, or 13 to 16 on a Griffin scale. Emulsions can be prepared by a number of emulsification techniques known to the skilled person. While manual shaking may suffice, various equipment, such as a vortex, an overhead stirrer, a magnetic stirrer, an ultrasonic disperser, a high shear homogenizer, a sonicator and a planetary centrifugal mill, to name a few, can be used, typically providing more homogenous populations of oil droplets in the aqueous phase. The emulsion can be readily applied following its preparation or within a time period during which it remains suitably stable. For instance, the emulsion can be applied as long as the oil droplets are within their desired size range and providing that the emulsified amino-silicone pre-polymers remain reactive. As the thickness of the coat is believed to be proportional to the average diameter of the droplets, too large droplets are to be avoided if a thin coat is desired, while on the other hand too small droplets would not be able to embed pigment particles having sufficient size to provide for the desired visual effect. This time window may vary with the constituents of the emulsion and their respective amounts, the presence of an emulsifier typically extending it. In some embodiments, the emulsion is applied to the textile fibers within at most 30 minutes from its emulsification, or within at most 20 minutes, at most 10 minutes, or at most 5 minutes.

According to some embodiments, the aqueous carrier comprises at least 60% water by weight of the liquid carrier, or at least 65 wt. %, or at least 70 wt. %, or at least 75 wt. %, or at least 80 wt. %, or at least 85 wt. %, or at least 90 wt. %, or at least 95 wt. % water. In some embodiments, the total concentration of the water and any emulsifier is at least 90 wt. %, at least 95 wt. %, at least 97 wt. % at least 99 wt. %, by weight of the aqueous phase. In cases in which the amount of pigments and/or their density is high, while the liquid carrier will predominantly comprise water, the water may constitute only 30% by weight of the total composition.

In some embodiments, a thickness or average thickness, or multiple-substrate average thickness of the amino-silicone coat, after curing, is at least 20 nm, at least 50 nm, or at least 100 nm, and optionally, at most 25 µm, at most 20 µm, at most 15 µm, at most 10 µm, at most 5,000 nm, at most 3,000 nm, at most 2,000 nm, at most 1,200 nm, at most 800 nm, at most 500 nm, at most 400 nm, at most 300 nm, at most 200 nm, at most 150 nm, or at most 120 nm, and further optionally, within a range of 20 nm to 25 µm, 20 nm to 20 µm, 20 nm to 15 µm, 20 nm to 10 µm, 20 nm to 5,000 nm, 20 nm to 3,000 nm, 20 nm to 1,000 nm, 20 nm to 500 nm, 20 nm to 300 nm, 20 nm to 200 nm, 20 nm to 150 nm, 50 nm to 150 nm, 50 nm to 500 nm, 50 nm to 350 nm, 50 nm to 250 nm, or 50 nm to 200 nm.

As used herein, the term "average thickness", typically with respect to one or more coatings or layers, is meant to refer to an arithmetic average of a measured thickness of the one or more coatings or layers, along the length of an external surface of a textile substrate (e.g., thread, yarn or even woven or unwoven fabric). Each individual thickness measurement can be made using a Focused Ion Beam (FIB) technology, as is known in the art. Ten equally spaced points along the length of the coated substrate are determined for the individual thickness measurements, and the arithmetic average of the ten measurements defines the average thickness pertaining to the individual substrate.

The coated textile fibers of, or produced by, the present invention, may exhibit fairly consistent coating thicknesses, irrespective, to a large degree, of the particular, local topographical features of the textile fibers substrate. Moreover, individual coated threads or yarns may exhibit similar coating thicknesses. Nonetheless, it will be appreciated that a more statistical approach to coating thicknesses may better serve to distinguish between the invention and various teachings of the art. Thus, in some embodiments of the present invention, a "multiple-substrate average thickness" of multiple longitudinal samples of textile substrates is defined as the "average thickness" as defined above for an individual coated fiber, but applied to a plurality of at least ten of such coated samples of textile substrates, such as threads, yarns or fabric samples, selected at random from the ones subjected together to the coating treatment, and arithmetically averaged over the plurality of said samples.

The Polymeric Overcoat

The polymeric layer is formed from an aqueous dispersion containing a plurality of polymeric particles, formed of a hydrophilic polymeric material having neutralized acid moieties, the hydrophilic polymeric material optionally enveloping pigment particles, when pigments are present in the aqueous dispersion.

The polymeric particles being dispersed in the aqueous dispersion are somewhat hydrophilic at the time of application to the textile fibers pre-coated with an amino-silicone coat, their acid moieties being neutralized for this purpose in presence of a neutralizing agent. However, the polymeric material before such neutralization of neutralizable acid moieties is hydrophobic. Following the application of the aqueous dispersion to the external surface of the amino-silicone pre-coated textile fibers, the neutralizing agent is eliminated (e.g., by evaporation), producing an overlying, polymeric layer (optionally pigmented) adhering to the external surface of the amino-silicone coat (pre-coated on the textile fibers).

As used herein in the specification and in the claims section that follows, the term "hydrophilic polymer", with respect to a polymeric material such as a neutralized polymeric material, refers to a polymer having at least one of the following solubility properties: (i) a solubility in pure deionized water of at least 1% (and more typically, at least 1.5%, at least 2%, at least 3%, at least 5%, at least 10%, or at least 15%), by weight, at 23° C.; and (ii) a solubility of at least 1% (and more typically, at least 1.5%, at least 2%, at least 3%, at least 5%, at least 10%, or at least 15%), by weight, in pure deionized water adjusted to a pH of 10, and at 23° C. The solubility of the polymer is assessed in absence of pigment or any other possible additive.

Typically, the conjugate acid of the hydrophilic, neutralized polymeric material is a hydrophobic polymeric material.

As used herein in the specification and in the claims section that follows, the term "solubility", with respect to a polymeric material, refers to the amount of polymeric material that can be introduced into the deionized water media of (i) or (ii) above, while maintaining the clarity of the deionized water media.

As used herein in the specification and in the claims section that follows, the term "clarity", with respect to a solution, is meant to include a solution having at least one, and typically both of the following properties: (i) the solution appears clear to the naked eye; and (ii) the average diameter or particle size (as determined by DLS) of any micelles disposed therein is at most 100 nm. More typically such micelles will have an average diameter or particle size of at most 80 nm, at most 70 nm, or at most 50 nm. Removal of the volatile base from the aqueous dispersions, causes the neutralized acidic moieties in the hydrophilic polymeric material to re-acidify into the conjugate acid thereof. Thus, a hydrophobic polymeric material can be obtained following such elimination.

Advantageously, the basic pH of the aqueous dispersion, once applied on textile fibers pre-coated with an amino-silicone film, can restore the positive charge of the amino-silicone film (e.g., by way of protonation of the amino groups). In parallel, the basic pH enables a high negative charging of the polymeric material (e.g., by way of protonation of the carboxylic groups). Thus, the basic pH of the aqueous dispersions favors a significant gradient of charge at the beginning of the coating process of the amino-silicone film by the polymeric particles, providing for a strong initial electrostatic drive.

In some embodiments, the neutralizable acid moieties of the hydrophobic polymeric material make up at least 8%, at least 10%, at least 12%, at least 15%, at least 16%, at least 17%, at least 18%, at least 19%, at least 20%, at least 21%, or at least 22%, by weight, of said hydrophobic polymeric material. In some embodiments, the neutralizable acid moieties of the hydrophobic polymeric material make up 8 to 30%, 10 to 30%, 12 to 30%, 12 to 28%, 12 to 26%, 15 to 30%, 15 to 28%, 15 to 26%, 17 to 22%, 17 to 23%, 18 to 30%, 18 to 28%, 18 to 26%, 20 to 30%, 20 to 28%, or 20 to 26%, by weight, of said hydrophobic polymeric material In some embodiments, the neutralizable and/or neutralized acid moieties of the hydrophilic polymeric material make up at least 8%, at least 10%, at least 12%, at least 15%, at least 16%, at least 17%, at least 18%, at least 19%, at least 20%, at least 21%, or at least 22%, by weight, of said hydrophilic polymeric material. In some embodiments, the neutralizable and/or neutralized acid moieties of the hydrophilic polymeric material make up 8 to 30%, 10 to 30%, 12 to 30%, 12 to 28%, 12 to 26%, 15 to 30%, 15 to 28%, 15 to 26%, 17 to 22%, 17 to 23%, 18 to 30%, 18 to 28%, 18 to 26%, 20 to 30%, 20 to 28%, or 20 to 26%, by weight, of said hydrophilic polymeric material. Such values are also reported in terms of percent weight content of monomer having acid moieties per total weight of the polymeric material (e.g., the Acrylic Acid (wt. % AA) in EAA copolymers or the Methacrylic Acid (wt. % MA) in EMAA). Such characteristics of a polymeric material are generally provided by the manufacturer, but can be assessed by standard methods, such as described in ASTM D 4094.

In some embodiments, the polymeric material has (prior to neutralization) an acid number of at least 100 mg KOH/g, at least 115 mg KOH/g, at least 130 mg KOH/g, or at least 145 mg KOH/g. In some embodiments, the acid number of the polymeric material is at most 230 mg KOH/g, at most 215 mg KOH/g, at most 200 mg KOH/g, or at most 185 mg KOH/g. In some embodiments, has an acid number within a range of 100 to 230 mg KOH/g, 115 to 215 mg KOH/g, 130 to 200 mg KOH/g, 130 to 185 mg KOH/g, 145 to 185 mg KOH/g, or 145 to 170 mg KOH/g. The Acid Number (also termed Acid Value or Neutralization Value, which assesses the amount of carboxylic acid groups in a chemical compound, and corresponds to the mass of potassium hydroxide (KOH) in milligrams that is required to neutralize one gram of the polymeric material). The acid number is generally provided by the manufacturers of such polymeric materials, or can be independently assessed by standard methods, such as described in ASTM D 974-04.

In some embodiments, the polymeric material is dispersed within the aqueous dispersion in an amount of at least 1 wt. %, at least 2 wt. %, or at least 5 wt. %, by weight of the aqueous dispersion. In some embodiments, the polymeric material is dispersed in the aqueous dispersion in an amount of at most 45 wt. %, at most 30 wt. %, at most 25 wt. %, at most 20 wt. %, at most 15 wt. %, at most 12.5 wt. %, or at most 10 wt. %, by weight of the aqueous dispersion.

In some embodiments, the aqueous dispersion is produced by:
(a) mixing in an aqueous carrier containing water at least one hydrophobic polymeric material each independently having neutralizable acid moieties, the hydrophobic polymeric material(s) being optionally compounded with a pigment, so as to form a neutralizable mixture including pellets of the hydrophobic polymeric material(s);
(b) adding to the neutralizable mixture a neutralizing agent, said addition being performed under agitation at a temperature above at least one of the highest of the softening temperature and/or of the melting temperature of the at least one hydrophobic polymeric material, said neutralizing agent being added in an amount sufficient to neutralize at least 75% of the neutralizable acid moieties of said polymeric material(s), so as to form a neutralized mixture including a portion of hydrophilic polymeric material(s); and
(c) dispersing the neutralized mixture, so as to form said aqueous dispersion, the aqueous dispersion including particles of at least one hydrophilic polymeric material.

In some embodiments, the aqueous dispersion is produced by:
(a) mixing in an aqueous carrier containing water at least one hydrophobic polymeric material each independently having neutralizable acid moieties, so as to form a neutralizable mixture including pellets of the hydrophobic polymeric material(s);
(b) adding to the neutralizable mixture a neutralizing agent, said addition being performed under agitation at a temperature above at least one of the highest of the softening temperature and/or of the melting temperature of the at least one hydrophobic polymeric material, said neutralizing agent being added in an amount sufficient to neutralize at least 75% of the neutralizable acid moieties of said polymeric material(s), so as to form a neutralized mixture including a portion of hydrophilic polymeric material(s);
(c) adding at least one pigment to the neutralized mixture; and
(d) dispersing the pigmented neutralized mixture, so as to form said aqueous dispersion, the aqueous dispersion including particles of at least one hydrophilic polymeric material, a portion of said hydrophilic polymeric material at least partially enveloping said at least one pigment.

While the amount of neutralizing agent can be experimentally determined by simple means, its concentration allowing for the self-dispersibility of the polymeric particles and (in absence of pigments) for the formation of a clear dispersion of micelles, it can also be estimated by equations. For instance, the amount of neutralizing agent (B—weight in grams) to be added to a polymeric material having neutralizable acid moieties is:

$$B=(W \cdot A \cdot N \cdot E)/1000$$

Where W is the weight of the polymeric material in grams,
A is the acidity of the polymeric material in mEq/gram of polymeric material,
N is the percent of neutralization desired, in decimal terms from 0 to 1, the latter representing 100% neutralization, and
E is the Equivalent weight of the neutralizing agent being used.

In some embodiments, the neutralizing agent used in the preparation of the aqueous dispersion is a volatile base. In such case, the resulting aqueous dispersion contains a volatile base. The volatile base can be an amine base, selected from the group consisting of ammonia ($NH_3$), monoethanolamine, diethanolamine, triethanolamine and morpholine, or a metal base selected from sodium hydroxide and potassium hydroxide. When wash-resistance is desired, alkaline metal bases are preferably avoided as neutralizing agents, as the acid moiety of the polymeric material may recombine with the metal ion of the base resulting in ionomers being less resistant to water In some embodiments, the hydrophilic polymeric material having neutralized acid moieties, has a solubility of at least 2%, at least 5%, at least 10%, or at least 15%, by weight, or wherein said solubility is within a range of 2 to 30%, 5 to 30%, 10 to 30%, or 15 to 30%, by weight, at a pH of 10.

In some embodiments, the aqueous dispersion and the particles of hydrophilic polymeric material further include pigment particles dispersed therein, the pigments being optionally selected from the previously detailed lists and further optionally fulfilling the structural features relating thereto (e.g., size of particles).

In some embodiments, pigments are present in the aqueous dispersion in an amount of at least 0.1 wt. %, at least 0.5 wt. %, at least 1 wt. %, at least 2 wt. %, or at least 5 wt. %, by weight of the hydrophilic polymeric material. In some embodiments, the pigments are in the aqueous dispersion in an amount of at most 50 wt. %, at most 40 wt. %, at most 30 wt. %, at most 20 wt. %, at most 15 wt. %, or at most 10 wt. %, by weight of the hydrophilic polymeric material. In some embodiments, the pigments are present in the aqueous dispersion in an amount within a range of 0.1 wt. % to 50 wt. %, 1 wt. % to 30 wt. %, 2 wt. % to 20 wt. %, or 5 wt. % to 15 wt. %, by weight of the hydrophilic polymeric material.

In some embodiments, pigments are present in the aqueous dispersion in an amount of at least 0.05 wt. %, at least 0.5 wt. %, or at least 1 wt. %, by weight of the aqueous dispersion. In some embodiments, the pigments are in the aqueous dispersion in an amount of at most 15 wt. %, at most 10 wt. %, at most 7.5 wt. %, at most 5 wt. %, or at most 2.5 wt. %, by weight of the aqueous dispersion. In some embodiments, the pigments are present in the aqueous dispersion in an amount within a range of 0.05 wt. % to 15 wt. %, 0.5 wt. % to 10 wt. %, 1 wt. % to 7.5 wt. %, 1.5 wt. % to 5 wt. %, or 1.5 wt. % to 2.5 wt. %, by weight of the aqueous dispersion.

In some embodiments, the method of treating an external surface of textile fibers having an amino-silicone coating, with the aqueous dispersions of at least partly neutralized polymeric material, further comprises volatizing the volatile base associated with the overlying polymeric layer (optionally pigmented), so as to acidify, largely or mainly acidify, or completely acidify the neutralized acid moieties.

Following the application of the aqueous dispersion, the method further comprises converting a portion of, a major portion of, or all of the hydrophilic polymeric material in the overlying, pigmented polymeric layer, into a conjugate acid thereof. In some embodiments, the converting includes, mainly includes, or consists of acidifying the neutralized acid moieties to form the conjugate acid.

Once the hydrophilic polymeric material is sufficiently converted into a conjugate acid thereof, a hydrophobic polymeric material is obtained. Hence a polymeric layer wherein the polymeric material has sufficiently converted from a form having acid moieties by a base (hydrophilic) to a conjugate acid form (hydrophobic) can form sufficient attachment to the underlying amino-silicone coat. At such time, the external polymeric coat is a hydrophobic coat.

In some embodiments, the polymeric material having the neutralized acid moieties includes, mainly includes, consists essentially of, or consists of one or more neutralized copolymer selected from the group consisting of neutralized alkene-acrylic acid copolymer, neutralized alkene-methacrylic acid copolymer and neutralized acrylamide/acrylate copolymer.

In some embodiments, the neutralized alkene-acrylic acid copolymer includes, mainly includes, consists essentially of, or consists of neutralized ethylene-acrylic acid (EAA) copolymer. In some embodiments, the neutralized alkene-methacrylic acid copolymer includes, mainly includes, consists essentially of, or consists of neutralized ethylene-methacrylic acid (EMAA) copolymer. In some embodiments, the polymeric material having the neutralized acid moieties includes, mainly includes, consists essentially of, or consists of neutralized acrylamide/acrylate (AAA) copolymer.

At a pH within a range of 7.5 to 11, suitable hydrophilic polymeric material is self-dispersible in water, in an absence of dispersants and all other additives in water.

In some embodiments, the aqueous dispersion of neutralized hydrophilic polymeric material further comprises a surfactant and/or a thickener. In some embodiments, the surfactant is a super-wetting agent able to modify the surface tension of the aqueous dispersion, facilitating its wetting of an amino-silicone coat.

In some embodiments, the surfactant or super-wetting agent in the aqueous dispersion is selected and added in sufficient quantity whereby the aqueous dispersion exhibits a surface tension, at 25° C., of at most 30, at most 28, at most 26, or at most 24, and optionally, at least 12, at least 14, or at least 16 milliNewtons per meter (mN/m). In some embodiments, the surface tension of the aqueous dispersion is within a range of 12 to 30, 15 to 30, 18 to 28, 18 to 26, 18 to 24, 19 to 24, or 20 to 24 mN/m.

Suitable hydrophobic polymeric material having neutralizable acid moieties, such as acrylic acid (AA) or methacrylic acid (MAA), which can serve for the preparation of aqueous dispersions according to the present disclosure can be commercially available, including, by way of non-limiting examples, some EAA, EMAA and AAA polymeric materials commercialized under the tradenames Primacor™ of Dow Chemical Company, Nucrel® of DuPont, Joncryl® and Luwax® of BASF, Dermacryl® of AkzoNobel and Escor™ of ExxonMobil Chemical.

Suitably, the hydrophobic polymeric material having neutralizable acid moieties is thermoplastic. Thermoplastic polymers facilitate, for instance, the partial envelopment of pigment particles in compounding processes, such as hot melt compounding In some embodiments, subsequent to the application of the aqueous dispersion onto the amino-silicone coat, the overlying polymeric layer is treated, so as to produce an overlying, (e.g., pigmented) polymeric coating adhering to the external surface of the pre-coated textile fibers. The post-application treatments include washing and/or carding the fibers to remove excess material therefrom, and optionally, subsequently drying and/or carding of the fibers.

The temperature at which the coated textile fibers are generally treated (e.g., washed and/or dried) depends on the softening or melting point of the polymeric particles. The treatment of the coated textile fibers is typically performed at a temperature of at most 45° C., 40° C., 35° C., 30° C., or 25° C. In some embodiments, such steps are performed at a temperature of at least 5° C., 10° C., 12° C., 15° C., 17° C., or 20° C., and optionally, within 7° C., 5° C. or 3° C. of room or ambient temperature.

In some embodiments, the washing of the textile fibers is performed within at most 20 minutes, at most 10 minutes, at most 5 minutes, at most 3 minutes, at most 2 minutes, at most 1 minute, or at most 30 seconds after completing the application of the aqueous dispersion.

In some embodiments, the drying of the textile fibers and coats thereon is an active drying. In some embodiments, a total time period for applying the aqueous dispersion, washing and/or actively drying the textile fibers is within a range of 2 to 90 minutes, 2 to 75 minutes, 2 to 60 minutes, 2 to 45 minutes, 2 to 30 minutes, 2 to 20 minutes, 2 to 10 minutes, or 2 to 5 minutes.

In some embodiments, within 24 to 72 hours, within 24 to 48 hours, within 24 to 36 hours, or within 24 to 30 hours immediately succeeding the total time period (e.g., following washing or drying), and while the textile fibers are maintained within 7° C., 5° C., 3° C., or 1° C. of room or ambient temperature, the overlying, pigmented polymeric coating achieves wash resistance, permanence, or permanent coloration.

It is believed that such resilience of the overlying polymeric coating is contributed by the resistance of the underlying amino-silicone coat and the strength of its attachment to the underneath textile fibers. It can be noted that since curing of the amino-silicone coat can proceed on the textile fibers, once such coats are enveloped by the polymeric layer, and as condensation-curing can benefit from ambient humidity, the overlying polymeric coating is advantageously permeable to diffusion of humidity.

In some embodiments, the thickness of the overlying polymeric coat is such that when combined with the thickness of an underlying amino-silicone coat a total thickness, total average thickness, or total multiple-substrate average thickness of said amino-silicone coat and said overlying pigmented polymeric coating, is at least 100 nm, at least 150 nm, at least 200 nm, at least 300 nm, at least 500 nm, at least 800 nm, at least 1,200 nm, or at least 2,000 nm. In some embodiments, the total thickness, total average thickness, or total multiple-substrate average thickness of the two coats is at most 50 µm, at most 40 µm, at most 30 µm, at most 20 µm, at most 10 µm, at most 5,000 nm, at most 3,500 nm, at most 2,500 nm, at most 2,000 nm, at most 1,700 nm, or at most 1,400 nm. In some embodiments, the total thickness, total average thickness, or total multiple-substrate average thickness of the two coats is within a range of 100 nm to 50 µm, 100 nm to 40 µm, 100 nm to 30 µm, 100 nm to 20 µm, 100 nm to 10 µm, 100 nm to 5,000 nm, 200 nm to 3,500 nm, 200 nm to 2,500 nm, 200 nm to 1,000 nm, 200 nm to 700 nm, 200 nm to 500 nm, 200 nm to 450 nm, or 200 nm to 400 nm.

In some embodiments, a ratio of at least one of said total thickness and said total average thickness and said total multiple-substrate average thickness of the combined two coats to said thickness, average thickness, or multiple-substrate average thickness of the underlying amino-silicone layer, is within a range of 1.2:1 to 100:1, 1:4 to 100:1, 1:7 to 100:1, 2:1 to 100:1, 3:1 to 100:1, 4:1 to 100:1, 5:1 to 100:1, 7:1 to 100:1, 10:1 to 100:1, 2:1 to 30:1, 2:1 to 20:1, 3:1 to 30:1, 3:1 to 20:1, 5:1 to 30:1, 5:1 to 20:1, 7:1 to 30:1, 7:1 to 20:1, 10:1 to 50:1, 10:1 to 30:1, or 10:1 to 20:1.

According to some embodiments, the compositions according to the present teachings (or the kits enabling their preparation and use) further comprise at least one additive selected from the group consisting of dispersant, pH modifying agents, preservatives, bactericide, fungicide, viscosity modifiers, thickeners, chelating agents, vitamins and perfumes. Depending on the mode of application, additional agents can be required, for instance, a propellant can be added if the composition is to be applied as a propelled spray.

According to some embodiments, the composition is in the form selected from the group consisting of a paste, a gel, a lotion, and a cream.

Textile fibers coated according to the methods of the present invention can be characterized by the following structural features. First the fibers are coated, which is not necessarily the case for conventionally treated or colored fibers (e.g., wherein dies are entrapped within the fibers rather than on their external surface). Secondly, this external coat consists of two distinct layers. The presence of two layers on the external surface of textile fibers can be assessed by standard microscopy techniques, for instance by FIB-SEM or TEM. The first layer (adjacent to the fiber) and the second layer (distal from the fiber, forming the outermost surface of the coating) can each have a thickness of at least 50 nm and up to 25 µm. The coating, consisting of the first and second layer, can have a thickness of at least 100 nm and up to 50 µm.

The first layer of a coating according to the present teaching is directly disposed on and is in contact with the textile fibers. It is produced from the oil phase containing the at least one reactive condensation-curable film-forming amino-silicone pre-polymer, as described above. The first layer, resulting from curing of the curable components provided in the oil phase, comprises cross-linked amino-silicones, rendering the first layer thermosetting in nature, therefore, this cured layer of the coating may be referred to as the thermosetting layer.

While amino silicones may possibly be included in products coming into contact with textile fibers, they typically would not be cross-linked nor intended to form a continuous wash resistant film or an underlayer for an additional outermost layer. The presence of amino-silicones in a first layer of a coating according to the invention can be detected by standard methods, such as FTIR, whereby the presence of characteristic bonds such as silicone-oxygen or silicone-nitrogen can be detected. As these materials are cross-linked, the first layer of the coating can be additionally characterized by having a glass transition temperature, as measurable by standard thermo-analytical methods, for instance using differential scanning calorimetry (DSC). In some embodiments, the thermosetting layer has a Tg between −100° C. and +20° C., between −80° C. and +15° C., between −60° C. and +10° C., between −40° C. and +5° C., or between −20° C. and +5° C. The thermosetting layer can be further characterized by silicone Nuclear Magnetic Resonance (NMR), which can provide information about the nature of the repeating units in the cured silicone elastomer.

Other non-volatile, non-reacted constituents, which were previously described with respect to the oil-in-water emulsion applied to form a first coat may additionally be detected in the first layer by standard analytical methods, such as the presence of pigments or reinforcement fillers, by way of example.

The second layer is disposed on the first thermosetting layer, and it is thermoplastic in nature, and therefore, the second layer of the coating may be referred to as the thermoplastic layer. It is produced from the aqueous dispersion containing the plurality of polymeric particles described above, formed of the hydrophilic polymeric material having neutralized acid moieties. The polymeric material in the second layer comprises neutralizable acid moieties (detectable by FTIR), that can make up 8 to 30%, 10 to 30%, 12 to 30%, 12 to 28%, 12 to 26%, 15 to 30%, 15 to 28%, 15 to 26%, 17 to 22%, 17 to 23%, 18 to 30%, 18 to 28%, 18 to 26%, 20 to 30%, 20 to 28%, or 20 to 26%, by weight of the thermoplastic layer.

As the acid moieties of the polymer of the thermoplastic second layer might have been at least partially neutralized in the presence of a non-volatile neutralizing agent such as metal ion-based neutralizing agents, in particular alkali metals (e.g., sodium hydroxide, potassium hydroxide, etc.), in some embodiments the second outermost thermoplastic layer can be further characterized by the presence of metal ions. The metal ions that may remain in the second layer as a trace of metal ion-based agents having served to neutralize the polymer of the aqueous dispersion can be detected by any method known in the art, such as by Scanning Electron Microscopy with Energy Dispersive Spectroscopy (SEM/EDS). Other non-volatile, non-reacted constituents, which were previously described with respect to the aqueous dispersion applied to form a second coat may additionally be detected in the second layer by standard analytical methods.

The thermoplastic layer exhibits a melting temperature (Tm), measurable by DSC, between 50° C. and 250° C., between 60° C. and 200° C., between 70° C. and 150° C., between 70° C. and 100° C., between 70° C. and 90° C., or between 70° C. and 80° C.

While the above-mentioned Tm may in part seem low as compared to temperatures conventionally experienced by textile fibers (e.g., during washing at elevated temperature or during ironing), such temperatures are not expected to harm the external polymeric coating, as their relatively low thickness would enable their rapid cooling to regain their original structure.

Additional methods that may be used for the characterization of the thermoplastic layer include X-ray Photoelectron Spectroscopy (XPS), a non-destructive method, whereby the polymeric chemistry (e.g., the acid nature of the polymers) on the surface of the coated fiber can be identified. Carbon NMR can also be used to detect and quantify carbons that are linked to acid moieties.

According to some embodiments, the coating further comprises a pigment, optionally as a plurality of sub-micronic pigment particles. The pigment can be present in the thermosetting layer and/or in the thermoplastic layer. The pigments, when present in any of the layers of the coating, are as described above.

When analysis of a coated fiber is desired, the two layers of the coating can be separated from one another and from the underlying fiber as follows:

First, the external thermoplastic polymeric layer can be dissolved by placing the coated fiber in a suitable solvent for sufficient time to allow the dissolution of the outer layer into the solvent. Such solvent can be, e.g., tetrahydrofuran (THF) or dimethyl sulfoxide (DMSO). The solvent can then be evaporated and the residual mixture including the polymeric material which forms the thermoplastic layer can be separately analyzed, such as by methods described above.

The inner thermosetting layer is a solid layer resistant to the solvent used for the dissolution of the outermost thermoplastic layer. Its removal from the fiber, if so desired for the sake of specific analysis, can be mechanical, e.g., by scraping the fibers to remove flakes of the rigid layer. The flakes of the thermosetting layer so collected can then be separately analyzed, such as by methods described above.

Textile fibers characterized by a coating consisting of two layers as afore-described can be keratinous or non-keratinous, natural or synthetic fibers, as previously detailed.

In some embodiments, the compositions of the present invention, when applied to colored textile fibers, are used to reduce, delay or prevent fading or color loss of fibers that undergo numerous washings, as textiles conventionally do. The coating formed on the textile fibers is believed to prevent the dye coloring the fibers from leaking out—a common result of washing clothes—and thus the original vivid colors of the colored textiles can be maintained. When referring to reduction, delay or prevention of fading, these effects can be analyzed by spectrophotometry, e.g., by measuring the color difference (ΔE, derived from CIE L*a*b* color space values) between the newly coated fibers and the same fibers after numerous washing cycles. Textile fibers, coated by the compositions of the present invention, display a ΔE of less than 3 after 10 washes.

EXAMPLES

Materials

The materials used in the following examples are listed in Table 1 below. The reported properties were retrieved or estimated from the product data sheets provided by the respective suppliers or assessed by routine analytical methods. Unless otherwise stated, all materials were purchased at highest available purity level. In the following table, AA stands for Acrylic Acid, AN stands for Amine Number, EAA stands for Ethylene Acrylic Acid, N/A means that the information is not available, PDMS stands for polydimethylsiloxane, 2-SiOH and 3+SiOH mean that a pre-polymer has, respectively, two, or three or more hydrolysable reactive groups and/or silanol groups per molecule, and molecular weight (MW) when used in relation with polymers refers to weight average molecular weight. Regarding the suppliers of these materials, BASF stands for BASF Corporation, USA, Dow stands for Dow Chemical Company, USA, Evonik stands for Evonik Resource Efficiency GmbH, Germany, Gelest stands for Gelest Inc., USA, Genesee stands for Genesee Polymer Corporation, USA, Heubach stands for Heubach Colour Pvt., India, Momentive stands for Momentive Performance Materials, USA, Shin Etsu stands for Shin Etsu Chemical Company Ltd, Japan, Sigma-Aldrich stands for Sigma-Aldrich Corporation, USA, and Univar stands for Univar BV, United Kingdom.

TABLE 1

| Name/properties | Material Name | MW | Supplier | CAS No. |
|---|---|---|---|---|
| Reactive amino-silicone pre-polymers | | | | |
| 2-SiOH polymer AN: 127 | KF-857 | ~3,200 | Shin Etsu | N/A |
| 2-SiOH polymer AN: 11 | GP-145 | ~018,052 | Genesee | N/A |
| Mixture of 3 + SiOH monomers AN: 235-450 (370) | Dynasylan ® SIVO 210 | 221-425 | Evonik | 919-30-2 13497-18-2 1184179-50-7 |
| 3 + SiOH monomer AN: 450 | Dynasylan ® AMEO | 221.4 | Evonik | 919-30-2 |

TABLE 1-continued

| Name/properties | Material Name | MW | Supplier | CAS No. |
|---|---|---|---|---|
| 3 + SiOH monomer AN: 235 | SIB1824.5 | 425.7 | Gelest | 13497-18-2 |
| 3 + SiOH monomer AN: 263 | SIT8187.2 | 379.6 | Gelest | 1184179-50-7 |
| 3 + SiOH Oligomer AN: 277 | Silquest ® VX-225 | ~670-4,500 | Momentive | N/A |
| Oligomer AN: 280 | Silquest ® Y-15744 | ~630-12,000 | Momentive | N/A |
| Non-reactive amino-silicones | | | | |
| 1,3-bis (3-aminopropyl) tetramethyldisiloxane AN: ~805 | GP-967 | 248.5 | Genesee | 2469-55-8 |
| Bis 3-aminopropyl-terminated PDMS AN: ~200 | GP-965 | 1,000 | Genesee | 106214-84-0 |
| Non-amino silicones | | | | |
| Methyltrimethoxysilane | MTMS | 136.22 | Sigma-Aldrich | 1185-55-3 |
| Hexamethyldisiloxane | M2 | 161.38 | Gelest | 107-46-0 |
| Methyltriethoxysilane | MTES | 178.3 | Sigma-Aldrich | 2031-67-6 |
| Reactive filler | | | | |
| Hydrophobic fumed silica | Aerosil ® R 8200 | N/A | Evonik | 68909-20-6 |
| Surfactant | | | | |
| Polyoxyethylene (20) sorbitan mono-oleate | Tween ® 80 | 1,310 | Sigma-Aldrich | 9005-65-6 |
| Thermoplastic neutralizable acid-polymers | | | | |
| EAA copolymer AA content 20.5 wt. % | Primacor ™ 5990I | >>1,000 | Dow | 9010-77-9 |
| EAA copolymer AA content 21.5 wt. % | Luwax ® EAS-5 | >>1,000 | BASF | 25053-53-6 |
| Pigment | | | | |
| Pigment Violet 23 (CI 51319) | Chromophtal ® Violet K5800 | 589.48 | BASF | 215247-95-3 |
| Pigment Orange 43 (CI 71105) | Hostaperm ® Orange GR | 412.40 | Univar | 4424-06-0 |
| Pigment Red 122 (CI 73915) | Heuco ® Red 312201 | 340.38 | Heubach | 980-26-7 |
| Neutralizing agent | | | | |
| Ammonium hydroxide (NH$_4$OH) | Ammonium hydroxide | 35.05 | Sigma-Aldrich | 1336-21-6 |

Equipment

The equipment used in the following examples shall be detailed at first occurrence. Unless otherwise stated, a same apparatus shall refer to the first described instrument.

Example 1: Pre-Treatment of a Reactive Amino-Silicone Oil Phase and Constituents Thereof In this example, the contribution of water content of ingredients of a hair coating composition was studied. As explained in the previous description, it is believed that minor amounts of water in the reactive phase of condensation-curable amino-silicone emulsions may trigger or improve the rate of hydrolysis of the hydrolysable moieties of the amino-silicone pre-polymers, increasing in turn the condensation-curing of the resulting silanol moieties.

As used herein, the term "reactant" relates to any and all ingredients of the composition, independent of their chemical identity, whether reactive or non-reactive with respect to the ultimate condensation-curing of an amino-silicone coat prepared using the composition.

Water Desorption

In a first stage, all reactants were dried. Solid reactants, such as a reactive filler, were dried for 24 hours at 150° C. in a drying and convection oven (Mechanical Convection Oven DFO-240N by MRC, Israel). Liquid reactants were dried using porous silica molecular sieves having uniform pores of about 4 Angstroms to reduce presence of water to minimal water content (below which molecular sieves are no longer able de desorb residual water). Before use, the molecular sieves were dried in a ceramic oven (SNOL 30/1300 LSF01, Snol, Lithuania) at a temperature of 350° C. for 3 hours and allowed to cool back to RT in a desiccator under dry argon atmosphere. The material to be dried was placed in a container of appropriate volume, to which the dried molecular sieves were added so as to occupy about ⅔ of the volume when combined with the material. After 24 hours of incubation, the dried material was separated from the molecular sieves by filtration. Each dried reactant was individually stored at RT in a desiccator under argon atmosphere, so as to maintain the respective residual water amount of each anhydrous reactant to its minimum until use.

The residual amount of water in the dried (anhydrous) reactants can be determined, by way of example, by Karl Fisher titration. For instance, the residual amount of water in the reactive hydrophobic fumed silica was found to be of 0.4 wt. % using a C30 coulometer by Mettler-Toledo and MilliporeSigma 1.09257.0500 Aquastar® CombiCoulomat Fritless Reagent. Such result is in accordance with supplier data specifying that the material typically contains 0.5 wt. % water or less upon delivery. The non-reactive amino-silicone oils were similarly tested. GP-965, which contained about 0.007 wt. % water upon supply, was dried to contain about 0.006 wt. % water, both values being deemed comparable and indicative of the minimal residual amount of water that may be adsorbed by this oil. GP-967, which contained about 0.089 wt. % water upon supply, was dried to contain about 0.064%.

The residual amount of water in the reactive pre-polymers was assessed by FTIR spectroscopy, the spectrum of which was analyzed for the presence of a hydroxyl peak, at about 3600-3700 cm$^{-1}$, indicative of the hydrolysis of silanol moieties, and for the presence of water in the range of 3100-3700 cm$^{-1}$. In the present study, the FTIR analysis was performed in the mid-infrared range (approx. 500-4000 cm$^{-1}$) using a Nicolet™ 6700 FTIR (Thermo Electron Corporation) at a resolution of 4 cm$^{-1}$ and at 64 scans/sample. The samples tested were diluted to 5 wt. % in carbon tetrachloride. The absence of peak of hydrolysis in the relevant range was interpreted to mean the substantial absence of hydrolysis in the dried material, which in turn indicates a very low amount of water, if any, in the dried reactive pre-polymers. Reactive amino-silicones GP-145 and KF-857 were tested by this method and their respective spectra, both before and after drying with the molecular sieves, were devoid of peaks in the water and silanol ranges.

Controlled Water Adsorption

Water was added to the dried reactants of the first stage as follows. This controlled water addition or humidification was performed on reactive condensation-curable amino-silicone pre-polymers, on a reactive reinforcement filler and/or on non-reactive reactants. Reactants exposed to known amounts of water are termed herein pre-mix(es). The water used for the controlled humidification of the reactants was distilled water having a pH in the range of 6.5 to 7.5, hence also referred to as neutral water.

A series of pre-mixes of reactive condensation-curable amino-silicone pre-polymers containing predetermined amounts of water (0.1 wt. %, 0.3 wt. %, 0.5 wt. %, 1 wt. % and 3 wt. %) by weight of the pre-polymer was prepared by respectively placing in a 20 ml sealable glass vial: 0.01 g, 0.03 g, 0.05 g, 0.10 g, and 0.30 g of distilled water (pH 6.5-7.5) and 9.99 g, 9.97 g, 9.95 g, 9.90 g and 9.70 g of KF-857 or GP-145. Another pre-mix was prepared, of non-amino silicone pre-polymer supplemented with 12.5 wt. % water, by placing in a 20 ml sealable glass vial 1 g of distilled water and 7 g of MTMS. The respective amounts of water and reactants were weighted using a Cubis® analytical balance by Sartorius, Germany. The KF-857, GP-145 or MTMS pre-mix compositions were mixed by vortex (Vortex Genius 3, IKA, Germany) for about 10-30 seconds until homogeneity was achieved. The KF-857 or GP-145 pre-mixes were prepared immediately before incorporation of all reactants in a pre-treatment composition as detailed below. The vial containing the MTMS pre-mix composition was maintained open for 10 minutes, to allow evaporation of the methanol formed during the hydrolysis, furthering its progress, while gently shaken from time to time, and then the other reactants in the pre-treatment composition were added, as detailed below.

Similarly, a series of pre-mixes of non-reactive amino-silicones containing pre-determined amounts of water (0.1 wt. %, 0.3 wt. %, 0.5 wt. %, 1 wt. % and 3 wt. %) by weight of the amino-silicone oil was prepared by respectively placing in a 20 ml sealable glass vial: 0.01 g, 0.03 g, 0.05 g, 0.10 g, and 0.30 g of distilled water (pH 6.5-7.5) and 9.99 g, 9.97 g, 9.95 g, 9.90 g or 9.70 g of GP-967 or GP-965. The GP-967 or GP-965 pre-mix compositions were mixed by vortex for about 10 seconds until homogeneity was achieved. The GP-967 or GP-965 pre-mixes were prepared immediately before incorporation of all reactants in a pre-treatment composition.

A pre-mix of hydrophobic fumed silica containing 0.8 wt. % water by weight of the silica was prepared by placing the dried fumed silica under humid atmosphere into an oven. The dried fumed silica was incubated for 24 hours, at a temperature of 40° C. and 80% relative humidity (RH) in an oven (Mechanical Convection Oven DFO-240N by MRC, Israel). The amount of water in the hydrophobic fumed silica so treated, was determined by Karl Fisher titration and found to be of about 0.8 wt. % by weight of reactive fumed silica. For reference, the amount of water in the dried hydrophobic fumed silica before the controlled humidification treatment was of 0.4 wt. %.

The addition of water to a reactant was confirmed by FTIR spectroscopy, as previously detailed. Briefly, dried Dynasylan® SIVO 210 was supplemented with 0 wt. %, 2 wt. % and 5 wt. % of neutral distilled water and analyzed immediately following water addition. The spectrum of the dried Dynasylan® SIVO 210 was devoid of any peak in the ranges indicative of water and silanol. When this reactant was supplemented with either 2 wt. % or 5 wt. % of water, a narrow silanol peak and a wide water peak were detected. These results show that the water was adsorbed by the reactant and that the hydrolysis it can cause was readily triggered. When the reactant humidified with 2 wt. % water was tested again, 3 days after water addition, the peak characteristic of water was no longer visible, the peak of silanol groups remaining to indicate the hydrolysis which took place in the sample. These results indicate that the added water was fully "consumed" for the benefit of hydrolysis.

Pre-Treatment Compositions

Pre-Treatment Compositions 1-5 (PTC1-PTC5)

Into a 20 ml sealable glass vial, the following were placed:

0.23 g (2.23 wt. % by weight of the final mixture) of 0.8 wt. % water humidified hydrophobic fumed silica (Aerosil® R 8200);

0.27 g (2.62 wt. % by weight of the final mixture) of dried GP-145;

1.80 g (17.4 wt. % by weight of the final mixture) of the KF-857 reactive amino-silicone pre-mix containing 0.1 wt. % water (PTC1), 0.3 wt. % water (PTC2), 0.5 wt. % water (PTC3), 1 wt. % water (PTC4) or 3 wt. % water (PTC5); and 8.00 g (77.67 wt. % by weight of the final mixture) of dried Dynasylan® SIVO 210.

Pre-Treatment Compositions 6-8 (PTC6-PTC8)

Into a 20 ml sealable glass vial, the following were placed:

0.23 g (2.23 wt. % by weight of the final mixture) of 0.8 wt. % water humidified hydrophobic fumed silica (Aerosil® R 8200);

1.80 g (17.42 wt. % by weight of the final mixture) of dried KF-857;

0.30 g (2.9 wt. % by weight of the final mixture) of the GP-145 reactive amino-silicone pre-mix containing 0.1 wt. % water (PTC6), 0.3 wt. % water (PTC7) or 1 wt. % water (PTC8); and 8.00 g (77.44 wt. % by weight of the final mixture) of dried Dynasylan® SIVO 210.

Pre-Treatment Compositions 9-13 (PTC9-PTC13)

Into a 20 ml sealable glass vial, the following were placed:
2.00 g (20 wt. % by weight of the final mixture) of the GP-967 non-reactive amino-silicone pre-mix containing 0.1 wt. % water (PTC9), 0.3 wt. % water (PTC10), 0.5 wt. % water (PTC11), 1 wt. % water (PTC12), or 3 wt. % water (PTC13);
0.67 g (6.66 wt. % by weight of the final mixture) of dried GP-965; and
7.33 g (73.33 wt. % of the final mixture) of dried Dynasylan® SIVO 210.

Pre-Treatment Compositions 14-17 (PTC14-PTC17)

Into a 20 ml sealable glass vial, the following were placed:
0.67 g (6.67 wt. % by weight of the final mixture) of the GP-965 non-reactive amino-silicone pre-mix containing 0.1 wt. % water (PTC14), 0.3 wt. % water (PTC15), 1 wt. % water (PTC16), or 3 wt. % water (PTC17);
2.00 g (20 wt. % by weight of the final mixture) of dried GP-967; and
7.33 g (73.33 wt. % of the final mixture) of dried Dynasylan® SIVO 210.

Pre-Treatment Composition 18 (PTC18)

Into a 20 ml sealable glass vial, the following were placed:
0.23 g (2.23 wt. % by weight of the final mixture) of 0.8 wt. % water humidified hydrophobic fumed silica (Aerosil® R 8200);
0.27 g (2.62 wt. % by weight of the final mixture) of dried GP-145;
1.80 g (17.4 wt. % by weight of the final mixture) of dried KF-857; and
8.00 g (77.67 wt. % by weight of the final mixture) of dried Dynasylan® SIVO 210.

Small metal beads (having a diameter of 1.5 mm and made of stainless steel) were placed in each of the vials, to improve the homogeneity of the oil phase. The vials were capped, and the afore-described compositions were mixed in a Turbula® mixer (Willey A. Bachofen AG, Maschinefabrik, Germany) for 10 minutes until homogeneity was achieved. The homogenous mixtures were then subjected to shear to improve the dispersion of the fumed silica, when present, using a grinding ball mill (IKA Tube Drive) for 2 minutes at maximal speed of 6,000 rpm. The obtained mixtures were each divided into 4 samples, that were maintained for 0 hr, 2 hrs 4 hrs and 24 hrs at room temperature.

Pre-Treatment Composition 22 (PTC22)

Into a 20 ml sealable glass vial, the following were placed:
8 g (53.3% by weight of the final mixture) of the MTMS pre-mix supplemented with 12.5 wt. % water; and
2.00 g (13.3 wt. % by weight of the final mixture) of Dynasylan® AMEO The vial was sealed, and its contents mixed by vortex for 30 seconds, then opened and maintained for 2 hours, to allow evaporation of the ethanol formed during the hydrolysis, furthering its progress. Then 5.00 g (33.4 wt. % by weight of the final mixture) of M2 were added. The mixture was mixed by vortex for 10 seconds and kept in a closed vial for 5 days. All afore-said pre-treatment compositions led to the formation of a clear uniform oil phase (not turbid and without separation of the minute amounts of water to a distinct aqueous phase).

Analysis of Pre-Treatment Compositions

The viscosity of pre-treatment composition PTC3 was measured at the end of each of its incubation time using a Haake™ Mars™ rheometer (geometry DG41) at a shear rate of 1 sec$^{-1}$. The viscosity of the pre-treatment compositions was found to increase with time, PTC3 having an average viscosity of 9.7 mPa·s immediately following its preparation (t=0 hr), a viscosity of 10.0 mPa·s after 2 hrs, a viscosity of 10.2 mPa·s after 4 hrs and a viscosity of 24.4 mPa·s after 12 hrs. Thus after 12 hrs of pre-treatment, an increase of 151% in viscosity was observed.

The presence of a hydroxyl peak, indicative of the initiation of hydrolysis of the reactant including the hydrolysable moieties was assessed using FTIR spectroscopy, as described in connection with the analysis of the isolated reactants. The PTC3 composition was analyzed at time 0 and readily displayed a narrow silanol peak at this initial point in the pre-treatment, absent from a control composition lacking any added water.

The glass transition temperature, if any, of the PTC3 pre-treatment liquid composition was assessed by Differential Scanning calorimetry (DSC) performed following all time points of incubation till 24 hours. The samples were tested between −80° C. and +30° C. at a heating rate of about 10° C./minute. The results were plotted in terms of heat flow (J/s) versus temperature (° C.) over the scanned range. A flat curve indicated the absence of glass transition temperature, as expected from materials lacking a sufficiently cross-linked network, as detectable by a particular Tg. No Tg was detected for any of the pre-treatment incubation time between 0 and 24 hours.

It should be noted that once the pre-treatment composition is emulsified, the emulsion is generally applied within no more than 30 minutes from emulsification. Following such time, the ability to obtain satisfactory coloration and permanency decreases and, given sufficient delay, even disappears. PTC3 was emulsified as described in further details in Example 2. The emulsion was allowed to stand for 30 minutes at RT. The aged emulsion was then centrifuged to eliminate the aqueous phase and the oil phase was tested by DSC as above-described. The oil phase extracted from the aged emulsion displayed a Tg at about −1° C. While this glass transition temperature may not be representative of a fully cured film resulting from the reactants of the pre-treatment composition, the mere presence of a detectable Tg indicated that condensation curing took place so as to form a network in the aged emulsion.

Similar analysis were performed on a pre-treatment composition of the PTC9-17 series, wherein the neutral water was added at 2 wt. % on Dynasylan® SIVO 210 instead of being added to either GP-965 or GP-967. The resulting pre-treatment composition was termed PTC21. The viscosity of this pre-treatment composition was of about 6.1 mPa·s immediately following its preparation (t=0 hr) and of about 8.3 mPa·s after 24 hrs, providing in percentage a viscosity increase of about 35% as compared to W.

DSC analysis of liquid PTC21 for the determination of Tg of the pre-treatment composition, if any, was performed at all time points. No Tg was detected for any of the incubation times between 0 and 24 hours of pre-treatment. DSC analysis was repeated 48 hours after water addition and the pre-treated composition still lacked a detectable glass transition temperature. However, once PTC21 was emulsified and aged for 30 minutes at RT, the oil phase thereafter extracted therefrom displayed a Tg at about 0° C., when tested by DSC. The presence of a detectable Tg, even if not representative of a fully cured network, indicated that condensation curing took place in the aged emulsion. As previously explained in the description, the inability of cross-linked polymers to form colored coats is not unexpected.

Example 2: Preparation of Reactive Amino-Silicone Emulsions

After maintaining the pre-treatment oil phase mixtures of dried and neutral water re-humidified reactants prepared in Example 1 for their respective incubation times (i.e., 0 hr, 2 hrs, 4 hrs or 24 hrs, as described above), 0.2 g of each mixture were added to 60 ml of a water solution containing 0.1% Tween® 80 as emulsifier (for PTC1-8 and PTC18 derived mixtures) or 60 ml of plain water (for PTC9-PTC17 and PTC21-PTC22 derived mixtures) contained in a 100 ml plastic container. The obtained combinations of oil and water phases were mixed and emulsified at a constant shear rate (2,000 rpm) for 30 seconds using a planetary centrifugal mixer (Thinky Mixer ARE-250, Thinky Nippon Monozukuri Innovator, Japan).

For convenience, an amino-silicone emulsion prepared according to this example shall be referred to as $ASEn_{tx}$, wherein n stands for the number of the pre-treatment composition being emulsified and tx for the incubation time of the pre-treatment composition (x being provided in hours). For illustration, the amino-silicone emulsions resulting from the emulsification of pre-treatment composition number 1 (PTC1) incubated for 0, 2, 4 or 24 hours shall be termed $ASE1t_0$, $ASE1t_2$, $ASE1t_4$, and $ASE1t_{24}$, accordingly.

The pH of the resulting emulsions (e.g., $ASE1t_0$ to $ASE18t_{24}$ so far described) was measured using a pH meter (pH 211, Hanna Instruments, USA) and generally found to be about pH 10. This pH (circa pH 10) was typical of all emulsions prepared according to the present teachings.

The zeta potential of the resulting emulsions was measured using a Zetasizer Nano Z (by Malvern Instruments) with a folded capillary cell DTS1070. All emulsions displayed at native pH (~10) a positive zeta potential greater than zero, for instance of at least +1 mV. For instance, $ASE3_{t0}$ (prepared from $PTC3_{t0}$) had a zeta potential of +4 mV and ASE21 to (prepared from $PTC21_{t0}$) had a zeta potential of +6 mV. In order to eliminate mild fluctuations due to minor variations in native pH, the emulsions can be slightly acidified (e.g., with glacial acetic acid) to pH 9 to reach a pH value that may be common and comparable to all emulsions. At a pH 9, the zeta potential of $ASE3_{t0}$ was found to be of +24 mV.

The amino-silicone emulsions $ASE1t_0$ to $ASE18t_{24}$ were generally applied to hair fibers within at most 15 minutes of their emulsification. The coating process is detailed in Example 4.

The MTMS emulsion ASE22 to was applied to textile samples immediately after its emulsification. The coating process is detailed in Example 16.

The inventors have established in an application published as WO 2018/187246, the suitability of additional reactive amino-silicone pre-polymers for the preparation of amino-silicone emulsions able to coat hair fibers. These pre-polymers are listed in Table 2 below, together with previously discussed Dynasylan® SIVO 210, GP-145 and KF-857, included for reference. The reported properties were retrieved or estimated from the product data sheets provided by the respective suppliers. In the following table, BP stands for Branched Polymer, LP stands for Linear Polymer, I and II, respectively indicate a primary or secondary amine group. Other abbreviations and acronyms are as defined for Table 1. It is believed that the amount of water in each of these alternative reactants can be controlled as taught in Example 1.

TABLE 2

| Reactive Amino-Silicone Pre-polymer | Supplier | Amine No.* | Amine Position (Polymer type**) | Amine Type | Viscosity (mPa · s) |
|---|---|---|---|---|---|
| ATM 1322 | Gelest | 101 | Pendant (LP) | I, II | 250 |
| Dynasylan® SIVO 210 | Evonik | 370 | N/A | I, II | 4-40 |
| GP-34 | Genesee | 3.3 | Terminal (LP) | I | 3,500 |
| GP-145 | Genesee | 11 | Terminal (LP) | I | 1,900 |
| GP-397 | Genesee | 116 | Terminal (LP) | I, II | 130 |
| GP-657 | Genesee | 54 | Terminal (LP) | I | 120 |
| GP-846 | Genesee | 110 | N/A (BP) | I, II | 30 |
| KF-857 | Shin Etsu | 127 | Pendant (LP) | I | 65 |
| SF 1706 | Momentive | 47 | Pendant (BP) | I, II | 30 |
| TSF 4703 | Momentive | 62 | Pendant (LP) | I, II | 1,000 |
| TSF 4707 | Momentive | 15 | Pendant (LP) | I, II | 7,000 |
| TSF 4708 | Momentive | 38 | Pendant (LP) | I, II | 1,000 |
| Wacker® Finish WR 1100 | Wacker Chemie | 15 | Pendant (LP) | I, II | 4,000 |
| Xiameter® OFX 8630 | Dow Corning | 25 | Pendant (LP) | I | 3,500 |
| Xiameter® OFX 8822 | Dow Corning | 45 | Pendant (LP) | I | 1,500 |

Additional non-reactive amino-silicone oils are expected to be suitable for the preparation of reactive amino-silicone emulsions able to coat hair fibers, for instance, GP-4, GP-6, GP-468, and GP-581. It is believed that the amount of water in each of these alternative reactants can be controlled as taught in Example 1.

The inventors have established in an application published as WO 2018/187246, the suitability of additional non-amino silicone-based materials for the preparation of amino-silicone emulsions able to coat hair fibers. These materials are listed in Table 3 below, where abbreviations and acronyms are as previously defined. It is believed that the amount of water in each of these alternative reactants can be controlled as taught in Example 1.

TABLE 3

| Non-amino Silicone-based materials | Supplier | Viscosity (mPa · s) |
|---|---|---|
| Dynasylan® GLYMO | Evonik | 3.7 |
| Dynasylan® Hydrosil 2926 | Evonik | 6-7 |
| Siltech® E-2154 | Siltech | 20 |
| SIO6629.1 | Gelest | N/A |
| DMS-S12 | Gelest | 16-32 |
| MTMS | Sigma-Aldrich | 0.5 |
| M2 | Gelest | 0.65 |

Example 3: Preparation of a Polymer-Embedded Pigment Composition

Compounding of EAA Copolymers Having Neutralizable Acid Moieties with a Pigment

In a tree roll mixing mill (Mixing mill Model 00, Sailing International Industry Group, China) whose kneading rolls were heated to about 100° C. by internal oil circulation, were loaded, in the following order, 45% of Primacor™ 5990I, 10% of pigment, and 45% of Luwax® EAS-5 (the ethylene acrylic acid (EAA) copolymers having an acrylic acid content of about 20.5% and 21.5%, respectively). For instance, a 300 g composite can be prepared by compounding 30 g of pigment and 135 g of each EAA copolymer. The EAA-pigment composite paste was reloaded through the kneading rolls, sheared and mixed for about 10 minutes (10 cycles of milling in total). At the end of the melt-kneading compounding process, the relatively dry EAA-pigment stripe-like composite was cut with scissors into small flat squares having edges of about 0.5 cm. The composite flat squares were further ground under cryogenic conditions using liquid nitrogen in a coffee-bean grinder (KG40 from De'Longhi Appliances, Italy), until the EAA-embedded pigments formed a powder of granules having an approximate diameter of a few millimeters.

The inventors have further established in an application published as WO 2018/187246, the suitability of this method when the above polymeric materials having neutralizable acid moieties are separately compounded with the pigment, as well as of additional thermoplastic neutralizable acid-polymers. The compounding temperature (of the kneading rolls) is indicated in parenthesis. Suitable alternative EAA copolymers include: Primacor™ 59801, an EAA copolymer having an acrylic acid content of 20.0 wt. % as determined by the supplier, Dow Chemical Company (compounding temperature of about 150° C.); Nucrel® 2806, an EAA copolymer having an acrylic acid content of 18.0 wt. %, as determined by the supplier, DuPont Company (compounding temperature of about 150° C.); Luwax® EAS-5, an EAA copolymer having an acrylic acid content of about 21.5 wt. % as calculated based on the acid number of 160-180 mg KOH/g provided by BASF (compounding temperature of about 180° C.); and A-C® 5180, an EAA copolymer having an acrylic acid content of about 20.0 wt. %, manufactured by Honeywell International Inc. (compounding temperature of about 130° C.).

Additional suitable thermoplastic neutralizable acid-polymers include copolymers in which the neutralizable acid moieties are methacrylic acid units, such as ethylene methacrylic acid (EMAA) copolymers. For instance, Nucrel® 960, an EMAA copolymer having a methacrylic acid content of about 15.0 wt. %, manufactured by DuPont (compounding temperature of about 140° C.) was found suitable.

Other suitable copolymers have neutralizable acid moieties that include both acrylic acid and methacrylic acid units in an acrylamide copolymer. For instance, Dermacryl® 79, an octylacrylamide/acrylate (AAA) copolymer, having an acid value of 133 mg KOH/g polymer, manufactured by AkzoNobel (compounding temperature of 200° C.) was found suitable.

Additionally, mixtures of copolymers can be used as well, for instance, mixtures of a same copolymer (e.g., Primacor™ 5990I and Luwax® EAS-5, as above-exemplified) and mixtures of different copolymers (e.g., Nucrel® 2806 (EAA) and Nucrel® 960 (EMAA), compounded in equal amounts at a temperature of about 130° C.).

Neutralization of Polymer-Embedded Pigments 20 g powder of EAA-embedded pigments were loaded into a 500 ml glass beaker followed by the addition of 180 ml of distilled water (pH 6.5-7.5). The dispersions, containing 10 wt. % of composite per total weight, were mixed at 3,000 rpm for ten minutes using a high shear mixer (L5M-A, from Silverson Machines Inc., USA), while being heated using a heating plate (Fried Electric Ltd., Israel) to 50° C. The temperature was measured using a standard scientific mercury thermometer (Si-Mada, Israel). To the heated dispersions, 5 ml of ammonium hydroxide (25 wt. %) was added in order to neutralize the EAA copolymers blend in which the pigment was embedded. The mixture was further heated to 80° C. (or any other suitable temperature above the softening temperature of the polymeric material) under continuing mixing at same conditions for about twenty minutes. Then 5 ml of ammonium hydroxide (25 wt. %) were further added to the at least partially neutralized dispersions of EAA-embedded pigments in order to pursue the neutralization reaction till water-dispersibilty of the pigmented polymeric particles is obtained. The neutralization of a sufficient amount of acrylic acid groups in the copolymer generally results in dispersions having a pH of about 10. Equations allowing to estimate the amount of neutralizing agent to be added, as a function of the content of acid moieties in the polymeric material and of the desired degree of neutralization, are known to the skilled persons and such amounts can be readily determined by routine experimentation.

A larger-scale of neutralized dispersion was prepared as follows. 250 g of EAA-embedded pigments powder (Pigment Orange 43 embedded in a mixture of Primacor™ 5990i and Luwax® EAS 5) and 2,250 ml of distilled water were loaded into a vacuum mixer (PVM-2, from Charles Ross & Son, USA), and mixed at 1,500 rpm for 24 h, and a temperature of 80-90° C. Any other suitable temperature above the softening temperature of the polymeric material may be used, and the process was performed using sawtooth disperser blades to allow high shear mixing. To the heated dispersions, 62.5 ml of ammonium hydroxide (25 wt. %) were added, and the mixture was then maintained at the heating temperature under continuing mixing at same conditions for about 24 h. Then another portion of 62.5 ml of ammonium hydroxide (25 wt. %) was added to obtain a neutralized dispersion.

It is to be noted that ammonium hydroxide is a volatile neutralizing agent progressively evaporating, in particular once aqueous micellar dispersions of neutralized pigmented polymeric particles are applied as thin coats. Additional suitable volatile neutralizing agents can be fatty amines, such as ethanol amines (MEA, DEA or TEA) or equivalent organic amines (e.g., morpholine). Following the evaporation of the neutralizing agents, the pH of the coat of neutralized polymeric materials gradually decreases and film formation proceeds to entrap the pigment. The water-resistance of the pigmented polymeric coat increases with the elimination of the neutralizing agents and the decrease in pH of the film.

As excess of neutralizing agent is preferably to be avoided, for the sake of a more rapid evaporation leading to an accelerated film formation and the reduction of stickiness. For this purpose, the amount of base in the neutralized dispersion was monitored by conductivity. Specifically, an electrode probe was dipped into the aqueous dispersion and conductivity was measured using a CyberScan CON 200 conductometer by Eutech Instruments, USA. Base was added, or the dispersion was left to evaporate until a conductivity of less than 3 milliSiemens was reached.

Neutralization of other suitable thermoplastic acid-polymers, as described above in a non-limiting manner, can be performed by a similar process. It is believed that the alkaline solution of ammonium hydroxide facilitates the water-dispersibility of EAA, EMAA or AAA copolymers or blends thereof. It is further believed that at this stage, the pigments are entrapped in a polymeric shell forming a micelle. Hence, the size of the pigment controls the size of the micelles and pigments having a narrow particle size distribution yield a micellar dispersion having a similarly narrow size distribution.

During the neutralization process, a sample of 0.1 ml of micellar dispersion was taken and placed between two glass slides in order to visually assess the presence or absence of aggregates. In case of presence of lumps, aggregates, or flocked particles, additional base (e.g., ammonium hydroxide (25 wt. %)) was introduced to the dispersion which was thereafter mixed for longer periods of time.

At the end of the neutralization process, a neutralized polymer-embedded pigment micellar dispersion was obtained. The dispersion was stable (e.g., displayed a similar PSD over time, retained a relatively constant charge, etc.) under basic pH conditions, even following partial evaporation of a volatile neutralizing agent, as long as the pH remains between 7.5 and 10.0. Such stability was observed even in absence of additional dedicated dispersant(s), the copolymers having reached self-dispersibility in water following the neutralization process. In the event, a dedicated dispersant is added to the neutralized dispersion, stability can be extended to a pH of less than 7.5. In such case, the dispersion can remain stable and efficient even in the range of pH 6-7.5. Generally, the dispersed micelles of the polymer embedding the pigment as herein described displayed a size distribution having a median value in the sub-micron range (e.g., $D_V50 \leq 1$ µm), typically having $D_V50$ values, as assessed by DLS, of less than 750 nm, less than 500 nm, or less than 250 nm. The dispersed particles of neutralized Primacor™ 5990I: Luwax® EAS-5 embedding Pigment Violet 23 displayed a $D_V50$ of about 374 nm and a $D_V90$ of about 647 nm. In absence of pigments, the micelles of neutralized polymeric material have a $D_V50$ of less than 100 nm, less than 50 nm and less than 30 nm.

The zeta potential of the dispersion of Pigment Violet 23 embedded in particles of neutralized Primacor™ 5990I: Luwax® EAS-5 was measured at a pH of 10.0 (native pH) in a sample diluted to contain only 0.5 wt. % of material. The zeta potential was found to be negative (−55 mV). Details shall be provided in Example 9.

The presence of the pigment particles within the dispersed beads of neutralized polymers was confirmed by optical microscopy at a magnification of ×100. The solid content of EAA-embedded pigments in the various dispersions was typically in the range of 9.0 wt. % to 20.0 wt. %. When desired, distilled water was added to compensate for evaporation or reach a particular solid content (e.g., 10.0 wt. %). The pH of the dispersions was generally in the range of about 7.5 to 11.0, 9.0 to 11.0 or of about 9.5 to 10.5. The pH of the dispersion of Pigment Violet 23 embedded in particles of neutralized Primacor™ 5990I: Luwax® EAS-5 was found to be of about 10.0.

It is believed that polymeric materials having a lower acid number should be loaded with a lower amount of pigment, as compared to neutralizable polymers having a higher acid number. In any event, the inventors believe that the extent of the pigment loading should not reach or approach the maximal ability of the polymer having acid groups to be compounded therewith, as a portion of such groups should remain available to ensure the aqueous dispersibility of the polymer-embedded pigment following neutralization. It is assumed that part of the acid moieties serves as pigment affinic groups and are engaged with the pigments being embedded in the polymeric material.

The inventors similarly prepared (and tested for coloring), as reported in an application published as WO 2018/187246, a dispersion with a polymeric material lacking acid moieties, this control polymer being a known water-dispersible pigment-affinic polymer. While the control polymer (a modified polyester commercialized as Eastman AQ™ polymers by Eastman Chemical Company) was successfully compounded with pigments and water dispersed therewith in particulate form, the resulting aqueous dispersion failed to form an outer coat able to attach to an underlying condensation-cured amino-silicone film according to a procedure similar to the one described in Example 4. These findings support the hypothesis that the acid moieties of the polymeric material serve not only to ensure water-dispersibility and/or pigment affinity, but also enable attachment to an adjacent amino-silicone layer, likely by binding with accessible amino side chains of the silicone polymer.

Example 4: Coloration of Fibers

1—Pre-treatment compositions, containing condensation-curable amino-silicone pre-polymers and additional reactive and non-reactive reactants (such as detailed in Example 1), were provided as amino-silicone emulsions prepared following the various incubation times (e.g., 0 hr, 0.5 hr, 1 hr, 2 hrs, 4 hrs and 24 hrs) according to Example 2.

2—A hair tuft (white yak body hair, approximately 7 cm long free hair from Kerling International Haarfabrik GmbH, Germany) was dipped with gentle stirring for about 60 seconds in the $ASEn_{tx}$ reactive amino-silicone emulsion sample.

3—The hair tuft coated with the reactive amino-silicone emulsion was then thoroughly rinsed with tap water at about 25° C. to remove any excess of the emulsion.

4—The rinsed hair tuft coated with the reactive amino-silicone emulsion was then dipped with gentle stirring for about 60 seconds in the aqueous dispersion of neutralized polymer-embedded pigment, prepared as described in Example 3. The composite pigment-copolymer constituted 10% by weight of the final dispersion and its conductivity was of less than 3 milliSiemens.

5—The hair tuft coated with a dispersion of polymer-embedded pigment was then rinsed with tap water at about 25° C. for a few seconds to remove excess of coloring dispersion.

6—The rinsed colored hair tuft was washed with a cationic shampoo (Expert Selection, Keratin Smooth, TRESemmé, Unilever, USA), the fibers being gently massaged with the shampoo to ensure proper coverage, and then thoroughly rinsed with tap water at about 25° C.

7—The washed colored hair tuft was dried for approximately 30 seconds with a Philips compact hair dryer operated to blow hot air at a distance of about 20 cm from the hair fibers, enabling a temperature of about 50° C. on hair surface.

It should be noted that cationic shampoos are preferred at this stage, as the films are typically still undergoing curing and furthering their formation (cohesivity) and attachment (adhesivity) to the underlying substrates.

It should further be noted that while the temperature of the air flow can accelerate the evaporation of the volatile components (e.g., of the water carrier or of the neutralizing agent), it is not pivotal to the coating process according to the present teachings and hair samples dried with air blown at ambient temperature (circa 23° C.) provided similar results.

The hair sample was generally combed during the drying process to facilitate exposure of all fibers to the air flow, so as to shorten the drying step. However, combing is not essential to the invention, as the coating of hair fibers according to the present teachings is a self-terminating process. As explained with reference to FIGS. 1 and 2, a self-terminating process advantageously prevents or reduce the formation of liquid bridges between adjacent fibers. Liquid bridges may, in processes where self-termination of coating is absent, result in hair stuck in lump of coloring composition. In such detrimental cases, the clustered hair would require individualization by combing, this process adding a mechanical stress to the hair, further reducing likelihood of satisfactory coating. Dried colored hair samples were kept at RT until further study.

Example 5: Feel of Colored Fibers

The feel of the dried hair fibers colored according to Example 4 was qualitatively assessed by trained persons. All samples provided for a non-sticky sensation to the touch, the hair fibers being individually available and not forming any lump. However, the touch was generally more and more pleasant, as the incubation time of the pre-treatment compositions, before emulsification, was prolonged. Within the time period of up to 24 hours assessed in Example 1, it was generally observed that the non-tacky touch provided by $ASEn_{t24}$ was equal to or greater than the feel provided by $ASEn_{t4}$, which is in turn was equal to or greater than the feel provided by $ASEn_{t2}$, itself more pleasant than the feel provided by $ASEn_{t0}$. Put in mathematical terms, the results suggest that $ASEn_{t24} \geq ASEn_{t4} \geq ASEn_{t2} \geq ASEn_{t0}$, with respect to feel of the colored hair.

Among each series of pre-treatment compositions, having same reactants, one of them including an increasing amount of added water, it was generally observed that increasing the amount of water added to the dried reactants accelerated the process (as visually more perceptible when following pace of coloration). Thus, taking for example the first time point of t0 and PTC1-5 in which water was pre-mixed with KF-857, the non-tacky feel of ASE5 is at least as pleasant as ASE4, which in turn is at least as pleasant as ASE3, and so on. Put in mathematical terms, the results suggest that, with respect to feel of the colored hair, $ASE5 \geq ASE4 \geq ASE3 \geq ASE2 \geq ASE1$ (pre-mixes of reactive KF-857); $ASE8 \geq ASE7 \geq ASE6$ (pre-mixes of reactive GP-145); $ASE13 \geq ASE12 \geq ASE11 \geq ASE10 \geq ASE9$ (pre-mixes of non-reactive GP-967); and $ASE17 \geq ASE16 \geq ASE15 \geq ASE14$ (pre-mixes of non-reactive GP-965).

While all series of pre-mixes yielded following coloration non-sticky hair fibers, it was observed that hair colored with ASE9 to ASE17 and ASE21 provided a mildly more rigid, yet satisfactory, feel (providing for an improved abrasion resistance, as assessed by lack of transfer to a rough paper substrate following aggressive rubbing). In contrast ASE1 to ASE8 and ASE18 provided a comparatively more natural/flexible feel to the touch. However, this more pleasant feel was at the expense of a relatively reduced abrasion resistance.

The results obtained with ASE1 to ASE8, as compared to ASE18, demonstrate that more than one reactant can be humidified during the pre-treatment of the oil phase. At t0, the ASEs prepared by including in their oil phase two humidified reactants (KF-857 or GP-145, in addition to the hydrophobic fumed silica) provided a mildly more vivid coloration than ASE18, where the hydrophobic fumed silica was the sole reactant supplemented with water.

Example 6: Wash Resistance of Colored Fibers

The purpose of this example was to rapidly subject hair samples colored according to Example 4 to intensive washing, as a predictive model for the permanency of coloration. This procedure was generally performed 24 hours after drying of the colored hair samples (unless otherwise specifically indicated in particular experiments).

A standard shampoo (Shea natural keratin shampoo by Saryna Key, Israel), was applied on the dried colored hair samples and thoroughly massaged between the fingers of the operating person to ensure full coverage and intimate contact. At this stage, the films, including the colored one, are believed to be firmly attached to the hair, as demonstrated in the following. Hence, the use of a cationic shampoo is no longer recommended, and a regular shampoo was preferred to mimic more aggressive chemical conditions. Excess shampoo was squeezed away, and this step was repeated four more times. After a total of five such shampooing cycles, the hair was rinsed with tap water at about 25° C.

Previous step was repeated four more times, the total number of shampooing cycles amounting to 25 at the end of the procedure. Following the last shampooing cycle, the hair samples were thoroughly rinsed with tap water at about 25° C., followed by drying and combing as described in Example 4.

Example 7: Optical Density Measurements

The optical density (OD) of dried hair samples was measured using an X-Rite 939, D65/10 spectrophotometer (X-Rite Inc., USA). Measurements were performed on at least three segments of a coated (colored) or uncoated (reference) hair sample and averaged. Mean values are reported in the following.

A baseline $OD_{base}$ was measured after completion of the coloration. For hair samples subjected to the shampooing resistance test, an $OD_{wash}$ was also measured following completion of the test. A reduction in OD of less than 20% from baseline ($OD_{wash}/OD_{base} \geq 0.8 \times OD_{base}$) was considered satisfactory and indicative of a significant attachment of the colored films to the hair fibers. Colorations fulfilling this condition (including pigment-less underlying coats supporting such effect) are termed herein "permanent".

As used herein in the specification and in the claims section that follows, the terms "permanence" and "wash resistance", with respect to coated, pigmented mammalian hair fibers, are used interchangeably to refer to such coated fibers (e.g., coated hair fibers), coated with a pigment-containing coating in accordance with a coating protocol (e.g., as described in Example 4), and having (i) a measured baseline Optical Density (OD) value ("$OD_{baseline}$" or "$OD_{base}$") determined after full curing has ensued following the administration of the coating according to the coating protocol; and (ii) a measured OD value ("$OD_{post-wash-protocol}$" or "$OD_{wash}$") obtained after administration of the coating according to the coating protocol and subsequently washing the cured coated fibers at least 25 times with a shampoo, according to a wash protocol (e.g., as described in Example 6 for a standard, sulfate-containing shampoo), and wherein $OD_{post-wash-protocol}$ is at least 80% of $OD_{baseline}$.

All samples colored as described in Example 4, using for the formation of a first coat of amino-silicone any of the emulsions prepared as described in Examples 1 and 2 (e.g., $ASE1t_0$ to $ASE18_{t24}$), provided for an OD of at least about 1.3. For comparison, uncoated white Yak hair displayed an OD of about 0.36.

Within the time period of up to 24 hours assessed in Example 1, it was generally observed that coloration (OD) was stronger when the pre-treatment compositions were incubated at least two hours prior to emulsification, as compared to immediate emulsification. For some samples, strong coloration was still observed for ASEs pre-treated up to 24 hours, for others the coloration at the end time point of the tested duration pre-treatment displayed a decrease in coloration. Put in mathematical terms, the results suggested two main behavior, in a first one coloration is still in plateau after 24 hours of treatment, $ASEn_{t24} \geq ASEn_{t4} \geq ASEn_{t2} > ASEn_{t0}$, in a second one, coloration is decreasing following a plateau of more than 4 hours and less than 24 hours. It is believed that a strong coloration can be obtained in less than 2 hours of pre-treatment, however the time period spanning from 0 to 2 hours has yet to be investigated for intermediate values.

Among each series of pre-treatment compositions, having same reactants, one of them including an increasing amount of added water, it was generally observed that increasing the amount of water added to the dried reactants improved the intensity of coloration, when such issue was considered at the earlier stage of a coloration plateau (maximum OD). Thus, taking for example the first time point in plateau, namely 2 hours of pretreatment in the particular situation of Example 1, the OD of $ASE5_{t2}$ was at least equal to or greater than the OD of $ASE4_{t2}$, which in turn was at least to or greater than the OD of $ASE3_{t2}$, and so on. Put in mathematical terms, the results suggest that the optical densities of samples colored by the following amino-silicone emulsions can be ranked: $ASE5_{t2} \geq ASE4_{t2} > ASE3_{t2} \geq ASE2_{t2} \geq ASE1_{t2}$ (pre-mixes of reactive KF-857); $ASE8_{t2} \geq ASE7_{t2} \geq ASE6_{t2}$ (pre-mixes of reactive GP-145); $ASE13_{t2} \geq ASE12_{t2} \geq ASE11_{t2} \geq ASE10_{t2} \geq ASE9_{t2}$ (pre-mixes of non-reactive GP-967); and $ASE17_{t2} \geq ASE16_{t2} \geq ASE15_{t2} \geq ASE14_{t2}$ (pre-mixes of non-reactive GP-965).

Regarding resistance to shampooing, it was generally observed that a pre-treatment of at least 2 hours significantly improved permanency, as compared to emulsions immediately prepared at time zero. There seems to be a plateau in performance, following which a slight decrease in optical density as compared to respective baseline was observed. It was further observed, with samples colored with oil phases sporadically pre-treated for more than 24 hours, that wash resistance was impaired, the OD having decreased by more than 20% from baseline values after more than 24 hours pretreatment of the oil phase.

As for coloration per se, wash resistance improved with increasing amount of water for each series of pre-treatment compositions, having otherwise same reactants. Thus, taking for example the first time point measured in the plateau phase, namely 2 hours of pretreatment in view of the time points tested in Example 1, the wash-resistance of $ASE5_{t2}$ was at least equal to or greater than the wash-resistance of $ASE4_{t2}$, which in turn was at least equal to or greater than the wash-resistance of $ASE3_{t2}$, and so on. A first hair sample is having a better wash-resistance than a second hair sample when the ratio of $OD_{wash}/OD_{base}$ of the first hair sample is greater than said ratio for the second hair sample.

Put in mathematical terms, the results suggest that the $OD_{wash}/OD_{base}$ ratio of samples colored by the following amino-silicone emulsions can be ranked: $ASE5_{t2} \geq ASE4_{t2} \geq ASE3_{t2} \geq ASE2_{t2} \geq ASE1_{t2}$ (pre-mixes of reactive KF-857); $ASE8_{t2} \geq ASE7_{t2} \geq ASE6_{t2}$ (pre-mixes of reactive GP-145); $ASE13_{t2}?ASE12_{t2} \geq ASE11_{t2} \geq ASE10_{t2} \geq ASE9_{t2}$ (pre-mixes of non-reactive GP-967); and $ASE17_{t2} \geq ASE16_{t2} \geq ASE15_{t2} \geq ASE14_{t2}$ (pre-mixes of non-reactive GP-965).

It is to be noted that Dynasylan® SIVO 210 (having an estimated average Amine Number of 370) contains, according to its suppliers, a blend of three monomers: 3-aminopropyl-triethoxysilane (CAS No. 919-30-2, generally present at 25% or more) having an Amine Number of 450, bis(triethoxy-silylpropyl) amine (CAS No. 13497-18-2, generally present at more than 20%) having an Amine Number of 235 and 1-(3-(triethoxysilyl)propyl)-2,2-diethoxi-1-aza-2-silacyclopentane (CAS No. 1184179-50-7, generally present in the range of 1-5%) having an Amine Number of 263. These materials are individually available respectively as Dynasylan® AMEO from Evonik, SIB1824.5 and SIT8187.2 from Gelest and their respective effect can be separately assessed by replacing Dynasylan® SIVO 210 by any one of its constituents (in same amount).

This experiment was performed, and water-insoluble monomers were found preferable over water-soluble ones. Water-solubility was assessed by mixing 1 wt. % of the material in near neutral (~pH7) distilled water at RT, followed by a brief vortex for homogeneity. A clear solution indicated a water-soluble material, whereas turbidity indicated an at least partly water-insoluble material. By this method, Dynasylan® AMEO was confirmed to be water soluble, while SIB1824.5 and SIT8187.2 (as well as parent Dynasylan® SIVO 210) were found to be insoluble.

For reference, other liquid reactants used in the preparation of the above-described pre-treatment compositions were similarly tested for water solubility. All were found water-insoluble at 1 wt. % (or more) at about pH7 and 23° C. Namely, the reactive condensation-curable amino-silicone pre-polymers (KF-857, GP-145) and the amino-silicone oils (GP-965, GP-967) yielded a turbid dispersion in water. These results support the presence of all reactants in a same phase, which in the present disclosure is the reactive oil phase. For comparison, low MW reactive silanes 3-aminopropyldimethylethoxysilane (MW 161) and N-(2-aminoethyl)-3-aminopropyltriethoxysilane (MW 264) were found water soluble, forming clear solutions at 1 wt. %, by same method.

The individual components of Dynasylan® SIVO 210 were dried with molecular sieves, as previously described in Example 1. The dried constituents were then tested for suitability for preparation of amino-silicone emulsions, as the parent mixture, when combined with amino-silicone pre-polymers (e.g., KF-857, GP-145) and/or with amino-silicone oils (e.g., GP-965, GP-967). Two pre-treatment compositions were modified to assess this matter, PTC3 and PTC9 pre-treated for two hours. In the "PTC3 modified" compositions the reactant being replaced was present at about 78 wt. % of the reactive oil phase, while in the "PTC9 modified" compositions the reactant being replaced was present at about 73 wt. % of the reactive oil phase. When Dynasylan® SIVO 210 was replaced by its insoluble constituents, SIB1824.5 and SIT8187.2, both provided satisfactory color intensity with ODs of at least 1.25, as compared to an OD of about 1.39 for the parent mixture and as opposed to the water-soluble component with an OD near uncoated hair baseline values. An emulsion prepared by replacing Dynasylan® SIVO 210 by its water-soluble constituent, Dynasylan® AMEO, yielded a faint coloration believed to merely result from the deposition of the water-insoluble reactants on the hair fibers. In a control experiment, wherein Dynasylan® SIVO 210 or its individual components were the sole constituents of the reactive oil phase, emulsified at 0.2 g per 60 ml water, the coloration was too faint to further assess permanency and the expected advantage of non-soluble materials as compared to water-soluble ones.

With regard to permanency of coloration, assessed after 24 hours, when Dynasylan® SIVO 210 was replaced by its insoluble constituents, SIB1824.5 and SIT8187.2, and none of them were pre-mixed with water ahead of emulsification, SIT8187.2 was found comparable to parent mix and superior to SIB1824.5, providing for a shampoo-resistant coloration ($OD_{wash}/OD_{base}$ of about 91%) with first coats prepared from both pre-treatment compositions.

When the replacing reactants were each pre-mixed to include 2 wt. % of neutral water for a further modification of the pre-treatment compositions, which were then incubated for 2 hours prior to emulsification, a positive effect was observed.

Taking a composition, wherein Dynasylan® SIVO 210 was replaced by SIT8187.2, and this insoluble constituent was further humidified with 2. wt. % neutral water. The pre-treatment composition (incubated for 2 hours) provided for a satisfactory coloration of about 1.51. With regard to permanency, it was assessed by performing the shampoo-resistance test immediately following coloration, or 2, 4, 6 and 24 hrs thereafter. No permanency was observed at time 0, but wash resistance increased with time, resulting in $OD_{wash}/OD_{base}$ ratios of about 90% in the range of 4 to 24 hours following coloration. Furthermore, when SIT8187.2 was pre-treated with 1 wt. % of neutral water, instead of 2 wt. %, permanency of coloration obtained with the 2 hours pre-treated composition was immediately achieved. In other words, the coloration was shampoo-resistant shortly after its application. These results further show that addition of water to a reactant of the reactive oil phase can shorten the time till onset of permanency of coloration.

Finally, all compounds were supplemented with 2. wt. % neutral water, prepared as modified PTC9 compositions which were incubated for 24 hrs of pre-treatment. The pre-treated oil phases were then emulsified and used to color hair samples as previously detailed. The colored hair samples were allowed to age for another 24 hrs, at which time wash-resistance was assessed.

The results of these experiments are summarized in the following table wherein the pre-treatment compositions are identified by the sole amino-functional material being replaced. In the table, SR stands for shampoo-resistance where permanency is reported. When permanency of coloration was obtained, the optical density of the samples washed with 25 shampooing cycles is also reported.

TABLE 4

|  | Dry Reactant | | | | Humidified Reactant | |
| --- | --- | --- | --- | --- | --- | --- |
|  | "PTC3" | | "PTC9" | | "PTC9" | |
| Replaced Reactant | OD | SR | OD | SR | OD | SR |
| Dynasylan ® SIVO 210 | 1.38 | Yes 1.31 | 1.40 | Yes 1.31 | 1.40 | Yes 1.25 |
| SIB1824.5 | 1.58 | No | 1.26 | No | 1.55 | Yes 1.34 |
| SIT8187.2 | 1.25 | Yes 1.13 | 1.25 | Yes 1.13 | 1.52 | Yes 1.38 |
| Silquest ® VX-225 | 1.51 | No | 1.57 | No | 1.52 | Yes 1.30 |
| Silquest ® Y-15744 | 1.31 | No | 1.41 | No | 1.48 | No |

As can be seen from Table 4, both insoluble constituents of Dynasylan® SIVO 210 and the parent mix provided for a comparable permanency in the present study. Interestingly, this suggests that when the water-soluble constituent of Dynasylan® SIVO 210 is mixed with the insoluble constituents thereof, its presence does not significantly affect their respective performance.

In an additional series of similar experiments, the aforementioned condensation-curable amino-silicone monomers were replaced by oligomers. The condensation-curable amino-silicone oligomers, Silquest® VX-225 and Silquest® Y-15744 were supplied by Momentive Performance Materials and tested in dried or humidified form as above explained. Results are reported in Table 4.

From the standpoint of coloration, the condensation-curable amino-silicone oligomers provided for a high OD, whether emulsified from pre-treatment compositions modified from PTC3 or PTC9. Emulsions prepared from dry oligomers did not enable permanency of such colorations. However, when the oligomers were first supplemented with 2 wt. % neutral water as assessed using a modified PTC3, then Silquest® VX-225 (having an Amine Number of about 277) provided for the formation of a wash-resistant coloration.

Example 8: Short Pre-Treatment of Oil Phase

As mentioned in previous examples, the pre-treatment time points used in Example 1 were relatively distant from one another and it is believed that some of the phenomena first observed with emulsions treated at least 2 hours might in fact have occurred at an earlier time point between 0 and 2 hours. The purpose of this example was to check this possibility by using shorter intervals, the incubation time being of 0, 15, 30, 45, 60, 90 and 120 minutes.

The shorter incubations were performed on compositions corresponding to PTC3 (KF-857), PTC15 (GP-965) and PTC18 (fumed silica), the humidified reactant being indicated in parenthesis. Each illustrate a different type of reactant, KF-857 representing a condensation-curable amino-silicone pre-polymer, GP-965 representing a non-reactive amino-silicone and the fumed silica representing a solid reinforcement filler.

The results showed that maximal coloration can be reached with shorter pre-treatment time periods, fifteen minutes or less, being sufficient to reach the beginning of a plateau. With regards to feel, as previously demonstrated all provided for a pleasant feel at time 0 which only mildly improved with time as qualitatively assessed by trained operating persons. In the present example, ASE15 and ASE18 provided their respective superior feel with oil phases pre-treated for 15 minutes or less. ASE3 provided its superior feel with an oil phase pre-treated more than 15 minutes and 30 minutes or less. With regard to permanency, no improvements were measured in the time window of 0 to 2 hours.

Example 9: Coloring Fibers with Various Pigments

Example 4 was repeated, by using for the first coat amino-silicone emulsion $ASE3_{t4}$ (emulsified from PTC3 incubated for 4 hours), the preparation of which is detailed in Examples 1 and 2. For the second coat, the polymer-embedded pigment compositions (prepared according to Example 3) contained instead of 10 wt. % Chromophtal® Violet K5800, 10 wt. % of the coloring agents listed in Table 5. Color index (CI) numbers of the pigments or control dyes are indicated in parenthesis. All aqueous dispersions contained 10 wt. % of composite, hence 1 wt. % of pigment by weight of the applied dispersion. All dispersions had a conductivity of less than 3 milliSiemens at time of application to the hair fibers. For convenience, the PSD of the dispersed colored micelles (as measured in nanometers by DLS, in term of volume) and the zeta potential of the dispersions (as measured at pH 10 and solid content of 0.5 wt. %, in term of mV) are also reported.

In Table 5, N/T stands for Not Tested, and in the column of the suppliers, Cabot stands for Cabot Corporation, USA, Cappelle stands for Cappelle Pigments, Belgium, Clariant stands for Clariant International, Switzerland, Geotech stands for Geotech International, The Netherlands, Lowenstein stands for Jos. H. Lowenstein & Sons, USA, Neelikon stands for Neelikon Dyestuffs, India, and Sensient stands for Sensient Colors, USA.

TABLE 5

| Pigment (Color Index) | Supplier | Dv10 | Dv50 | Dv90 | Zeta Potential |
|---|---|---|---|---|---|
| Acid Green 25 (CI 61570) – [1] | Sensient | 18 | 26 | 41 | N/T |
| Acid Green 25 (CI 61570) – [2] | Sensient | 270 | 861 | 2290 | –45 mV |
| Carbon Black MBD 241 (CI 77266) | Geotech | 130 | 464 | 1410 | –25 mV |
| Carbon Black Monarch ® 580 (CI 77266) | Cabot | 157 | 269 | 429 | –27 mV |
| Chromophtal ® Violet K 5800 (CI 51319) | BASF | 188 | 374 | 647 | –55 mV |
| Diacetanil Yellow HTT 8318C (CI 21108) | Cappelle | 62 | 90 | 142 | –50 mV |
| Disperse Violet 1 (CI 61100) | Lowenstein | 22 | 34 | 457 | –31 mV |
| Heliogen® Green K 8730 (CI 74260) | BASF | 145 | 369 | 704 | –54 mV |
| Hostaperm Green GNX-C (CI 74260) | Clariant | 143 | 280 | 501 | –37 mV |
| Hostaperm Orange 43 (CI 71105) – [1] | Clariant | 153 | 506 | 965 | –45 mV |
| Hostaperm Orange 43 (CI 71105) – [2] | Clariant | 133 | 699 | 1250 | N/T |
| Pigment Blue 60 (CI 69800) | BASF | 212 | 669 | 1250 | –48 mV |
| Pigment Red 57:1 (CI 15850:1) | Sensient | 225 | 301 | 396 | –15 mV |
| Pigment Yellow 1 (CI 11680) | Neelikon | 121 | 182 | 608 | –63 mV |
| Unipure Red LC 3079 (CI 15850) | Sensient | 14 | 22 | 1360 | –25 mV |
| Vynamon Red 312201 (CI 73915) | Heubach | 104 | 201 | 377 | –50 mV |

All dispersions prepared from the above-listed coloring agents, once compounded in EAA copolymers and neutralized as previously described, provided satisfactory coloration. The coloration was assessed following their application on hair fibers already coated with a first film of reactive amino-silicone pre-polymers. All hair samples colored with these additional examples of colored dispersions displayed a pleasant non-tacky feel to the touch. Wash-resistance was not tested, as the different pigments are not expected to modify the behavior observed with $ASE3_{t4}$.

Interestingly, some of the above-listed coloring agents are considered as relatively soluble dyes, as opposed to pigments naturally relatively water-insoluble. The dyes include, for example, Unipure Red LC 3079, and hair colored therewith was shown to be less wash-resistant than hair colored with pigments.

The inventors have established in an application published as WO 2018/187246, the suitability of mixing pigmented aqueous dispersions of polymeric material, such as afore-said, so as to obtain new shades resulting from the combination of the shades of the individual dispersions being combined during the coloration procedure.

Regarding the zeta potential values of the neutralized dispersions of pigments embedded in the copolymers having acid-moieties, in some embodiments, the zeta potential can be measured at a pH of at least 8.0 and at most 12.0, said measurement being optionally performed at a native pH (e.g., circa 10.0). Conveniently, the measurement of the zeta potential of a material or of a composition can be performed at low concentration of the material in an appropriate carrier or on a diluted form of the composition. For instance, a test sample may comprise 2 wt. % or less of solid material or composition ingredients, 1 wt. % or less, or 0.1 wt. % or less.

In the present example, the surface zeta potential values of the afore-described dispersions were measured on diluted samples comprising 0.5 wt. % of solid materials and having a pH of 10. Measurements were made using a Zetasizer Nano Z (by Malvern Instruments) with a folded capillary cell DTS1070. As can be seen from Table 5, all dispersions, independently of the pigment being embedded, were negatively charged. According to some embodiments, the dispersion of polymeric material having neutralized acid moieties and embedding the pigment is charged and has a negative surface zeta potential whose negativity is –5 mV or less, –10 mV or less, –20 mV or less, –40 mV or less, –60 mV or less; and whose negativity is at most –100 mV, at most –80 mV, or at most –70 mV. In some embodiments, the dispersion has a negative surface zeta potential within the range of –100 mV to –10 mV, –80 mV to –10 mV, –70 mV to –10 mV, –70 mV to –20 mV, or –70 mV to –40 mV.

Example 10: Skin Staining

Traditional hair coloration is generally considered messy, the colorants often staining in a non-selective manner the areas surrounding their preparation or application. They may, for instance, undesirably stain skin (including facial and scalp skin), vessels and any other such surfaces, sometimes in a non-reversible manner. The purpose of the present example is to show that coloration using the methods and compositions disclosed herein can be selective to hair fibers.

Coloring compositions according to the present teachings were applied to ventral and dorsal segments of pig skin. Two series of experiments were performed. In a first series, the surfaces were sequentially coated with a condensation-curable amino-silicone emulsion (namely ASE3) and with a colored dispersion of neutralized acid-polymers, the coating process being essentially as described for hair fibers. In a second series of experiments, the colored dispersions were directly applied on the target surfaces. Following the last application, excess compositions were removed, and the surfaces were rinsed with tap water.

All skin surfaces were stained by the present compositions, however, and in contrast with traditional coloring methods, this staining was easily reversed by simple wash with water. It was generally observed that coloring achieved with dispersions comprising larger particles of coloring agent was easier to remove than coloring obtained by dispersions comprising smaller particles.

Referring to Table 5 where the coloring dispersions are described in more details, a dispersion of Heliogen® Green K 8730 (having a $D_V50$ of 369 nm) directly applied or via an amino-silicone first coat to pig skin was washed more easily than a dispersion of Acid Green 25 (having a $D_V50$ of 26 nm). Dispersions comprising Carbon Black Monarch® 580 (having a $D_V50$ of 269 nm), Vynamon Red 312201 (having a $D_V50$ of 201 nm), Pigment Blue 60 (having a $D_V50$ of 669 nm), or Hostaperm Orange 43 (having a $D_V50$ of 699 nm), were similarly found non-staining when applied on pig skin. Skin staining produced by these relatively larger pigments was easier to wash away than the transient staining generated with dispersions of Acid Green 25 (having a $D_V50$ of 26 nm), Unipure Red LC 3079 (having a $D_V50$ of 22 nm), Diacetanil Yellow HTT 8318C (having a $D_V50$ of 90 nm), or Disperse Violet 1 (having a $D_V50$ of 34 nm).

These results support the selectivity of the present coloring compositions towards hair fibers and the relative ease to remove them from undesired areas.

Example 11: Reactive Amino-Silicone Emulsions Prepared from Anhydrous Reactants

The effect, on the coloration of hair fibers and permanency, of controlled water amounts in reactants serving for the preparation of the oil phase of emulsions of reactive amino-silicone pre-polymers was illustrated in Examples 7 and 8. In the present example, comparative emulsions were prepared for which all reactants were used in their anhydrous state. All reactants were dried either in oven or using molecular sieves, as described in Example 1, to reduce presence of water to minimal water content. No water was added to any of the reactants, during the preparation of the oil phase of the emulsion.

Anhydrous Comparative Pre-Treatment Composition 1 (AnPTC1)
Into a 20 ml sealable glass vial, the following were placed:
0.23 g (2.23 wt. % by weight of the final mixture) of dried Aerosil® R 8200;
0.27 g (2.62 wt. % by weight of the final mixture) of dried GP-145;
1.80 g (17.4 wt. % by weight of the final mixture) of dried KF-857; and
8.0 g (77.67 wt. % by weight of the final mixture) of dried Dynasylan® SIVO 210.

AnPTC1 can be compared to PTC18, differing only in the amount of water in the hydrophobic fumed silica (0.4 wt. % in the anhydrous version and 0.8 wt. % in the humidified one).

Anhydrous Comparative Pre-Treatment Composition 2 (AnPTC2)
Into a 20 ml sealable glass vial, the following were placed:
2.00 g (20 wt. % by weight of the final mixture) of dried GP-967;
0.67 g (6.66 wt. % by weight of the final mixture) of dried GP-965; and
7.33 g (73.33 wt. % of the final mixture) of dried Dynasylan® SIVO 210.

AnPTC2 can be compared to PTC9-13, differing only in the amount of water added to GP-967, or to PTC14-17, differing only in the amount of water added to GP-965.

Emulsions were immediately prepared according to Example 2, the incubation time of the oil pre-mix being equivalent to t0. Coloration was conducted as described in Example 4.

Coloration was obtained using both anhydrous comparative emulsions, the OD being satisfactorily above 1.0 (about three-times uncoated hair reference OD). However, the OD was mildly lower and the coloration less vivid than samples comprising relevant reactants supplemented with controlled amounts of water, whether incubated for 0, 2 or 4 hours (all typically above 1.2).

The most stringent effect of use of anhydrous reactants related to the feel and to the permanency of coloration. Emulsions immediately prepared from anhydrous reactants provided for an initial sticky feeling and a lack of wash resistance, as assessed by 25 shampooing cycle as described in Example 6. The ratio of $OD_{wash}/OD_{base}$ was of about 50% for hair colored with an emulsion immediately prepared using AnPTC1 and of about 44% for hair colored with an emulsion immediately prepared using AnPTC2. In the context of lack of permanency, it can be noted that the presence of water during application to the hair (i.e., from the water phase of the emulsion) was not sufficient to counterbalance the anhydrous status of the reactants, despite the excess of applied water over the minor amounts that could have been added to the reactants.

It should be noted that these results do not mean that anhydrous reactants should be proscribed, as these undesired phenomena are expected to disappear with extension of the pre-treatment duration and/or of the curing duration on the hair fibers. It is believed that provided sufficient time, an oil phase consisting of dried reactants or an amino-silicone film formed therefrom can equilibrate with ambient moisture and acquire the minor water amounts triggering or improving the rate of hydrolysis of the condensation-curable amino-silicone pre-polymers.

Example 12: Preparation of Reactants with pH Modified Water

The effect of controlled water addition to reactants serving for the preparation of oil phase of emulsions of reactive amino-silicone pre-polymers was illustrated in Examples 7 and 8, the results of Example 11 further setting a reference for anhydrous reactants. In the present example, comparative emulsions were prepared for which some of the reactants were humidified (water-enriched) with pH modified water. All reactants were dried either in oven or using molecular sieves, as described in Example 1. But, instead of adding distilled water having a near neutral pH of 6.5-7.5, water having an acid pH of 1 was added in known amounts. The acidified aqueous solution was prepared by mixing equal volume of distilled water and 99.85% pure glacial acetic acid (Sigma-Aldrich, CAS No. 64-19-7). For simplicity, the resulting solution shall be referred to as "acid water".

Pre-mixes comprising (a) reactive KF-857 and 0.5 wt. % of added acid water or (b) reactive Dynasylan® SIVO 210 and 2.0 wt. % of added acid water were prepared substantially as described in Example 1. Hydrophobic fumed silica was humidified as described therein with neutral water (0.8 wt. % final).

Pre-Treatment Composition 19 (PTC19)
Into a 20 ml sealable glass vial, the following were placed:
0.23 g (2.23 wt. % by weight of the final mixture) of hydrophobic fumed silica (Aerosil® R 8200) humidified with 0.8 wt. % neutral water;
0.27 g (2.62 wt. % by weight of the final mixture) of dried GP-145;
1.80 g (17.4 wt. % by weight of the final mixture) of the KF-857 reactive amino-silicone pre-mix containing 0.5 wt. % of acid water; and
8.00 g (77.67 wt. % by weight of the final mixture) of dried Dynasylan® SIVO 210.

Pre-Treatment Compositions 20 (PTC20)
Into a 20 ml sealable glass vial, the following were placed:
2.00 g (20 wt. % by weight of the final mixture) of dried GP-967;
0.67 g (6.66 wt. % by weight of the final mixture) of dried GP-965; and
7.33 g (73.33 wt. % of the final mixture) of the reactive Dynasylan® SIVO 210 pre-mix containing 2 wt. % of acid water.

The afore-said pre-treatment mixtures formed a clear uniform oil phase (not turbid and without separation of the minute amounts of water to a distinct aqueous phase). The oil phase samples of PTC19 and PTC20 were divided into three samples, each incubated prior to emulsification: 0 hr, 0.5 hr or 1 hr, as described above. Following each of the pre-treatment duration, 0.2 g of each mixture were added to 60 ml of a water solution containing 0.1% Tween® 80 as emulsifier (for PTC19 derived mixtures) or 60 ml of plain water (for PTC20 derived mixtures) contained in a 100 ml plastic container. The obtained combinations of oil and water phases were mixed and emulsified at 2,000 rpm for 30 seconds using a planetary centrifugal mixer, as detailed in Example 2. The pH of the amino-silicone emulsions so prepared was measured and found to be of about 10, the minute amount of acid water on reactants contributing but a small portion of the solid content of the emulsion being negligible.

Hair samples were colored according to Example 4 and their feel, coloration and wash resistance were studied as described in Examples 5 to 7. All hair samples accordingly colored with any of $ASE19_{t0}$ to $ASE20_{t1}$ emulsions as first coat, provided a strong coloration (with an OD of at least 1.2) and a pleasant non-tacky feel following the application of a pigmented polymeric dispersion comprising Chromophtal® Violet K5800, prepared as described in Example 3.

More interestingly, the reactive amino-silicone emulsions prepared with reactant humidified with acid water provided permanency of coloration (as assessed by wash-resistance) at earlier time points of pre-treatment, as compared to emulsions prepared with anhydrous reactants or with reactants supplemented with neutral water. Permanency of coloration was assessed about 24 hours after application of the second coat.

When PTC19 (including KF-857 with 0.5 wt. % of acid water) was immediately emulsified to form $ASE19_{t0}$, the hair colored therewith was not wash resistant ($OD_{wash}/OD_{base}$~60%). This phenomenon was already reported in previous examples for ASEs already discussed, wash-resistance typically developing to permanency with longer pre-treatment durations of at least 2 hours. PTC3, which corresponds to PTC19, except for the added water being neutral, supported permanent coloring when pre-treated for 4 hours. However, when PTC19 was emulsified after only half-an-hour of pre-treatment, wash resistance of ASE19 to 0.5 dramatically increased, the ratio of $OD_{wash}/OD_{base}$ being of about 91%, well above the threshold of 80% OD retention defining permanency of coloration. This effect on permanency, attributed to the presence of acid water in a reactant, was further confirmed with hair samples colored, with $ASE19_{t1}$ as first coat, the incubation of the oil phase of the emulsion for one hour resulting in $OD_{wash}/OD_{base}$ ratio of about 96%.

The results obtained with PTC20 (including Dynasylan® SIVO 210 with 2.0 wt. % of acid water) and derived emulsions $ASE20_{t0}$ to $ASE20_{t1}$ were even more dramatic. When PTC20 was directly emulsified to form $ASE20_{t0}$, the hair colored therewith was immediately wash resistant, with an $OD_{wash}/OD_{base}$ ratio of ~99%. Hair colored with an emulsion for which the pre-treatment of the oil phase was of up to one hour ($ASE20_{t1}$) continued to provide permanency the $OD_{wash}/OD_{base}$ ratio being of about 93%. Comparing these results with PTC21, corresponding to PTC20 except for the added water being neutral, further emphasize the advantage of acid water, as ASE21 supported permanent coloring when pre-treated 24 hours.

These results demonstrate that, while the addition of neutral water to reactants of reactive amino-silicone emulsions can significantly accelerate desired behavior/outcome of hair colored according to the present teachings, this can be further dramatically improved by modifying the pH of the added water. In the present study, adding acid water shortened the pre-treatment duration to about a tenth or less of the time achievable with the addition of neutral water. For reference, adding water to control compositions formed of dried reactants (e.g., AnPTC1 and AnPTC2) already shortened the time till appearance of permanency to less than a fifth of the original latency for un-treated emulsions.

Example 13: Resistance to Alcohol

Permanency, as observed with the above-detailed samples in previous examples, is indicative of shampoo-resistance, a shampoo-resistant coloration being deemed wash-resistant to plain water lacking any aggressive detergent. As alcohol, particularly volatile alcohols, can be found in numerous hair care products, alcohol-resistance was assessed.

Hair samples were first coated with an emulsion prepared from PTC3 incubated for 4 hours (which according to Example 12 could be replaced by PTC19, enabling a shortening of the pre-treatment duration to no longer than 0.5 hour). A dispersion of neutralized polymeric particles embedding Pigment Violet 23 in EAA copolymers (Primacor™ 5990I:Luwax® EAS-5 at 1:1) was then applied as a second coat, and the colored hair samples were subjected to a test assessing their resistance to alcohol (undiluted or diluted in distilled water). The test was performed about 24 hours after application of the second coat.

Three types of alcohols were tested, all anhydrous and 99.9% pure, supplied by BioLab, Israel: methanol ($CH_3OH$); ethanol ($C_2H_6O$); and isopropanol ($C_3H_8O$). Each of them was tested either undiluted (the alcohol forming 100 wt. % of the solution) or diluted with distilled water to form aqueous solutions containing 10 wt. % or 50 wt. % of alcohol. For each alcoholic sample, a few drops of the solution (~0.2 ml) were dripped over a colored hair tress, to mimic amounts that may be applied by spraying conventional hair products. The hair sample was then lightly rubbed using fingers to ensure proper coverage by the various alcohol solutions. The uniformly wet hair sample was then dabbed lightly on a piece of white tissue (Kimwipes® disposable wipers, Kimberly Clark, USA. If some of the color was transferred from the colored hair samples to the fingers during the rubbing step and/or to the white tissue during the dabbing step, the coloration was considered sensitive to the particular alcohol solution. Conversely, if no color transferred/was visible on the fingers and white tissue, then the coloration was considered resistant to the alcohol solution under study, thus alcohol-resistant.

The above-described hair samples colored according to the present teachings (e.g., with a condensation-curable amino-silicone emulsion, as first coat, presently $ASE3_{t4}$) displayed resistance to aqueous solutions containing up to 50 wt. % of methanol, ethanol and isopropanol. There were no detectable differences amongst the three types of C1 to C3 alcohols. Hence, the present compositions not only provide wash-resistance and shampoo-resistance, but also significant alcohol-resistance.

Hair colored according to the present disclosure, once condensation curing has sufficiently proceeded or is substantially completed, do not transfer color. This can be quantitatively confirmed by an unaffected coloration (OD) of the colored samples. In other words, there is no or only minor reduction in optical density (e.g., $OD_{alcohol}/OD_{base} \geq 0.8 \times OD_{base}$) when exposed to aqueous alcoholic solutions containing at most 50 wt. % of alcohol by weight of the solution, or at most 40 wt. % of alcohol, or at most 30 wt. % of alcohol, or at most 20 wt. % of alcohol, or at most 10 wt. % of alcohol per total weight of the alcoholic solution. Alcohols typically used in hair care products which may cause such color transfer and/or reduction in optical density include linear, branched or cyclic alcohols having up to 12 carbon atoms in the molecule, alcohols having up to 6 carbon atoms being deemed more volatile than the longer molecules and possibly more frequent in hair care products such as hair fixatives.

A similar test was performed with commercially available hair care products deemed to represent more conventional situations of exposure of colored hair to products containing alcohol. Hair samples colored with an emulsion prepared from a modified version of PTC16 (containing 2 wt. % of water added to GP-965) incubated for 24 hours (which according to Example 12 could be replaced by PTC20, enabling an immediate emulsification with a null pre-treatment duration) as first coat and with a dispersion of neutralized polymeric particles embedding Pigment Violet 23 as a second coat, were prepared as previously described. The test was performed about 24 hours after application of the second coat. The colored hair samples were sprayed or massaged with one of two commercially available hair care products, both by Schwarzkopf. The first product was a hair fixative (Oasis+ Freeze Pump Spray) and the second product was a finishing treatment (Professional BC Bonacure Oil Miracle Hair Therapy). The fixative is believed to contain a higher amount of volatile alcohol, as compared to the finishing lotion.

Following the application of the aerosol or lotion, the hair samples were massaged to ensure proper coverage by the hair care products including the different alcohol contents. The hair samples colored with $ASE16.5_{r4}$ as first coat were found to resist both hair care products, displaying no color transfer to fingers or white tissue, nor any visually detectable discoloration of the fibers.

Taking all foregoing results, it is concluded that by proper selection of at least one of (a) the amount of water being added per reactant, (b) the pH of water being added, (c) the number of reactants being supplemented with such water (or pH modified aqueous solutions) additions (which in turn affect (d) the amount of water being added per reactive oil phase, and (e) the duration of pre-treatment of the reactive oil phase), a desired hair coloration outcome can be tailored. The outcome can relate, by way of non-limiting example, to the feel of the colored hair, to the coloration characteristics (e.g., intensity, brightness, vividness, etc.) or to the resistance of the coloration to any particular factor (e.g., wash resistance which set the degree of permanency of the coloration, alcohol-resistance, etc.).

The desired outcome can further relate to the onset of a desired property (e.g., immediate coloration), to the termination of a less satisfactory or undesired property (e.g., immediate termination of tacky feel), or to the time-window during which a pre-treatment of the reactive oil phase enables a desired property (e.g., permanency of coloration being rapidly achievable and continuing for a long enough period to render the coloring system less sensitive time variations). Time variations can result from the operator, for instance the time required for preparation, emulsification, application on the hair, and any such step of the coloring method under human control. The time variations can also result from the subject for whom the coloring method is performed, a person having more/longer hair may require a longer time for application of the compositions than a person having less/shorter hair. Understandingly, the compositions must be stable and provide a uniform desired outcome during the entire period from beginning at least to end of application.

Example 14: Hair Appearance

Hair coated according to the present teachings were generally soft to the touch, displayed a shiny healthy appearance, as well in some instances as a volume improvement, as assessed by trained observers. The volume improvement was assessed against an uncoated reference and is believed to be due to the mild increase in hair diameter as a result of the thin amino-silicone film formed thereon. A film having a thickness of about 0.3-1.0 µm increases the diameter of the fiber by about 0.6-2.0 µm. Assuming a hair fiber having a diameter of about 50-100 µm, such coats provide for a diameter increase of approximately 0.5-5%.

In addition to satisfactory or even improved appearance, the hair samples coated according to the present disclosure were combable (the coating/coloring resulting in smooth individual fibers) and found to behave in this respect in a manner comparable to uncoated controls. Such findings (even made in control compositions devoid of coloring pigments) are notable, since conventional coloring methods generally tend to reduce the natural shine of the hair and/or are likely to weaken the hair fibers. In order to quantify such observations, hair samples coated/colored according to the present teachings can be subjected to the following assessment.

The coated hair samples are mounted and combed on a cylinder to align hair fibers. Shine can be monitored using a Samba hair system, Bossa Nova Technologies, USA, the measurements being collected using a polarized incident light for the identification between specular and diffused light on the cylinder mount on which samples are disposed. The shine parameter is the first reflection that carries the same polarization of the incident light. For each hair sample, including an uncoated control of the same hair type, gloss measurements are taken in at least three different areas of the tuft and averaged. Results are provided in Arbitrary Units (AU) of shine. For reference, changes in 1 AU or less are generally not detectable to the naked eye, while changes in 2 AU or less are considered tolerable for most colors. Advantageously the shine of hair fibers coated according to the present teachings will be stable as long as the coating is not removed from the fibers. The available qualitative results suggest that the present coloring method does not harm the hair fibers, and may even improve their volume.

Example 15: Hair Robustness

While conventional coloring methods, especially when a permanent effect is sought, generally damage the hair fiber and are likely to weaken it, reducing its mechanical resilience, hair samples coated according to the present teachings are believed to be at least as resistant as uncoated counterparts. The robustness of the hair can be assessed as follows.

For each sample, coated and uncoated control, individual hair fibers are tested in an LR X Plus test machine of Ametek Lloyd Instruments to assess the force applied at break point, the fiber being subjected to a load of 20 Newton at a load speed of 1 mm/min. The diameter of each tested fiber is measured using a handheld micrometer. The Force at Break Point (in N) is normalized to the diameter (in mm), and the results of 6 fibers is averaged. The normalized force at breakpoint of hair fibers coated according to the present teachings is then compared to same force for native uncoated hair fibers. A similar behavior as far as resistance to tension and breakpoint force is concerned for both coated samples and uncoated control suggests that the present compositions and methods do not impair the mechanical properties of the hair, a damage frequently observed when coloration is performed by conventional dye methodology.

Example 16: Coloration of Textile Samples

While in previous examples, the efficacy of the methods and compositions according to the present teachings was demonstrated on hair fibers, the following demonstrate their applicability to textile fibers, including on fabrics made therefrom.

Keratinous Textile Fibers:

A tuft of 100% wool 10 cm long yarn pieces was provided.

A pre-treatment composition based on the PTC9-17 series was prepared as detailed in Example 1 (wherein 2 wt. % of neutral water were added to Dynasylan® SIVO 210 instead of being added to either GP-965 or GP-967). 0.2 g of said pre-treatment composition was mixed and emulsified with 60 ml of plain water, as described in Example 2, with no incubation time, to yield a Dynasylan® SIVO 210 reactive amino-silicone emulsion.

Non-Keratinous Textile Fibers:

Six different fabric samples were analyzed: three synthetic textile fibers' samples, made of a) 92% polyester, b) chiffon, and c) lycra; and three natural textile fibers' samples made of various types of cotton, termed a) cotton 1, b) cotton 2, and c) cotton 3, all swatches having a surface of about 7 by 4 cm. The fiber types of the synthetic samples were analyzed by FTIR between the range of 400-4000 $cm^{-1}$, and identified to match 92% and 96% of a polyester profile, the lycra fabric sample being identified as polyether-polyurea copolymer. Cotton fibers of the natural samples are mainly made up of cellulose.

The MTMS pre-treatment composition, prepared as detailed in Example 1, was provided as ASE22 to reactive amino-silicone emulsion, according to Example 2.

Coloration of the textile samples was conducted as follows:

1—Each textile sample (fabric swatch or yarn tuft) was dipped with gentle stirring for about 60 seconds in the respective reactive amino-silicone emulsion.

2—The textile samples coated with the reactive amino-silicone emulsion were then thoroughly rinsed with tap water at about 25° C. to remove any excess of the emulsion.

3—Each of the rinsed textile samples coated with the reactive amino-silicone emulsion was then dipped with gentle stirring for about 60 seconds in an aqueous dispersion of neutralized polymer-embedded pigment (Pigment Red 122, CI 73915, for the wool samples and Pigment Orange 43, CI 71105, for the non-keratinous natural or synthetic fibers), prepared as described in Example 3. The composite pigment-copolymer constituted 10 wt. % by weight of the final aqueous neutralized dispersion, the conductivity of which was of less than 3 milliSiemens.

4—Each of the textile samples coated with a dispersion of polymer-embedded pigment was then rinsed with tap water at about 25° C. for a few seconds to remove excess of coloring dispersion.

5—Each of the rinsed textile samples was washed with a standard cationic shampoo (Keratin Smooth, TRESemmé, Unilever, England), the textile samples being gently massaged with the shampoo to ensure proper coverage, and then thoroughly rinsed with tap water at about 25° C.

6—The rinsed colored textile samples were dried for approximately 1 hour in an oven (Forced Convection Oven JSOF-100 by JSR, Korea) at a temperature of about 40° C., and maintained at room temperature (circa 23° C.) for 7 days.

Example 17: Wash Processes of the Textile Samples

Permanence of the textile samples' coloration was tested by subjecting the colored textile samples to washing processes, emulating washing machine cycles.

Washing-Machine Emulation i. Each textile sample was placed in a 100 ml cup, containing other pieces of various fabrics, to emulate friction effects of clothes inside a washing machine. The total weight of the textile sample and the emulating fabrics was 10 g;

ii. Textile cleaning liquid, containing 5-15% non-ionic surface-active agents (Sano Maxima, Sano, Israel), was added in an amount calculated as 1% of the total fabric weight in the cup, as well as 90 ml of tap water at a temperature of about 60° C. The cup was placed in a planetary mixer (ARE-250, Thinky, Japan) and mixed for 15 min at 700 rpm, the temperature of the washing liquid progressively decreasing to RT;

iii. The water and the detergent were removed by decanting, and replaced by fresh tap water at 60° C., and further stirred for 15 min at 700 rpm;

iv. The water was removed again and replaced by a fabric softener containing less than 5% anionic surface-active agents (Soad, Henkel, manufactured in Israel) in an amount calculated as 1% of the total fabric weight in the cup, as well as 90 ml of tap water at room temperature. The cup was placed again in the planetary mixer, and stirred for 5 minutes at 700 rpm;

v. The textile sample was removed from the cup and dried in an oven at 40° C. for 1 hour.

The optical density (OD) of the textile samples was measured at the different stages of the various processes as described in Example 7, and the results are summarized in Table 6, which also presents the percentage of decrease in OD between initial and final values (% Loss).

The wool Initial OD value was calculated as an average of the optical densities measured at 3 locations on the wool tuft, and the Final OD for the wool sample was similarly measured, averaging optical density values at 5 locations on the wool tuft after its washing.

The Initial OD values for the fabric samples were calculated as an average of the optical densities measured at 3 locations on each fabric sample, colored as described in Example 16. The Final OD values were similarly measured, averaging optical density values at 3 locations on each fabric sample after its washing.

TABLE 6

| Fabric Type | Initial OD | Final OD | % Loss |
|---|---|---|---|
| Wool | 0.92 | 0.81 | 12.27 |
| Cotton 1 | 1.02 | 0.97 | 4.90 |
| Cotton 2 | 0.84 | 0.80 | 4.76 |
| Cotton 3 | 0.73 | 0.70 | 4.11 |
| 92% Polyester | 1.03 | 0.96 | 6.80 |
| Chiffon | 0.95 | 0.90 | 5.26 |
| Lycra | 0.97 | 0.95 | 2.06 |

From the table, it can be seen that the coloration according to the present invention is effective on both synthetic and natural fabrics. Also, permanency was achieved for all fiber types when tested after the washing machine emulation.

Example 18: Analysis of Coated or Colored Textile Fibers

Textile fibers coated with a reactive amino-silicone emulsion, and then by an aqueous dispersion of neutralized polymer according to Example 16, can be analyzed to demonstrate the specific characteristics of the coating. The reactive amino-silicone emulsion or the aqueous dispersion can contain pigments, resulting in colored textile fibers. In the absence of any such pigments, the obtained coating could have various uses, as demonstrated in Example 19. The analysis of the coating can be performed as follows:
Outer Thermoplastic Layer:

First, the outer layer of the coated fabric can be analyzed non-destructively by XPS, whereby the polymeric chemistry of the thermoplastic layer can be characterized, e.g., what type of polymer is present in the coating.

The coated fabric can alternatively or additionally be placed in a container containing a solvent suitable for dissolving solely the outer polymeric layer (e.g., THF or DMSO), and the fabric is maintained in the solvent for sufficient time to allow the dissolution of the outer polymeric layer into the solvent (e.g., 10 minutes). The fabric is then taken out of the solvent and placed aside for drying.

The obtained solvent mixture, containing the solvent and any components originating from the outer layer (polymers, pigments, if present, plasticizers etc.), undergoes evaporation of the solvent, whereby the dried solid components remain and can be analyzed by:
i. FTIR to detect the presence of acid groups on the polymeric material;
ii. DSC analysis to measure the melting point (Tm) of the dried components of the thermoplastic layer. The Tm is expected to be within the range of 50° C. to 250° C.;
iii. SEM/EDS analysis to detect the presence of metal ions, originating from neutralizing the acid groups in certain cases with metal ion-based neutralizing agents; or
iv. Carbon NMR to detect and quantify carbons linked to acidic groups.

Inner Thermosetting Layer

The thermosetting layer, made of cross-linked amino-silicones, can be removed from the textile fibers by scraping the fibers with a knife to remove flakes of the rigid layer. The obtained flakes of the thermosetting layer can be analyzed by:
i. FTIR to detect the presence of characterizing bonds such as silicone-oxygen or silicone-nitrogen;
ii. DSC analysis to measure the Tg of the thermosetting layer. The Tg is expected to be within the range of −100° C. to +20° C.;
iii. FIB-SEM or TEM analysis, wherein the layers are visible in a cross-section of a textile fiber, to detect the presence of a reinforcement filler (e.g., fumed silica) in the thermosetting layer using electron microscopy; or
iv. Silicone NMR to characterize the cured silicone polymer.

For the purpose of textile coloration, pigmented compositions are used, and thus, the colored textile fibers are expected to have pigments present in the outer thermoplastic layer (if pigments were contained in the aqueous dispersion of the polymeric particles) and/or in the inner thermosetting layer (if pigments were contained in the reactive amino-silicone emulsion). This can be detected, e.g., by FIB-SEM or TEM, as described above, wherein pigments encompassed by any one, or both of the layers would be visible using electron microscopy.

Example 19: Color Retention of Coated Fabrics

The ability of the coatings of the present invention to reduce fading or color loss of textile fibers after repeated washing cycles was tested.
Preparation of Reactive Amino-Silicone Emulsions
Pre-Treatment Composition 23 (PTC23)

A methyltrimethoxysilane (MTES) pre-mix was prepared by placing ethanol (20.6 wt. % by weight of PTC23) and MTES (51 wt. % by weight of PTC23) in a 500 ml 4-way glass flask. The flask was placed in an oil bath, and the mixture was heated to a temperature of 50° C., and then mixed for 10 minutes at that temperature.

1% sulfuric acid (7.7 wt. % by weight of PTC23) was slowly added into the flask containing the MTES pre-mix, and the temperature was raised, so that the mixture reached a temperature of 60-70° C., followed by mixing for 10 minutes. Dynasylan® AMEO (20.6 wt. % by weight of PTC23) was then added and mixed for 30 minutes to yield a Dynasylan® AMEO amino-silicone PTC23.
Reactive Amino-Silicone Emulsions 23 (ASE23)

Reactive amino-silicone emulsions $ASE23_1$ and $ASE23_2$ were prepared. $ASE23_1$, containing a higher-concentration of the reactive amino-silicone, was prepared by mixing together 0.2 g of the PTC23 and 2.5 ml water. Similarly, an emulsion containing a lower-concentration of the reactive amino-silicone, denominated $ASE23_2$, was prepared by mixing together 0.4 g of the PTC23 and 60 ml water.
Preparation of Aqueous Dispersion Comprising Polymeric Material Having Acid Moieties The aqueous dispersion containing 10% of neutralized Ethylene/Sodium Acrylate Copolymer (EcoSmooth™ Satin by Dow Chemicals, having an AA content of about 20 wt. %) in water was prepared.

The compositions prepared as described above did not contain any pigments, so as to avoid significantly changing the original color of the fabric. However, while the absence of pigments facilitates assessing the activity of a pigment-less coating, this is not essential, and coatings additionally including a pigment in at least one of their layers are also expected to prevent color loss, were the textile fiber initially dyed.

Three black poly-cotton swatches (70% cotton, 30% polyester) cut from the same fabric, each having a surface of about 5×5 cm, were used.

Swatch 1 remained un-coated and was used as a reference. Swatches 2 and 3 were coated as described in Example 16, wherein the higher-concentration reactive amino-silicone $ASE23_1$ was used in step 2 for Swatch 2, and the lower-concentration reactive amino-silicone $ASE23_2$ was used in step 2 for Swatch 3.

Following step 6 of Example 16, a dry coating was formed on the surface of Swatches 2 and 3, and their CIE L*a*b* color space values were measured using an X-Rite 939 (illuminant type D65, geometry of 0/45°) spectrophotometer. The measurements were performed at 3 places on each swatch to obtain average baseline CIE L*a*b* values. Similarly, the average baseline values were obtained for the un-coated reference Swatch 1.

The three textile samples were then subjected to a series of 12 washing cycles at a temperature of 60° C. and spin cycles at up to 700 RPM in a washing machine (Constructa, Germany), using a standard laundry gel capsule (Sunday Active Power Wash, by Zohar Dalia, Israel) for each cycle. After each washing cycle, the textile samples were rinsed with tap water for 20 seconds, dried using a hair dryer for 1.5-2 minutes, and then the CIE L*a*b* values were measured as described above. The difference in color (ΔE) after each washing cycle was measured compared to the baseline L*a*b* values according to the formula:

$$\Delta E = \sqrt{(L^*_{wash} - L^*_{baseline})^2 + (a^*_{wash} - a^*_{baseline})^2 + (b^*_{wash} - b^*_{baseline})^2}$$

The highest absolute ΔE value of 4.54 was calculated for the un-coated Swatch 1, demonstrating the most substantial color loss after twelve such cycles. The lowest ΔE value of 2.46 was calculated for Swatch 2, demonstrating a reduction in fading or color loss, due to the coating formed by the composition including in the first layer the higher concentration of reactive amino-silicones. The ΔE value of Swatch 3 having a coating including a relatively lower concentration of amino-silicones was 2.69, which is slightly higher than that of Swatch 2. Still the change in color of Swatch 3 following the twelve washing cycles (ΔF=2.69) is less than the loss of color observed with similarly washed un-coated Swatch 1 (ΔE=4.54). Both coatings reduced the color loss (or delayed it) by at least 40% and on average reduced the loss observed with an uncoated reference by a ΔE of about 2, deemed the level of detection of a change in color by the naked eye, and of less than 3.

In the description and claims of the present disclosure, each of the verbs, "comprise" "include" and "have", and conjugates thereof, are used to indicate that the object or objects of the verb are not necessarily a complete listing of members, components, elements, steps or parts of the subject or subjects of the verb.

As used herein, the singular form "a", "an" and "the" include plural references and mean "at least one" or "one or more" unless the context clearly dictates otherwise. At least one of A and B is intended to mean either A or B, and may mean, in some embodiments, A and B.

Unless otherwise stated, the use of the expression "and/or" between the last two members of a list of options for selection indicates that a selection of one or more of the listed options is appropriate and may be made.

As used herein in the specification and in the claims section that follows, the term "largely includes", with respect to a component within a formulation, refers to a weight content of at least 30% of that component. The term "largely acidify" refers to at least 50% of neutralizable acid moieties being in native form or acid-conjugated form of previously neutralized moieties.

As used herein in the specification and in the claims section that follows, the term "mostly includes" or "mainly includes", with respect to a component within a formulation, refers to a weight content of at least 50% of that component. The term "mainly acidify" refers to at least 75% of neutralizable acid moieties being in native form or acid-conjugated form of previously neutralized moieties.

In the discussion, unless otherwise stated, adjectives such as "substantially" and "about" that modify a condition or relationship characteristic of a feature or features of an embodiment of the present technology, are to be understood to mean that the condition or characteristic is defined to within tolerances that are acceptable for operation of the embodiment for an application for which it is intended, or within variations expected from the measurement being performed and/or from the measuring instrument being used.

Furthermore, unless otherwise stated, the terms used in this disclosure should be construed as having tolerances which may depart from the precise meaning of the relevant term but would enable the invention or the relevant portion thereof to operate and function as described, and as understood by a person skilled in the art.

When the term "about" precedes a numerical value, it is intended to indicate +/−15%, or +/−10%, or +/−5%, or +/−1%, and in all instances is meant to include the precise value. It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination or as suitable in any other described embodiment of the disclosure. Certain features described in the context of various embodiments are not to be considered essential features of those embodiments, unless the embodiment is inoperative without those elements.

While this disclosure has been described in terms of certain embodiments and generally associated methods, alterations and permutations of the embodiments and methods will be apparent to those skilled in the art. The present disclosure is to be understood as not limited by the specific embodiments described herein, and the materials, methods and examples described herein are merely exemplary, and are intended to provide an overview or framework to understanding the nature and character of the invention as it is claimed, and are not intended to be necessarily limiting. Accordingly, it is intended to embrace all such alternatives, modifications and variations and to be bound only by the spirit and scope of the disclosure and any change which come within their meaning and range of equivalency.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

To the extent necessary to understand or complete the disclosure of the present disclosure, all publications, patents, and patent applications mentioned herein, including in particular the applications of the Applicant, are expressly incorporated by reference in their entirety by reference as is fully set forth herein.

Certain marks referenced herein may be common law or registered trademarks of third parties. Use of these marks is by way of example and shall not be construed as descriptive or limit the scope of this disclosure to material associated only with such marks.

We claim:

1. A method of coating textile fibers, the method comprising:
   (a) providing an oil phase containing at least one reactive condensation-curable film-forming amino-silicone pre-polymer, said oil phase fulfilling at least one of the following:
      (i) said at least one reactive condensation-curable film-forming amino-silicone pre-polymer includes at least one reactive condensation-curable film-forming amino-silicone monomer having a molecular weight of at most 1,000 g/mole; and
      (ii) said oil phase further contains a non-amino cross-linking agent adapted or selected to cure said at least one reactive condensation-curable film-forming amino-silicone pre-polymer, said non-amino cross-linking agent having a molecular weight of at most 1,000 g/mole;
   wherein at least one of said reactive condensation-curable film-forming amino-silicone pre-polymer, said reactive condensation-curable film-forming amino-silicone monomer, said non-amino cross-linking agent, or any one of a silicone oil, an amino-silicone oil and a reactive hydrophobic inorganic filler optionally further comprised therein, is a water-enriched reactant;
   the water-enriched reactant having a water content, so as to obtain, following a pre-treatment duration of the oil phase, a pre-treated oil phase having at least 0.01 wt. % and optionally at most 8 wt. % of water by weight of said pre-treated oil phase;

(b) emulsifying said pre-treated oil phase with an aqueous phase, so as to obtain a pre-treated oil-in-water emulsion;

(c) applying, on an external surface of the textile fibers, said pre-treated oil-in-water emulsion; and (d) after partial condensation curing of said pre-polymer of the pre-treated oil-in-water emulsion has occurred, so as to form an at least partially cured amino-silicone coat on the external surface of the textile fibers, applying on the at least partially cured amino-silicone coat, an aqueous dispersion comprising a plurality of polymeric particles, formed of a hydrophilic polymeric material having neutralized acid moieties, said plurality of polymeric particles being dispersed within said aqueous dispersion, to produce an overlying polymeric layer adhering to an external surface of said amino-silicone coat.

2. A method according to claim 1, wherein said water-enriched reactant is obtained by adding an aqueous pre-treatment solution to a substantially dry reactant containing less than 1 wt. % of water by weight of dry reactant, said aqueous pre-treatment solution:
  a) consisting essentially of distilled water having a pH in the range of 6.5 to 7.5; or
  b) further comprising an acid, said acid being optionally a volatile acid, and wherein said aqueous pre-treatment solution optionally has a pH in the range of 0.5 to 2.5.

3. A method according to claim 1, wherein said pre-treated oil phase is obtained by adding to the oil phase an aqueous pre-treatment solution in an amount of 8 wt. % or less, and optionally 0.01 wt. % or more by weight of the oil phase, said aqueous pre-treatment solution:
  a) essentially consisting of distilled water having a pH in the range of 6.5 to 7.5; or
  b) further comprising an acid, said acid being optionally a volatile acid, and wherein said aqueous pre-treatment solution optionally has a pH in the range of 0.5 to 2.5.

4. A method according to claim 1, wherein the pre-treatment duration of the oil phase is of 24 hours or less.

5. A method according to claim 1, wherein said at least one reactive condensation-curable film-forming amino-silicone pre-polymer has at least one of the following structural features:
  a) at least 3 silanol and/or hydrolysable groups (3+SiOH), so as to form a 3-dimensional network;
  b) a solubility in water of less than 1% by weight, at 23° C.; and
  c) includes reactive groups selected from the group consisting of alkoxy-silane reactive groups, silanol reactive groups and combinations thereof.

6. A method according to claim 1, wherein said oil phase or said pre-treated oil phase, exclusive of all inorganic content and of any pigment, is devoid of a glass transition temperature.

7. A method according to claim 1, wherein said partial condensation curing is effected at a temperature of at most 75° C., and optionally, at least 15° C.

8. A method according to claim 1, wherein said oil-in-water emulsion or pre-treated oil-in-water emulsion has a surface zeta potential greater than zero, or at least +1 mV; and optionally, at most +100 mV, said surface zeta potential being further optionally measured at a native pH of said oil-in-water emulsion.

9. A method according to claim 1, wherein at a pH of said aqueous dispersion, said oil-in-water emulsion or pre-treated oil-in-water emulsion has a first surface zeta potential ($\zeta 1$), and said aqueous dispersion has a second zeta potential ($\zeta 2$), wherein a zeta potential differential ($\Delta \zeta$) at said pH is defined as $\Delta \zeta = \zeta 1 - \zeta 2$, and wherein $\Delta \zeta$, in millivolts (mV), fulfills at least one of the following:
  (i) $\Delta \zeta$ is at least 10;
  (ii) $\Delta \zeta$ is within a range of 10 to 80; and
  (iii) for said pH being within a range of 4 to 11, said first surface zeta potential ($\zeta 1$), is greater than zero ($\zeta 1 > 0$).

10. A method according to claim 1, further comprising sufficiently converting said hydrophilic polymeric material into a conjugate acid thereof, so as to obtain a hydrophobic polymeric layer.

11. A method according to claim 1, wherein:
  i) at least one of said oil phase or said pre-treated oil phase of the pre-treated oil-in-water emulsion further contains a first pigment, optionally as a plurality of sub-micronic first pigment particles and further optionally contains a first dispersant, said sub-micronic first pigment particles being dispersed within said first dispersant, said first dispersant optionally being in an amount within a range of 25% to 400% by weight of the first pigment; and/or
  ii) said plurality of polymeric particles of the aqueous dispersion further contains a second pigment, optionally as a plurality of sub-micronic second pigment particles and further optionally contains a second dispersant, said sub-micronic second pigment particles being dispersed within said second dispersant, said second dispersant optionally being in an amount within a range of 25% to 400% by weight of the second pigment;
  the first and second pigment and/or the first and second dispersant being same or different.

12. A method according to claim 1, wherein the textile fibers are selected from: natural keratinous fibers, natural non-keratinous fibers and synthetic fibers.

* * * * *